(12) United States Patent
Makings et al.

(10) Patent No.: US 7,696,201 B2
(45) Date of Patent: Apr. 13, 2010

US007696201B2

(54) MODULATORS OF MUSCARINIC RECEPTORS

(75) Inventors: Lewis R. Makings, Encinitas, CA (US); Dennis J. Hurley, San Marcos, CA (US); Gabriel Raffai, Tucson, AZ (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

(21) Appl. No.: 11/893,245

(22) Filed: Aug. 15, 2007

(65) Prior Publication Data

US 2008/0176843 A1 Jul. 24, 2008

Related U.S. Application Data

(60) Provisional application No. 60/837,786, filed on Aug. 15, 2006.

(51) Int. Cl.
*A61K 31/537* (2006.01)
*A61K 31/536* (2006.01)
*C07D 273/01* (2006.01)
*C07D 265/14* (2006.01)

(52) U.S. Cl. ................. 514/230.5; 544/70; 544/92

(58) Field of Classification Search ........... 544/70, 544/92; 514/230.5
See application file for complete search history.

(56) References Cited

U.S. PATENT DOCUMENTS

| | | | |
|---|---|---|---|
| 3,654,287 A | 4/1972 | Dykstra | |
| 3,666,764 A | 5/1972 | Campbell et al. | |
| 3,959,475 A | 5/1976 | Bauer et al. | |
| 3,962,259 A | 6/1976 | Bauer et al. | |
| 4,233,307 A | 11/1980 | Ono et al. | |
| 4,349,549 A | 9/1982 | Roszkowski et al. | |
| 4,558,049 A | 12/1985 | Bernardi et al. | |
| 5,091,387 A | 2/1992 | Evans et al. | |
| 5,219,860 A | 6/1993 | Chambers et al. | |
| 5,536,716 A | 7/1996 | Chen et al. | |
| 5,576,321 A | 11/1996 | Krushinski et al. | |
| 5,578,593 A | 11/1996 | Chen et al. | |
| 5,614,523 A | 3/1997 | Audia et al. | |
| 5,627,196 A | 5/1997 | Audia et al. | |
| 5,652,235 A | 7/1997 | Chen et al. | |
| 5,658,921 A | 8/1997 | Perregaard et al. | |
| 5,741,789 A | 4/1998 | Hibschman et al. | |
| 5,789,402 A | 8/1998 | Audia et al. | |
| 5,817,679 A | 10/1998 | Shen et al. | |
| 5,885,999 A | 3/1999 | Elliott et al. | |
| 6,013,652 A | 1/2000 | Maccoss et al. | |
| 6,130,217 A | 10/2000 | Arnold et al. | |
| 6,166,040 A | 12/2000 | Fairhurst et al. | |
| 6,326,375 B1 | 12/2001 | Fukami | |
| 6,436,962 B1 | 8/2002 | Hoffman et al. | |
| 6,566,367 B2 | 5/2003 | Bakthavatchalam et al. | |
| 6,720,324 B2 | 4/2004 | Marzabadi et al. | |
| 6,828,440 B2 | 12/2004 | Goehring et al. | |
| 6,869,960 B2 | 3/2005 | Ito et al. | |
| 6,943,199 B2 | 9/2005 | deLombaert et al. | |
| 7,045,527 B2 | 5/2006 | Chen et al. | |
| 7,205,417 B2 | 4/2007 | Fukami et al. | |
| 2002/0188124 A1 | 12/2002 | Fukami et al. | |
| 2003/0036652 A1 | 2/2003 | Bakthavatchalam et al. | |
| 2003/0158219 A1 | 8/2003 | Ito et al. | |
| 2004/0054177 A1 | 3/2004 | Otake et al. | |
| 2004/0072847 A1 | 4/2004 | Bakthavatchalam et al. | |
| 2004/0122074 A1 | 6/2004 | Dow et al. | |
| 2004/0142956 A1 | 7/2004 | Chen et al. | |
| 2004/0204397 A1 | 10/2004 | Chaturvedula et al. | |
| 2005/0033048 A1 | 2/2005 | Bakthavatchalam et al. | |
| 2005/0153998 A1 | 7/2005 | Ito et al. | |
| 2005/0176703 A1 | 8/2005 | Gabriel et al. | |
| 2005/0215576 A1 | 9/2005 | Degnan et al. | |
| 2005/0261332 A1 | 11/2005 | Distefano et al. | |
| 2006/0019962 A1 | 1/2006 | Makings et al. | |
| 2006/0040964 A1 | 2/2006 | Bakthavatchalam et al. | |
| 2006/0111380 A1 | 5/2006 | Otake et al. | |
| 2006/0173027 A1 | 8/2006 | Marzabadi et al. | |
| 2006/0183904 A1 | 8/2006 | Guo et al. | |
| 2006/0211722 A1 | 9/2006 | Jiao et al. | |
| 2006/0217372 A1 | 9/2006 | Blanco-Pillado et al. | |
| 2007/0043023 A1 | 2/2007 | Makings et al. | |
| 2007/0254903 A1 | 11/2007 | Boatman et al. | |

FOREIGN PATENT DOCUMENTS

| | | |
|---|---|---|
| CN | 1535967 | 10/2004 |
| DE | 3342164 | 5/1984 |
| EP | 0065864 | 12/1982 |

(Continued)

OTHER PUBLICATIONS

PCT International Search Report dated May 15, 2008 for International Application No. PCT/US2007/018012.
Abdel-Magid, A. "Reductive Amination of Aldehydes and Ketones with Sodium Triacetoxyborohydride. Studies on Direct and Indirect Reductive Amination Proceduresl", J. Org. Chem., 61 (1996), pp. 3849-3862.
Bignan, G., "Preparation of 3-Spirocyclic Indolin-2-ones as Ligands for the ORL-1 Receptor", Bioorganic and Medicinal Chem. Lett, 15 (2005), pp. 5022-5026.
Butera, J.. "Recent Approaches to the Treatment of Urinary Incontinence: A Survey of Patent Activity from 1995 to 1998", Expert Opinion on Therapeutic Patents, 8(8) (1998), pp. 1017-1035.

(Continued)

*Primary Examiner*—Kamal A Saeed
*Assistant Examiner*—Samantha L Shterengarts
(74) *Attorney, Agent, or Firm*—Honigman Miller Schwartz and Cohn LLP; Jonathan P. O'Brien; Christopher C. Forbes

(57) ABSTRACT

The present invention relates to modulators of muscarinic receptors. The present invention also provides compositions comprising such modulators, and methods therewith for treating muscarinic receptor mediated diseases.

37 Claims, No Drawings

FOREIGN PATENT DOCUMENTS

| | | |
|---|---|---|
| EP | 0070171 | 1/1983 |
| EP | 0128886 | 12/1984 |
| EP | 0414289 | 2/1991 |
| EP | 0444945 | 9/1991 |
| EP | 0445974 | 9/1991 |
| EP | 0486280 | 5/1992 |
| EP | 0518805 | 12/1992 |
| EP | 0533243 | 3/1993 |
| EP | 0615977 | 9/1994 |
| EP | 0722941 | 7/1996 |
| EP | 1415986 | 5/2004 |
| GB | 1575800 | 10/1980 |
| GB | 2131021 | 6/1984 |
| GB | 2308064 | 6/1997 |
| GB | 2355264 | 4/2001 |
| GB | 2355456 | 4/2001 |
| JP | 59059685 | 4/1984 |
| JP | 2001/278886 | 10/2001 |
| JP | 2002/316987 | 10/2002 |
| WO | WO 94/19367 | 9/1994 |
| WO | WO 94/22846 | 10/1994 |
| WO | WO 95/09631 | 4/1995 |
| WO | WO 95/11029 | 4/1995 |
| WO | WO 95/14025 | 5/1995 |
| WO | WO 95/28389 | 10/1995 |
| WO | WO 97/41878 | 11/1997 |
| WO | WO 97/41879 | 11/1997 |
| WO | WO 99/06434 | 2/1999 |
| WO | WO 99/32489 | 7/1999 |
| WO | WO 99/64002 | 12/1999 |
| WO | WO 00/06146 | 2/2000 |
| WO | WO 00/06153 | 2/2000 |
| WO | WO 00/06545 | 2/2000 |
| WO | WO 00/38720 | 7/2000 |
| WO | WO 01/02386 | 1/2001 |
| WO | WO-01/22919 | 4/2001 |
| WO | WO-01/29027 | 4/2001 |
| WO | WO 01/45707 | 6/2001 |
| WO | WO 01/64213 | 9/2001 |
| WO | WO 02/48152 | 6/2002 |
| WO | WO 02/070511 | 9/2002 |
| WO | WO 02/085354 | 10/2002 |
| WO | WO 02/094825 | 11/2002 |
| WO | WO 03/014083 | 2/2003 |
| WO | WO 03/037271 | 5/2003 |
| WO | WO 03/064425 | 8/2003 |
| WO | WO 03/095427 | 11/2003 |
| WO | WO 03/104236 | 12/2003 |
| WO | WO 03/106457 | 12/2003 |
| WO | WO 2003/106457 | 12/2003 |
| WO | WO 2004/004714 | 1/2004 |
| WO | WO 2004/010942 | 2/2004 |
| WO | WO 2004/010943 | 2/2004 |
| WO | WO 2004/011427 | 2/2004 |
| WO | WO 2004/028459 | 4/2004 |
| WO | WO 2004/050652 | 6/2004 |
| WO | WO 2004/074273 | 9/2004 |
| WO | WO 2004/089307 | 10/2004 |
| WO | WO 2005/016913 | 2/2005 |
| WO | WO 2005/063254 | 7/2005 |
| WO | WO 2005/063745 | 7/2005 |
| WO | WO 2005/065779 | 7/2005 |
| WO | WO 2005/075484 | 8/2005 |
| WO | WO 2005/100360 | 10/2005 |
| WO | WO 2006/001958 | 1/2006 |
| WO | WO 2006/023852 | 3/2006 |
| WO | WO 2006/028239 | 3/2006 |
| WO | WO 2006/058303 | 6/2006 |
| WO | WO 2007/077122 | 7/2007 |

OTHER PUBLICATIONS

Bymaster, F., "Xanomeline: A Selective Muscarinic Agonist for the Treatment of Alzheimer's Disease", Drug Development Research, 40 (1997), pp. 158-170.

Caufield, M.P., "International Union of Pharmacology. XVII. Classification of Muscarinic Acetylcholine Receptors", Pharmacol, Rev., 50 (1998), pp. 279-290.

Caufield, M.P., "Muscarinic Receptors-Characterization, Coupling and function", Pharmac. Ther., vol. 58 (1993), pp. 319-379.

Chambers, M., "Spiropiperidines as High-Affinity, Selective s Ligands", J. Med. Chem., 35(11) (1992), pp. 2033-2039.

Chiaverelli, S., "Ricerche nella serie della 4-feniipiperidina. Nota v. Derivati della 4,4'-spiro(1"metilpiperidin)-1,2,3,4,-tetraidroisochinolina", Gazzetta Chimica Italiana, 90, 189 (1960), CN1535967.

Custers, F., "Vesamicol and Some of its Derivatives: Questionable Ligands for Selectively Labelling Acetylcholine Transporters in Rat Brain", Eur, Jour. Of Pharm., 338 (1997), pp. 177-183.

deLaszlo, S., "A Nonpeptidic Agonist Ligand of the Human C5A Receptor: Synthesis, Binding Affinity Optimization and functional Characterization", Bioorganic and Medicinal Chem. Lett., 7(2) (1997), pp. 213-218.

Dhar, T.G., "Design and Synthesis of Novel a1a Adrenoceptor-Selective Antagonists. 2. Approaches to Eliminate Opioid Agonist Metabolites via Modification of Linker and 4-Methoxycarbonyl-4-phenylpiperidine Moiety1.2", J. Med, Chem, 42 (1999), pp. 4778-4793.

Efange S. "Comparative Tissue Distribution of conformationally Restricted Radioiodinated Vesamicol Receptor Ligands", Nuclear Medicine and Biology, 22(4) (1995), pp. 437-444.

Efange, S., "Molecular Determinants of Selectivity at the Vesamicol Receptor", Biochem, Phar., 49(6) (1995), pp. 791-797.

Efange, S., "N-Hydroxyalkyl Derivatives of 3β-Phenyltropane and Methylspiro[1H-indoline-3,4'-piperidine]: Vesamicol Analogues with Affinity or Monoamine Transporters", J. Med. Chem, 40 (1997), pp. 3905-3914.

Efange, S., "(+)-p-([18F]Fluorobenzyl)Spirotrozamicol {(+)-[18F]Spiro-FBT}: Synthesis and Biological Evaluation of a High-Affinity Ligand for the Vesicular Acetylcholine Transporter (VAChT)", Nuclear Medicine and Biology. vol. 26 (1999), pp. 189-192.

Efange, S., "Spirovesamicols: Conformationally Restricted Analogs of 2-(4-Phenylpiperidino)cyclohexanol (Vesamicol, AH5183) as Potential Modulators of Presynaptic Cholinergic Function", J. Med. Chem, 37 (1994), pp. 2574-2582.

Evans, B., "Orally Active, Nonpeptide Oxytocin Antagonists", J. Med. Chem., 35(21) (1992), pp. 3919-3927.

Felder, C., "Therapeutic Opportunities for Muscarinic Receptors in the Central Nervous System", J. Med. Chem.,43 (23) (2000), pp. 4333-4353.

Hulme, E.C., "Muscarinic Receptor Subtypes", Annu. Rev. Pharmacol. Toxicol., 30 (1990), pp. 633-673.

Kim, D., "Discovery of Human CCR5 Antagonists Containing Hydantoins for the Treatment of HIV-1 Infection", Bioorganic and Medicinal Chem. Lett., 11 (2001, pp. 3099-3102.

Malmstrom, R., "Pharmacology of H 394/84, a dihydropyridine neuropeptide Y Y1 Receptor Antagonist, in Vivo", Eur. Jour. of Pharm., 418 (2001), pp. 95-104.

Matier, W., "Novel Cyclizations and Ring-Opening Reactions of 3-Phenylindene Derivatives", J. Org. Chem., vol, 36, No. 5(1971), pp. 650-654.

Moltzen, E., "s Ligands with Subnanomolar Affinity and Preference for the s2 Binding Site. 2. Spiro-Joined Benzofuran, Isobenzofuran and Benzopyran Piperidines", J. Med. Chem., 38 (1995), pp. 2009-2017.

Morrow, D., "Synthesis of Some New 17-Spiro-Substituted Steroids", J. Med. Chem., 10(2) (1967), pp. 133-138.

Nargund, R., "Peptidomimetic Growth Hormone Secretagogues: Synthesis and Biological Activities of Analogs Varied at the Indole Nucleus of the Prototypical Spiropiperidine L-162,752", Bioorganic and Medicinal Chem. Lett., vol. 6, No. 14 (1996), pp. 1731-1736.

Nargund, R., "Synthesis and Biological Activities of Camphor-Based Non-Peptide Growth Hormone Secretagogues" Bioorganic and Medicinal Chem. Lett., vol. 6, No. 11 (1996), pp. 1265-1270.

Oprea, T., "Is There a Difference between Leads and Drugs? A Historical Perspective", J. Chem, Inf. Comput. Sci., 41 (2001), pp. 1308-1315.

Pasternak, A., "Potent, Orally Bioavailable Somatostatin Agonists: Good Absorption Achieved by Urea Backbone Cyclization", Bioorganic and Medicinal Chem. Lett., 9 (1999), pp. 491-496.

Patchett, A.A., "The Synthesis of 17β-Amino-17 a-(2'-carboxyethyl)androstane Lacatama1", J. Org. Chem, 27 (1962), pp. 3822-3828.

Pettibone, D,J., "Identification of an Orally Active, Nonpeptidyl Oxytocin Antagonist", Journal of Pharm. and Experimental Therap., 264(1) (1993), pp. 308-314.

Reimann, E., "Synthese und pharmakologische Prüfung Homologer und hydroxylierter 3,4-Dihydro-1'-methylspiro [naphthalin-(2H),4'-piperidine]", Archiv. Der. Pharmazie. VCH Verlagsgesellschaft MBH, Weinheim, DE, 323 (1990), pp. 35-39.

Takemoto, T., "Asymmetric Synthesis of Enantiomerically Pure Spiro[((2S)-hydroxy)indane-1,4'-piperidine]", Tetrahedron Asymmetry, 10 (1999), pp. 1787-1793.

Tata, J., "The Synthesis and Activity of Spiroindane Growth Hormone Secretagogues", Bioorganic and Medicinal Chem. Lett, 7(6) (1997), pp. 663-668.

Williams, P., "1-(((7.7-Dimethyl-2(S)-(2(S)-amino-4-(methylsulfonyl)butyramido)bicyclo[2.2.1]-heptan-1(S)-yl)methyl)sulfonyl)-4-2(2-methylphenyl)piperazine (L-368,899): An Orally Bioavailable, Non-Peptide Oxytocin Antagonist with Potential Utility for Managing Preterm Labor", J. Med. Chem, 37 (1994), pp. 555-571.

Yang, L., "Potent 3-Spiropiperidine Growth Hormone Secretagogues", Bioorganic and Medicinal Chem. Lett, 8(1) (1998), pp. 107-112.

Yang, L., "The Design and Synthesis of Non-Peptide Somatostatin Receptor Agonists", Proceedings of the American Peptide Symposium, 16th Minneapolis, MN, Jun. 26-Jul. 1,1999, (2000), meeting date 1999, 250-252.

Caufield, M.P., "International Union of Pharmacology. XVII. Classification of Muscarinic Acetylcholine Receptors ", Pharmacol. Rev., 50 (1998), pp. 279-290.

Hulme, E.C., "Muscarinic Receptor Subtypes", Annu. Rev, Pharmacol. Toxicol., 30 (1990), pp. 633-673.

Kim, D., "Discovery of Human CCR5 Antagonists Containing Hydantoins for the Treatment of HIV-1 Infection", Bioorganic and Medicinal Chem. Lett., 11 (2001, pp. 3099-3102.

Malmstrom, R., "Pharmacology of H 394/84, a dihydropyridine neuropeptide Y Y1 Receptor Antagonist. in Vivo", Eur. Jour. of Pharm., 418 (2001), pp. 95-104.

Matier, W., "Novel Cyclizations and Ring-Opening Reactions of 3-Phenylindene Derivatives", J. Org. Chem,. vol. 36, No. 5 (1971), pp. 650-654.

Moltzen, E., "s Ligands with Subnanomolar Affinity and Preference for the s2 Binding Site. 2. Spiro-Joined Benzofuran, Isobenzofuran and Benzopyran Piperidines", J. Med. Chem,. 38 (1995), pp. 2009-2017.

Morrow, D., "Synthesis of Some New 17-Spiro-Substituted Steroids", J. Med. Chem., 10(2) (1967), pp. 133-138.

Nargund, R., "Peptidomimetic Growth Hormone Secretagogues: Synthesis and Biological Activities of Analogs Varied at the Indole Nucleus of the Prototypical Spiropiperidine L-162,752", Bioorganic and Medicinal Chem. Lett., vol. 6, No, 14 (1996), pp. 1731-1736.

Nargund, R., "Synthesis and Biological Activities of Camphor-Based Non-Peptide Growth Hormone Secretagogues" Bioorganic and Medicinal Chem. Lett., vol. 6, No, 11 (1996), pp. 1265-1270.

Oprea, T., "Is There a Difference between Leads and Drugs? A Historical Perspective", J. Chem. Inf. Comput. Sci., 41 (2001), pp. 1308-1315.

Pasternak, A., "Potent, Orally Bioavailable Somatostatin Agonists: Good Absorption Achieved by Urea Backbone Cyclization", Bioorganic and Medicinal Chem. Lett., 9 (1999), pp. 491-496.

Patchett, A.A., "The Synthesis of 17β-Amino-17 a-(2'-carboxyethyl)androstane Lacatama1". J. Org. Chem, 27 (1962), pp. 3822-3828.

Pettibone, D.J., "Identification of an Orally Active, Nonpeptidyl Oxytocin Antagonist", Journal of Pharm. and Experimental Therap., 264(1) (1993), pp. 308-314.

Reimann, E., "Synthese und pharmakologische Prüfung Homologer und hydroxylierter 3,4-Dihydro-1'-methylspiro [naphthalin-(2H),4'-piperidiner]", Archiv. Der. Pharmazie, VCH Verlagsgesellschaft MBH, Weinheim, DE, 323 (1990), pp. 35-39.

Takemoto, T., "Asymmetric Synthesis of Enantiomerically Pure Spiro[((2S)-hydroxy)indane-1,4'-piperidine]", Tetrahedron Asymmetry, 10 (1999), pp. 1787-1793.

Tata, J., "The Synthesis and Activity of Spiroindane Growth Hormone Secretagogues", Bioorganic and Medicinal Chem. Lett, 7(6) (1997), pp. 663-668.

Williams, P., "1-(((7,7-Dimethyl-2(S)-(2(S)-amino-4-(methylsulfonyl)butyramido)bicyclo[2.2,1]-heptan-1(S)-yl)methyl)sulfonyl)-4-2(2-methylphenyl)piperazine (L-368,899): An Orally Bioavailable, Non-Peptide Oxytocin Antagonist with Potential Utility for Managing Preterm Labor", J. Med. Chem, 37 (1994), pp. 555-571.

Yang, L., "Potent 3-Spiropiperidine Growth Hormone Secretagogues", Bioorganic and Medicinal Chem. Lett, 8(1) (1998), pp. 107-112.

Yang, L., "The Design and Synthesis of Non-Peptide Somatostatin Receptor Agonists", Proceedings of the American Peptide Symposium, 16th Minneapolis, MN, Jun. 26-Jul. 1,1999, (2000), meeting date 1999, 250-252.

Cheng, Y., "Solid Phase Synthesis of Spiroindoline", Tet. Lett., 38 (1997), pp. 1497-1500.

Maligres, P. E., "Synthesis of the Orally Active Spiroindoline-Based Growth Hormone Secretagogue, MK-677", Tetrahedron, 53 (1997), pp. 10983-10992.

MODULATORS OF MUSCARINIC RECEPTORS

CLAIM OF PRIORITY

This application claims priority to U.S. Provisional Application Ser. No. 60/837,786 filed on Aug. 15, 2006, which is hereby incorporated by reference.

TECHNICAL FIELD OF THE INVENTION

The present invention relates to modulators of muscarinic receptors. The present invention also provides compositions comprising such modulators, and methods therewith for treating muscarinic receptor mediated diseases.

BACKGROUND OF THE INVENTION

The neurotransmitter acetylcholine binds to two types of cholinergic receptors: the ionotropic family of nicotinic receptors and the metabotropic family of muscarinic receptors. Muscarinic receptors belong to the large superfamily of plasma membrane-bound G protein coupled receptors (GPCRs). To date, five subtypes of muscarinic receptors ($M_1$-$M_5$) have been cloned and sequenced from a variety of species, and show a remarkably high degree of homology across species and receptor subtype. These $M_1$-$M_5$ muscarinic receptors are predominantly expressed within the parasympathetic nervous system which exerts excitatory and inhibitory control over the central and peripheral tissues and participate in a number of physiologic functions, including heart rate, arousal, cognition, sensory processing, and motor control.

Muscarinic agonists such as muscarine and pilocarpine, and antagonists, such as atropine have been known for over a century, but little progress has been made in the discovery of receptor subtype-selective compounds, thereby making it difficult to assign specific functions to the individual receptors. See, e.g., DeLapp, N. et al., "Therapeutic Opportunities for Muscarinic Receptors in the Central Nervous System," J. Med. Chem., 43(23), pp. 4333-4353 (2000); Hulme, E. C. et al., "Muscarinic Receptor Subtypes," Ann. Rev. Pharmacol. Toxicol., 30, pp. 633-673 (1990); Caulfield, M. P. et al., "Muscarinic Receptors-Characterization, Coupling, and Function," Pharmacol. Ther., 58, pp. 319-379 (1993); Caulfield, M. P. et al., International Union of Pharmacology. XVII. "Classification of Muscarinic Acetylcholine Receptors," Pharmacol. Rev., 50, pp. 279-290 (1998), the disclosures of which are incorporated herein by reference.

The Muscarinic family of receptors is the target of a large number of pharmacological agents used for various diseases, including leading drugs for COPD, asthma, urinary incontinence, glaucoma, Alzheimer's (AchE inhibitors). Despite the large therapeutic value of this family, cholinergic drugs are limited by the lack of selectivity of these agents, with significant activation of the parasympathetic autonomous system and elevated incidence of adverse effects. The molecular cloning of the muscarinic receptors and the identification of the physiological role of specific isoforms using knock-out mice, has recently delineated novel opportunities for selective muscarinic ligands, and has helped to define the selectivity profile that is required for enhanced efficacy and reduced side effects.

There is a need for modulators of muscarinic receptors $M_1$-$M_5$. There is also a need for methods for treating muscarinic receptor-mediated diseases.

There is also a need for modulators of muscarinic receptors that are selective as to subtypes $M_1$-$M_5$.

SUMMARY OF THE INVENTION

The present invention provides methods of modulating the activity of a muscarinic receptor (e.g., $M_1$, $M_2$, $M_3$, $M_4$, $M_5$, or combinations thereof) using compounds of formula I:

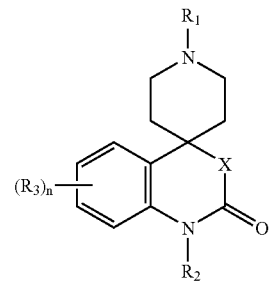

I or a pharmaceutically acceptable salt thereof, wherein $R_1$, $R_2$, $R_3$, X, and n are described below.

The present invention also provides compositions comprising compounds of formulae (I, Ia, Ib, Ic, and Id), and methods of treating muscarinic receptor mediated diseases using compounds of formulae (I, Ia, Ib, Ic, and Id).

DETAILED DESCRIPTION OF THE INVENTION

I. Definitions

For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

The term "muscarinic receptor," without a prefix specifying the receptor subtype, refers to one or more of the five receptor subtypes $M_1$-$M_5$.

The term "modulating" as used herein means increasing or decreasing, e.g. activity, by a measurable amount. Compounds that modulate muscarinic activity by increasing the activity of the muscarinic receptors are called agonists. Compounds that modulate muscarinic activity by decreasing the activity of the muscarinic receptors are called antagonists. An agonist interacts with a muscarinic receptor to increase the ability of the receptor to transduce an intracellular signal in response to endogenous ligand binding. An antagonist interacts with a muscarinic receptor and competes with the endogenous ligand(s) or substrate(s) for binding site(s) on the receptor to decrease the ability of the receptor to transduce an intracellular signal in response to endogenous ligand binding.

The phrase "treating or reducing the severity of a muscarinic receptor mediated disease" refers both to treatments for diseases that are directly caused by muscarinic activities and alleviation of symptoms of diseases not directly caused by muscarinic activities. Examples of diseases whose symptoms may be affected by muscarinic activity include, but are not limited to, CNS derived pathologies including cognitive disorders, Attention Deficit Hyperactivity Disorder (ADHD), obesity, Alzheimer's disease, various dementias such as vascular dementia, psychosis including schizophrenia, mania, bipolar disorders, pain conditions including acute and chronic syndromes, Huntington's Chorea, Friederich's ataxia, Gilles de la Tourette's Syndrome, Downs Syndrome, Pick disease, clinical depression, Parkinson's disease, peripheral disorders such as reduction of intra ocular pressure in Glaucoma and treatment of dry eyes and dry mouth including Sjögren's Syndrome, bradycardia, gastric acid secretion, asthma, GI disturbances and wound healing.

As described herein, compounds of the invention may optionally be substituted with one or more substituents, such as are illustrated generally above, or as exemplified by particular classes, subclasses, and species of the invention.

As used herein the term "aliphatic" encompasses the terms alkyl, alkenyl, alkynyl, each of which being optionally substituted as set forth below.

As used herein, an "alkyl" group refers to a saturated aliphatic hydrocarbon group containing 1-8 (e.g., 1-6 or 1-4) carbon atoms. An alkyl group can be straight or branched. Examples of alkyl groups include, but are not limited to, methyl, ethyl, propyl, isopropyl, butyl, isobutyl, sec-butyl, tert-butyl, n-pentyl, n-heptyl, or 2-ethylhexyl. An alkyl group can be substituted (i.e., optionally substituted) with one or more substituents such as halo, cycloaliphatic [e.g., cycloalkyl or cycloalkenyl], heterocycloaliphatic [e.g., heterocycloalkyl or heterocycloalkenyl], aryl, heteroaryl, alkoxy, aroyl, heteroaroyl, acyl [e.g., (aliphatic)carbonyl, (cycloaliphatic)carbonyl, or (heterocycloaliphatic)carbonyl], nitro, cyano, amido [e.g., (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino alkylaminocarbonyl, cycloalkylaminocarbonyl, heterocycloalkylaminocarbonyl, arylaminocarbonyl, or heteroarylaminocarbonyl], amino [e.g., aliphaticamino, cycloaliphaticamino, or heterocycloaliphaticamino], sulfonyl [e.g., aliphatic-$SO_2$—], sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroarylalkoxy, alkoxycarbonyl, alkylcarbonyloxy, or hydroxy. Without limitation, some examples of substituted alkyls include carboxyalkyl (such as HOOC-alkyl, alkoxycarbonylalkyl, and alkylcarbonyloxyalkyl), cyanoalkyl, hydroxyalkyl, alkoxyalkyl, acylalkyl, aralkyl, (alkoxyaryl)alkyl, (sulfonylamino)alkyl (such as (alkyl-$SO_2$-amino)alkyl), aminoalkyl, amidoalkyl, (cycloaliphatic)alkyl, or haloalkyl.

As used herein, an "alkenyl" group refers to an aliphatic carbon group that contains 2-8 (e.g., 2-6 or 2-4) carbon atoms and at least one double bond. Like an alkyl group, an alkenyl group can be straight or branched. Examples of an alkenyl group include, but are not limited to, allyl, isoprenyl, 2-butenyl, and 2-hexenyl. An alkenyl group can be optionally substituted with one or more substituents such as halo, cycloaliphatic [e.g., cycloalkyl or cycloalkenyl], heterocycloaliphatic [e.g., heterocycloalkyl or heterocycloalkenyl], aryl, heteroaryl, alkoxy, aroyl, heteroaroyl, acyl [e.g., (aliphatic)carbonyl, (cycloaliphatic)carbonyl, or (heterocycloaliphatic) carbonyl], nitro, cyano, amido [e.g., (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino alkylaminocarbonyl, cycloalkylaminocarbonyl, heterocycloalkylaminocarbonyl, arylaminocarbonyl, or heteroarylaminocarbonyl], amino [e.g., aliphaticamino, cycloaliphaticamino, heterocycloaliphaticamino, or aliphaticsulfonylamino], sulfonyl [e.g., alkyl-$SO_2$—, cycloaliphatic-$SO_2$—, or aryl-$SO_2$—], sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroaralkoxy, alkoxycarbonyl, alkylcarbonyloxy, or hydroxy. Without limitation, some examples of substituted alkenyls include cyanoalkenyl, alkoxyalkenyl, acylalkenyl, hydroxyalkenyl, aralkenyl, (alkoxyaryl)alkenyl, (sulfonylamino)alkenyl (such as (alkyl-$SO_2$-amino)alkenyl), aminoalkenyl, amidoalkenyl, (cycloaliphatic)alkenyl, or haloalkenyl.

As used herein, an "alkynyl" group refers to an aliphatic carbon group that contains 2-8 (e.g., 2-6 or 2-4) carbon atoms and has at least one triple bond. An alkynyl group can be straight or branched. Examples of an alkynyl group include, but are not limited to, propargyl and butynyl. An alkynyl group can be optionally substituted with one or more substituents such as aroyl, heteroaroyl, alkoxy, cycloalkyloxy, heterocycloalkyloxy, aryloxy, heteroaryloxy, aralkyloxy, nitro, carboxy, cyano, halo, hydroxy, sulfo, mercapto, sulfanyl [e.g., aliphaticsulfanyl or cycloaliphaticsulfanyl], sulfinyl [e.g., aliphaticsulfinyl or cycloaliphaticsulfinyl], sulfonyl [e.g., aliphatic-$SO_2$—, aliphaticamino-$SO_2$—, or cycloaliphatic-$SO_2$—], amido [e.g., aminocarbonyl, alkylaminocarbonyl, alkylcarbonylamino, cycloalkylaminocarbonyl, heterocycloalkylaminocarbonyl, cycloalkylcarbonylamino, arylaminocarbonyl, arylcarbonylamino, aralkylcarbonylamino, (heterocycloalkyl)carbonylamino, (cycloalkylalkyl)carbonylamino, heteroaralkylcarbonylamino, heteroarylcarbonylamino or heteroarylaminocarbonyl], urea, thiourea, sulfamoyl, sulfamide, alkoxycarbonyl, alkylcarbonyloxy, cycloaliphatic, heterocycloaliphatic, aryl, heteroaryl, acyl [e.g., (cycloaliphatic)carbonyl or (heterocycloaliphatic)carbonyl], amino [e.g., aliphaticamino], sulfoxy, oxo, carboxy, carbamoyl, (cycloaliphatic)oxy, (heterocycloaliphatic)oxy, or (heteroaryl)alkoxy.

As used herein, an "amido" encompasses both "aminocarbonyl" and "carbonylamino". These terms when used alone or in connection with another group refers to an amido group such as —N($R^X$)—C(O)—$R^Y$ or —C(O)—N($R^X$)$_2$, when used terminally, and —C(O)—N($R^X$)— or —N($R^X$)—C(O)—when used internally, wherein $R^X$ and $R^Y$ are defined below. Examples of amido groups include alkylamido (such as alkylcarbonylamino or alkylaminocarbonyl), (heterocycloaliphatic)amido, (heteroaralkyl)amido, (heteroaryl)amido, (heterocycloalkyl)alkylamido, arylamido, aralkylamido, (cycloalkyl)alkylamido, or cycloalkylamido.

As used herein, an "amino" group refers to —$NR^XR^Y$ wherein each of $R^X$ and $R^Y$ is independently hydrogen, aliphatic, cycloaliphatic, (cycloaliphatic)aliphatic, aryl, araliphatic, heterocycloaliphatic, (heterocycloaliphatic)aliphatic, heteroaryl, carboxy, sulfanyl, sulfinyl, sulfonyl, (aliphatic)carbonyl, (cycloaliphatic)carbonyl, ((cycloaliphatic)aliphatic)carbonyl, arylcarbonyl, (araliphatic)carbonyl, (heterocycloaliphatic)carbonyl, ((heterocycloaliphatic)aliphatic)carbonyl, (heteroaryl)carbonyl, or (heteroaraliphatic) carbonyl, each of which being defined herein and being optionally substituted. Examples of amino groups include alkylamino, dialkylamino, or arylamino. When the term "amino" is not the terminal group (e.g., alkylcarbonylamino), it is represented by —$NR^X$—. $R^X$ has the same meaning as defined above.

As used herein, an "aryl" group used alone or as part of a larger moiety as in "aralkyl", "aralkoxy", or "aryloxyalkyl" refers to monocyclic (e.g., phenyl); bicyclic (e.g., indenyl, naphthalenyl, tetrahydronaphthyl, tetrahydroindenyl); and tricyclic (e.g., fluorenyl tetrahydrofluorenyl, or tetrahydroanthracenyl, anthracenyl) ring systems in which the monocyclic ring system is aromatic or at least one of the rings in a bicyclic or tricyclic ring system is aromatic. The bicyclic and tricyclic groups include benzofused 2-3 membered carbocyclic rings. For example, a benzofused group includes phenyl fused with two or more $C_{4-8}$ carbocyclic moieties. An aryl is optionally substituted with one or more substituents including aliphatic [e.g., alkyl, alkenyl, or alkynyl]; cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic)oxy; aryloxy; heteroaryloxy; (araliphatic)oxy; (heteroaraliphatic)oxy; aroyl; heteroaroyl; amino; oxo (on a non-aromatic carbocyclic ring of a benzofused bicyclic or tricyclic aryl); nitro; carboxy; amido; acyl [e.g., aliphaticcarbonyl; (cycloaliphatic)carbonyl; ((cycloaliphatic)aliphatic)carbonyl; (araliphatic)carbonyl; (heterocycloaliphatic)carbonyl; ((heterocycloaliphatic)aliphatic)carbonyl; or (heteroaraliphatic)carbonyl]; sulfonyl [e.g., aliphatic-$SO_2$— or amino-$SO_2$—]; sulfinyl [e.g., aliphatic-S(O)— or cycloaliphatic-S(O)—]; sulfanyl [e.g., aliphatic-S—]; cyano; halo; hydroxy; mercapto; sulfoxy; urea; thiourea; sulfamoyl; sulfamide; or carbamoyl. Alternatively, an aryl can be unsubstituted.

Non-limiting examples of substituted aryls include haloaryl [e.g., mono-, di (such as p,m-dihaloaryl), and (trihalo)aryl]; (carboxy)aryl [e.g., (alkoxycarbonyl)aryl, ((aralkyl)carbonyloxy)aryl, and (alkoxycarbonyl)aryl]; (amido)aryl [e.g., (aminocarbonyl)aryl, (((alkylamino)alkyl)aminocarbonyl)aryl, (alkylcarbonyl)aminoaryl, (arylaminocarbonyl)aryl, and (((heteroaryl)amino)carbonyl)aryl]; aminoaryl [e.g., ((alkylsulfonyl)amino)aryl or ((dialkyl)amino)aryl]; (cyanoalkyl)aryl; (alkoxy)aryl; (sulfamoyl)aryl [e.g., (aminosulfonyl)aryl]; (alkylsulfonyl)aryl; (cyano)aryl; (hydroxyalkyl)aryl; ((alkoxy)alkyl)aryl; (hydroxy)aryl, ((carboxy)alkyl)aryl; (((dialkyl)amino)alkyl)aryl; (nitroalkyl)aryl; (((alkylsulfonyl)amino)alkyl)aryl; ((heterocycloaliphatic)carbonyl)aryl; ((alkylsulfonyl)alkyl)aryl; (cyanoalkyl)aryl; (hydroxyalkyl)aryl; (alkylcarbonyl)aryl; alkylaryl; (trihaloalkyl)aryl; p-amino-m-alkoxycarbonylaryl; p-amino-m-cyanoaryl; p-halo-m-aminoaryl; or (m-(heterocycloaliphatic)-o-(alkyl))aryl.

As used herein, an "araliphatic" such as an "aralkyl" group refers to an aliphatic group (e.g., a $C_{1-4}$ alkyl group) that is substituted with an aryl group. "Aliphatic," "alkyl," and "aryl" are defined herein. An example of an araliphatic such as an aralkyl group is benzyl.

As used herein, an "aralkyl" group refers to an alkyl group (e.g., a $C_{1-4}$ alkyl group) that is substituted with an aryl group. Both "alkyl" and "aryl" have been defined above. An example of an aralkyl group is benzyl. An aralkyl is optionally substituted with one or more substituents such as aliphatic [e.g., alkyl, alkenyl, or alkynyl, including carboxyalkyl, hydroxyalkyl, or haloalkyl such as trifluoromethyl], cycloaliphatic [e.g., cycloalkyl or cycloalkenyl], (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, amido [e.g., aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, or heteroaralkylcarbonylamino], cyano, halo, hydroxy, acyl, mercapto, alkylsulfanyl, sulfoxy, urea, thiourea, sulfamoyl, sulfamide, oxo, or carbamoyl.

As used herein, a "bicyclic ring system" includes 8-12 (e.g., 9, 10, or 11) membered structures that form two rings, wherein the two rings have at least one atom in common (e.g., 2 atoms in common). Bicyclic ring systems include bicycloaliphatics (e.g., bicycloalkyl or bicycloalkenyl), bicycloheteroaliphatics, bicyclic aryls, and bicyclic heteroaryls.

As used herein, a "cycloaliphatic" group encompasses a "cycloalkyl" group and a "cycloalkenyl" group, each of which being optionally substituted as set forth below.

As used herein, a "cycloalkyl" group refers to a saturated carbocyclic mono- or bicyclic (fused or bridged) ring of 3-10 (e.g., 5-10) carbon atoms. Examples of cycloalkyl groups include cyclopropyl, cyclobutyl, cyclopentyl, cyclohexyl, cycloheptyl, adamantyl, norbornyl, cubyl, octahydro-indenyl, decahydro-naphthyl, bicyclo[3.2.1]octyl, bicyclo[2.2.2]octyl, bicyclo[3.3.1]nonyl, bicyclo[3.3.2.]decyl, bicyclo[2.2.2]octyl, adamantyl, azacycloalkyl, or ((aminocarbonyl)cycloalkyl)cycloalkyl. A "cycloalkenyl" group, as used herein, refers to a non-aromatic carbocyclic ring of 3-10 (e.g., 4-8) carbon atoms having one or more double bonds. Examples of cycloalkenyl groups include cyclopentenyl, 1,4-cyclohexa-di-enyl, cycloheptenyl, cyclooctenyl, hexahydro-indenyl, octahydro-naphthyl, cyclohexenyl, cyclopentenyl, bicyclo[2.2.2]octenyl, or bicyclo[3.3.1]nonenyl. A cycloalkyl or cycloalkenyl group can be optionally substituted with one or more substituents such as aliphatic [e.g., alkyl, alkenyl, or alkynyl], cycloaliphatic, (cycloaliphatic) aliphatic, heterocycloaliphatic, (heterocycloaliphatic) aliphatic, aryl, heteroaryl, alkoxy, (cycloaliphatic)oxy, (heterocycloaliphatic)oxy, aryloxy, heteroaryloxy, (araliphatic)oxy, (heteroaraliphatic)oxy, aroyl, heteroaroyl, amino, amido [e.g., (aliphatic)carbonylamino, (cycloaliphatic)carbonylamino, ((cycloaliphatic)aliphatic)carbonylamino, (aryl)carbonylamino, (araliphatic)carbonylamino, (heterocycloaliphatic)carbonylamino, ((heterocycloaliphatic)aliphatic)carbonylamino, (heteroaryl)carbonylamino, or (heteroaraliphatic)carbonylamino], nitro, carboxy [e.g., HOOC—, alkoxycarbonyl, or alkylcarbonyloxy], acyl [e.g., (cycloaliphatic)carbonyl, ((cycloaliphatic) aliphatic)carbonyl, (araliphatic)carbonyl, (heterocycloaliphatic)carbonyl, ((heterocycloaliphatic)aliphatic)carbonyl, or (heteroaraliphatic)carbonyl], cyano, halo, hydroxy, mercapto, sulfonyl [e.g., alkyl-$SO_2$— and aryl-$SO_2$—], sulfinyl [e.g., alkyl-S(O)—], sulfanyl [e.g., alkyl-S—], sulfoxy, urea, thiourea, sulfamoyl, sulfamide, oxo, or carbamoyl.

As used herein, "cyclic moiety" includes cycloaliphatic, heterocycloaliphatic, aryl, or heteroaryl, each of which has been defined previously.

As used herein, the term "heterocycloaliphatic" encompasses a heterocycloalkyl group and a heterocycloalkenyl group, each of which being optionally substituted as set forth below.

As used herein, a "heterocycloalkyl" group refers to a 3-10 membered mono- or bicylic (fused or bridged) (e.g., 5- to 10-membered mono- or bicyclic) saturated ring structure, in which one or more of the ring atoms is a heteroatom (e.g., N, O, S, or combinations thereof). Examples of a heterocycloalkyl group include piperidyl, piperazyl, tetrahydropyranyl, tetrahydrofuryl, 1,4-dioxolanyl, 1,4-dithianyl, 1,3-dioxolanyl, oxazolidyl, isoxazolidyl, morpholinyl, thiomorpholyl, octahydrobenzofuryl, octahydrochromenyl, octahydrothiochromenyl, octahydroindolyl, octahydropyrindinyl, decahydroquinolinyl, octahydrobenzo[b]thiopheneyl, 2-oxa-bicyclo[2.2.2]octyl, 1-aza-bicyclo[2.2.2]octyl, 3-aza-bicyclo[3.2.1]octyl, anad 2,6-dioxa-tricyclo[3.3.1.0$^{3,7}$]nonyl. A monocyclic heterocycloalkyl group can be fused with a phenyl moiety such as tetrahydroisoquinoline. A "heterocycloalkenyl" group, as used herein, refers to a mono- or bicylic (e.g., 5- to 10-membered mono- or bicyclic)

non-aromatic ring structure having one or more double bonds, and wherein one or more of the ring atoms is a heteroatom (e.g., N, O, or S). Monocyclic and bicycloheteroaliphatics are numbered according to standard chemical nomenclature.

A heterocycloalkyl or heterocycloalkenyl group can be optionally substituted with one or more substituents such as aliphatic [e.g., alkyl, alkenyl, or alkynyl], cycloaliphatic, (cycloaliphatic)aliphatic, heterocycloaliphatic, (heterocycloaliphatic)aliphatic, aryl, heteroaryl, alkoxy, (cycloaliphatic)oxy, (heterocycloaliphatic)oxy, aryloxy, heteroaryloxy, (araliphatic)oxy, (heteroaraliphatic)oxy, aroyl, heteroaroyl, amino, amido [e.g., (aliphatic)carbonylamino, (cycloaliphatic)carbonylamino, ((cycloaliphatic) aliphatic)carbonylamino, (aryl)carbonylamino, (araliphatic) carbonylamino, (heterocycloaliphatic)carbonylamino, ((heterocycloaliphatic) aliphatic)carbonylamino, (heteroaryl)carbonylamino, or (heteroaraliphatic)carbonylamino], nitro, carboxy [e.g., HOOC—, alkoxycarbonyl, or alkylcarbonyloxy], acyl [e.g., (cycloaliphatic)carbonyl, ((cycloaliphatic) aliphatic)carbonyl, (araliphatic)carbonyl, (heterocycloaliphatic)carbonyl, ((heterocycloaliphatic)aliphatic) carbonyl, or (heteroaraliphatic)carbonyl], nitro, cyano, halo, hydroxy, mercapto, sulfonyl [e.g., alkylsulfonyl or arylsulfonyl], sulfinyl [e.g., alkylsulfinyl], sulfanyl [e.g., alkylsulfanyl], sulfoxy, urea, thiourea, sulfamoyl, sulfamide, oxo, or carbamoyl.

A "heteroaryl" group, as used herein, refers to a monocyclic, bicyclic, or tricyclic ring system having 4 to 15 ring atoms wherein one or more of the ring atoms is a heteroatom (e.g., N, O, S, or combinations thereof) and in which the monocyclic ring system is aromatic or at least one of the rings in the bicyclic or tricyclic ring systems is aromatic. A heteroaryl group includes a benzofused ring system having 2 to 3 rings. For example, a benzofused group includes benzo fused with one or two 4 to 8 membered heterocycloaliphatic moieties (e.g., indolizyl, indolyl, isoindolyl, 3H-indolyl, indolinyl, benzo[b]furyl, benzo[b]thiophenyl, quinolinyl, or isoquinolinyl). Some examples of heteroaryl are azetidinyl, pyridyl, 1H-indazolyl, furyl, pyrrolyl, thienyl, thiazolyl, oxazolyl, imidazolyl, tetrazolyl, benzofuryl, isoquinolinyl, benzthiazolyl, xanthene, thioxanthene, phenothiazine, dihydroindole, benzo[1,3]dioxole, benzo[b]furyl, benzo[b]thiophenyl, indazolyl, benzimidazolyl, benzthiazolyl, puryl, cinnolyl, quinolyl, quinazolyl, cinnolyl, phthalazyl, quinazolyl, quinoxalyl, isoquinolyl, 4H-quinolizyl, benzo-1, 2,5-thiadiazolyl, or 1,8-naphthyridyl.

Without limitation, monocyclic heteroaryls include furyl, thiophenyl, 2H-pyrrolyl, pyrrolyl, oxazolyl, thazolyl, imidazolyl, pyrazolyl, isoxazolyl, isothiazolyl, 1,3,4-thiadiazolyl, 2H-pyranyl, 4-H-pranyl, pyridyl, pyridazyl, pyrimidyl, pyrazolyl, pyrazyl, or 1,3,5-triazyl. Monocyclic heteroaryls are numbered according to standard chemical nomenclature.

Without limitation, bicyclic heteroaryls include indolizyl, indolyl, isoindolyl, 3H-indolyl, indolinyl, benzo[b]furyl, benzo[b]thiophenyl, quinolinyl, isoquinolinyl, indolizyl, isoindolyl, indolyl, benzo[b]furyl, bexo[b]thiophenyl, indazolyl, benzimadazyl, benzthiazolyl, purinyl, 4H-quinolizyl, quinolyl, isoquinolyl, cinnolyl, phthalazyl, quinazolyl, quinoxalyl, 1,8-naphthyridyl, or pteridyl. Bicyclic heteroaryls are numbered according to standard chemical nomenclature.

A heteroaryl is optionally substituted with one or more substituents such as aliphatic [e.g., alkyl, alkenyl, or alkynyl]; cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic) oxy; aryloxy; heteroaryloxy; (araliphatic)oxy; (heteroaraliphatic)oxy; aroyl; heteroaroyl; amino; oxo (on a non-aromatic carbocyclic or heterocyclic ring of a bicyclic or tricyclic heteroaryl); carboxy; amido; acyl [e.g., aliphaticcarbonyl; (cycloaliphatic)carbonyl; ((cycloaliphatic)aliphatic) carbonyl; (araliphatic)carbonyl; (heterocycloaliphatic)carbonyl; ((heterocycloaliphatic)aliphatic)carbonyl; or (heteroaraliphatic)carbonyl]; sulfonyl [e.g., aliphaticsulfonyl or aminosulfonyl]; sulfinyl [e.g., aliphaticsulfinyl]; sulfanyl [e.g., aliphaticsulfanyl]; nitro; cyano; halo; hydroxy; mercapto; sulfoxy; urea; thiourea; sulfamoyl; sulfamide; or carbamoyl. Alternatively, a heteroaryl can be unsubstituted.

Non-limiting examples of substituted heteroaryls include (halo)heteroaryl [e.g., mono- and di-(halo)heteroaryl]; (carboxy)heteroaryl [e.g., (alkoxycarbonyl)heteroaryl]; cyanoheteroaryl; aminoheteroaryl [e.g., ((alkylsulfonyl)amino)heteroaryl and ((dialkyl)amino)heteroaryl]; (amido)heteroaryl [e.g., aminocarbonylheteroaryl, ((alkylcarbonyl)amino)heteroaryl, ((((alkyl)amino)alkyl)aminocarbonyl)heteroaryl, (((heteroaryl)amino)carbonyl)heteroaryl, ((heterocycloaliphatic)carbonyl)heteroaryl, and ((alkylcarbonyl) amino)heteroaryl]; (cyanoalkyl)heteroaryl; (alkoxy)heteroaryl; (sulfamoyl)heteroaryl [e.g., (aminosulfonyl) heteroaryl]; (sulfonyl)heteroaryl [e.g., (alkylsulfonyl) heteroaryl]; (hydroxyalkyl)heteroaryl; (alkoxyalkyl) heteroaryl; (hydroxy)heteroaryl; ((carboxy)alkyl)heteroaryl; (((dialkyl)amino)alkyl]heteroaryl; (heterocycloaliphatic) heteroaryl; (cycloaliphatic)heteroaryl; (nitroalkyl)heteroaryl; (((alkylsulfonyl)amino)alkyl)heteroaryl; ((alkylsulfonyl)alkyl)heteroaryl; (cyanoalkyl)heteroaryl; (acyl) heteroaryl [e.g., (alkylcarbonyl)heteroaryl]; (alkyl) heteroaryl, and (haloalkyl)heteroaryl [e.g., trihaloalkylheteroaryl].

A "heteroaraliphatic (such as a heteroalkyl group) as used herein, refers to an aliphatic group (e.g., a $C_{1-4}$ alkyl group) that is substituted with a heteroaryl group. "Aliphatic," "alkyl," and "heteroaryl" have been defined above.

A "heteroaralkyl" group, as used herein, refers to an alkyl group (e.g., a $C_{1-4}$ alkyl group) that is substituted with a heteroaryl group. Both "alkyl" and "heteroaryl" have been defined above. A heteroaralkyl is optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, an "acyl" group refers to a formyl group or $R^X$—C(O)— (such as alkyl-C(O)—, also referred to as "alkylcarbonyl") where $R^X$ and "alkyl" have been defined previously. Acetyl and pivaloyl are examples of acyl groups.

As used herein, an "aroyl" or "heteroaroyl" refers to an aryl-C(O)— or a heteroaryl-C(O)—. The aryl and heteroaryl portion of the aroyl or heteroaroyl is optionally substituted as previously defined.

As used herein, an "alkoxy" group refers to an alkyl-O— group where "alkyl" has been defined previously.

As used herein, a "carbamoyl" group refers to a group having the structure —O—CO—NR$^X$R$^Y$ or —NR$^X$—CO—

O—$R^Z$ wherein $R^X$ and $R^Y$ have been defined above and $R^Z$ can be aliphatic, aryl, araliphatic, heterocycloaliphatic, heteroaryl, or heteroaraliphatic.

As used herein, a "carboxy" group refers to —COOH, —COO$R^X$, —OC(O)H, —OC(O)$R^X$ when used as a terminal group; or —OC(O)— or —C(O)O— when used as an internal group.

As used herein, a "haloaliphatic" group refers to an aliphatic group substituted with 1-3 halogen. For instance, the term haloalkyl includes the group —$CF_3$.

As used herein, a "mercapto" group refers to —SH.

As used herein, a "sulfo" group refers to —$SO_3H$ or —$SO_3R^X$ when used terminally or —S(O)$_3$— when used internally.

As used herein, a "sulfamide" group refers to the structure —$NR^X$—S(O)$_2$—$NR^YR^Z$ when used terminally and —$NR^X$—S(O)$_2$—$NR^Y$— when used internally, wherein $R^X$, $R^Y$, and $R^Z$ have been defined above.

As used herein, a "sulfonamide" group refers to the structure —S(O)$_2$—$NR^XR^Y$ or —$NR^X$—S(O)$_2$—$R^Z$ when used terminally; or —S(O)$_2$—$NR^X$— or —$NR^X$—S(O)$_2$— when used internally, wherein $R^X$, $R^Y$, and $R^Z$ are defined above.

As used herein a "sulfanyl" group refers to —S—$R^X$ when used terminally and —S— when used internally, wherein $R^X$ has been defined above. Examples of sulfanyls include aliphatic-S—, cycloaliphatic-S—, aryl-S—, or the like.

As used herein a "sulfinyl" group refers to —S(O)—$R^X$ when used terminally and —S(O)—when used internally, wherein $R^X$ has been defined above. Exemplary sulfinyl groups include aliphatic-S(O)—, aryl-S(O)—, (cycloaliphatic(aliphatic))-S(O)—, cycloalkyl-S(O)—, heterocycloaliphatic-S(O)—, heteroaryl-S(O)—, or the like.

As used herein, a "sulfonyl" group refers to —S(O)$_2$—$R^X$ when used terminally and —S(O)$_2$— when used internally, wherein $R^X$ has been defined above. Exemplary sulfonyl groups include aliphatic-S(O)$_2$—, aryl-S(O)$_2$—, (cycloaliphatic(aliphatic))-S(O)$_2$—, cycloaliphatic-S(O)$_2$—, heterocycloaliphatic-S(O)$_2$—, heteroaryl-S(O)$_2$—, (cycloaliphatic(amido(aliphatic)))-S(O)$_2$— or the like.

As used herein, a "sulfoxy" group refers to —O—SO—$R^X$ or —SO—O—$R^X$, when used terminally and —O—S(O)— or —S(O)—O— when used internally, where $R^X$ has been defined above.

As used herein, a "halogen" or "halo" group refers to fluorine, chlorine, bromine or iodine.

As used herein, an "alkoxycarbonyl," which is encompassed by the term carboxy, used alone or in connection with another group refers to a group such as alkyl-O—C(O)—.

As used herein, an "alkoxyalkyl" refers to an alkyl group such as alkyl-O-alkyl-, wherein alkyl has been defined above.

As used herein, a "carbonyl" refer to —C(O)—.

As used herein, an "oxo" refers to =O.

As used herein, an "aminoalkyl" refers to the structure ($R^X$)$_2$N-alkyl-.

As used herein, a "cyanoalkyl" refers to the structure (NC)-alkyl-.

As used herein, a "urea" group refers to the structure —$NR^X$—CO—$NR^YR^Z$ and a "thiourea" group refers to the structure —$NR^X$—CS—$NR^YR^Z$ when used terminally and —$NR^X$—CO—$NR^Y$— or —$NR^X$—CS—$NR^Y$— when used internally, wherein $R^X$, $R^Y$, and $R^Z$ have been defined above.

As used herein, a "guanidine" group refers to the structure —N=C(N($R^XR^Y$))N($R^XR^Y$) or —$NR^X$—C(=$NR^X$)$NR^XR^Y$ wherein $R^X$ and $R^Y$ have been defined above.

As used herein, the term "amidino" group refers to the structure —C=($NR^X$)N($R^XR^Y$) wherein $R^X$ and $R^Y$ have been defined above.

In general, the term "vicinal" refers to the placement of substituents on a group that includes two or more carbon atoms, wherein the substituents are attached to adjacent carbon atoms.

In general, the term "geminal" refers to the placement of substituents on a group that includes two or more carbon atoms, wherein the substituents are attached to the same carbon atom.

The terms "terminally" and "internally" refer to the location of a group within a substituent. A group is terminal when the group is present at the end of the substituent not further bonded to the rest of the chemical structure. Carboxyalkyl, i.e., $R^X$O(O)C-alkyl is an example of a carboxy group used terminally. A group is internal when the group is present in the middle of a substituent to at the end of the substituent bound to the rest of the chemical structure. Alkylcarboxy (e.g., alkyl-C(O)O— or alkyl-OC(O)—) and alkylcarboxyaryl (e.g., alkyl-C(O)O-aryl- or alkyl-O(CO)-aryl-) are examples of carboxy groups used internally.

As used herein, "cyclic group" includes mono-, bi-, and tri-cyclic ring systems including cycloaliphatic, heterocycloaliphatic, aryl, or heteroaryl, each of which has been previously defined.

As used herein, a "bridged bicyclic ring system" refers to a bicyclic heterocyclicalipahtic ring system or bicyclic cycloaliphatic ring system in which the rings are bridged. Examples of bridged bicyclic ring systems include, but are not limited to, adamantanyl, norbornanyl, bicyclo[3.2.1]octyl, bicyclo[2.2.2]octyl, bicyclo[3.3.1]nonyl, bicyclo[3.2.3]nonyl, 2-oxabicyclo[2.2.2]octyl, 1-azabicyclo[2.2.2]octyl, 3-azabicyclo[3.2.1]octyl, and 2,6-dioxa-tricyclo[3.3.1.0$^{3,7}$]nonyl. A bridged bicyclic ring system can be optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, an "aliphatic chain" refers to a branched or straight aliphatic group (e.g., alkyl groups, alkenyl groups, or alkynyl groups). A straight aliphatic chain has the structure —[$CH_2$]$_v$—, where v is 1-6. A branched aliphatic chain is a straight aliphatic chain that is substituted with one or more aliphatic groups. A branched aliphatic chain has the structure —[CHQ]$_v$— or —[CQQ]$_v$— where Q is hydrogen or an aliphatic group; however, Q shall be an aliphatic group in at least one instance. The term aliphatic chain includes alkyl chains, alkenyl chains, and alkynyl chains, where alkyl, alkenyl, and alkynyl are defined above.

The phrase "optionally substituted" is used interchangeably with the phrase "substituted or unsubstituted." As described herein, compounds of the invention can optionally be substituted with one or more substituents, such as are illustrated generally above, or as exemplified by particular classes, subclasses, and species of the invention. As described herein, the variables in formulae (I, Ia, and Ib), e.g., $R_1$, $R_2$, and $R_3$, and other variables contained therein encompass specific groups, such as alkyl and aryl. Unless otherwise noted, each of the specific groups for the variables $R_1$, $R_2$, and $R_3$, and other variables contained therein can be optionally substituted with one or more substituents described herein. Each substituent of a specific group is further optionally substituted with one to three of halo, cyano, oxo, alkoxy, hydroxy, amino, nitro, aryl, haloalkyl, and alkyl. For instance, an alkyl group can be substituted with alkylsulfanyl and the alkylsulfanyl can be optionally substituted with one to three of halo, cyano, oxo, alkoxy, hydroxy, amino, nitro, aryl, haloalkyl, and alkyl. As an additional example, the cycloalkyl portion of a (cycloalkyl)carbonylamino can be optionally substituted with one to three of halo, cyano, alkoxy, hydroxy, nitro, haloalkyl, and alkyl. When two alkoxy groups are bound to the same atom or adjacent atoms, the two alkxoy groups can form a ring together with the atom(s) to which they are bound.

In general, the term "substituted," whether preceded by the term "optionally" or not, refers to the replacement of hydrogen radicals in a given structure with the radical of a specified substituent. Specific substituents are described above in the definitions and below in the description of compounds and examples thereof. Unless otherwise indicated, an optionally substituted group can have a substituent at each substitutable position of the group, and when more than one position in any given structure can be substituted with more than one substituent selected from a specified group, the substituent can be either the same or different at every position. A ring substituent, such as a heterocycloalkyl, can be bound to another ring, such as a cycloalkyl, to form a spiro-bicyclic ring system, e.g., both rings share one common atom. As one of ordinary skill in the art will recognize, combinations of substituents envisioned by this invention are those combinations that result in the formation of stable or chemically feasible compounds.

The phrase "stable or chemically feasible," as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

As used herein, an effective amount is defined as the amount required to confer a therapeutic effect on the treated patient, and is typically determined based on age, surface area, weight, and condition of the patient. The interrelationship of dosages for animals and humans (based on milligrams per meter squared of body surface) is described by Freireich et al., Cancer Chemother. Rep., 50: 219 (1966). Body surface area may be approximately determined from height and weight of the patient. See, e.g., Scientific Tables, Geigy Pharmaceuticals, Ardsley, N.Y., 537 (1970). As used herein, "patient" refers to a mammal, including a human. Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, (Z) and (E) conformational isomers, and tautomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$- or $^{14}C$-enriched carbon are within the scope of this invention. Such compounds are useful, for example, as analytical tools or probes in biological assays.

II. Compounds

Compounds of formula I are useful modulators of muscarinic receptor activity

A. Generic Compounds:

Compounds of the present invention include:

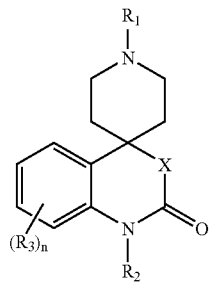

I or a pharmaceutically acceptable salt thereof.

X is —$NR_{50}$— or —O—, wherein $R_{50}$ is independently hydrogen or an optionally substituted $C_{1-6}$ aliphatic.

$R_1$ is an optionally substituted aliphatic, an optionally substituted cycloaliphatic, or an optionally substituted heterocycloaliphatic.

$R_2$ is —$Z^B R_5$, wherein each $Z^B$ is independently a bond or an optionally substituted branched or straight $C_{1-6}$ aliphatic chain wherein up to two carbon units of $Z^B$ are optionally and independently replaced by —CO—, —CS—, —$CONR^B$—, —$CONR^B NR^B$—, —$CO_2$—, —OCO—, —$NR^B CO_2$—, —O—, —$NR^B CONR^B$—, —$OCONR^B$—, —$NR^B NR^B$—, —$NR^B CO$—, —S—, —SO—, —$SO_2$—, —$NR^B$—, —$SO_2 NR^B$—, —$NR^B SO_2$—, or —$NR^B SO_2 NR^B$—; each $R_5$ is independently $R^B$, halo, —OH, —$NH_2$, —$NO_2$, —CN, or —$OCF_3$; and each $R^B$ is independently hydrogen, an optionally substituted $C_{1-4}$ aliphatic, an optionally substituted cycloaliphatic, an optionally substituted heterocycloaliphatic, an optionally substituted aryl, or an optionally substituted heteroaryl.

Each $R_3$ is independently hydrogen, halo, nitro, cyano, hydroxy, optionally substituted aliphatic, optionally substituted (aliphatic)oxy, optionally substituted cycloaliphatic, optionally substituted heterocycloaliphatic, optionally substituted aryl, or optionally substituted heteroaryl.

n is 0-4.

B. Specific Embodiments

1. Substituent $R_1$ $R_1$ is an optionally substituted aliphatic, an optionally substituted cycloaliphatic, or an optionally substituted heterocycloaliphatic.

In several embodiments, $R_1$ is independently —$Z^A R_4$, wherein each $Z^A$ is independently a bond or an optionally substituted branched or straight $C_{1-12}$ aliphatic chain wherein up to two carbon units of $Z^A$ are optionally and independently replaced by —CO—, —CS—, —$CONR^A$—, —$CONR^A NR^A$—, —$CO_2$—, —OCO—, —$NR^A CO_2$—, —O—, —$NR^A CONR^A$—, —$OCONR^A$—, —$NR^A NR^A$—, —$NR^A CO$—, —S—, —$SO_2$—, —$NR^A$—, —$SO_2 NR^A$—, —$NR^A SO_2$, or —$NR^A SO_2 NR^A$—; each $R_4$ is independently $R^A$, halo, —OH, —$NH_2$, —$NO_2$, —CN, or —$OCF_3$; and each $R^A$ is independently hydrogen, optionally substituted $C_{1-8}$ aliphatic group, optionally substituted cycloaliphatic, optionally substituted heterocycloaliphatic, optionally substituted aryl, or optionally substituted heteraryl. However, when $Z^A$ is a bond and $R_4$ is $R^A$, then $R^A$ is optionally substituted aliphatic, optionally substituted cycloaliphatic, or optionally substituted heterocycloaliphatic.

In several embodiments, $R_1$ is independently —$Z^AR_4$, wherein each $Z^A$ is independently a bond or an optionally substituted branched or straight $C_{1-6}$ aliphatic chain wherein up to two carbon units of $Z^A$ are optionally and independently replaced by —CO—, —CS—, —CONR$^A$—, —CONR$^A$NR$^A$—, —CO$_2$—, —OCO—, —NR$^A$CO$_2$—, —O—, —NR$^A$CONR$^A$, —OCONR$^A$—, —NR$^A$NR$^A$—, —NR$^A$CO—, —S—, —SO—, —SO$_2$—, —NR$^A$—, —SO$_2$NR$^A$—, —NR$^A$SO$_2$—, or —NR$^A$SO$_2$NR$^A$—; each $R_4$ is independently $R^A$, halo, —OH, —NH$_2$, —NO$_2$, —CN, or —OCF$_3$; and each $R^A$ is independently hydrogen, optionally substituted $C_{1-6}$ aliphatic group, optionally substituted cycloaliphatic, or optionally substituted heterocycloaliphatic. However, when $Z^A$ is a bond and $R_4$ is $R^A$, then $R^A$ is optionally substituted aliphatic, optionally substituted cycloaliphatic, or optionally substituted heterocycloaliphatic.

In several alternative embodiments, $R_1$ is optionally substituted cycloaliphatic. For example, $R_1$ is monocyclic, bicyclic, or tricyclic cycloaliphatic, each of which is optionally substituted.

In several examples, $R_1$ is optionally substituted 3-8 membered monocyclic cycloaliphatic that is optionally substituted with 1-3 of halo, oxo, hydroxy, nitro, cyano, or optionally substituted aliphatic, optionally substituted oxime (e.g., (aliphatic(oxy))imino), optionally substituted (aliphatic)oxy, optionally substituted carboxy (e.g., (aliphatic(oxy))carbonyl), optionally substituted cycloaliphatic, optionally substituted heterocycloaliphatic, optionally substituted aryl, optionally substituted heteroaryl, or combinations thereof. For instance, $R_1$ is cyclopropyl, cyclobutyl, cyclopentyl, cyclohexyl, cycloheptyl, or cyclooctyl, each of which is optionally substituted with 1-3 of halo, hydroxy, nitro, cyano, aliphatic, oxime (e.g., aliphatic(oxy)imino or (aralkyl(oxy)) imino), (aliphatic)carbonyl, (aliphatic)oxy, carboxy, cycloaliphatic, heterocycloaliphatic, aryl, heteroaryl, or combinations thereof.

In several additional examples, $R_1$ is bridged bicyclic cycloaliphatic, fused bicyclic cycloaliphatic, or spiro bicyclic cycloaliphatic, each of which is optionally substituted. For instance, $R_1$ is optionally substituted 6-9 membered bridged bicyclic cycloaliphatic. In some examples, $R_1$ is bicyclo [2.1.1]hexanyl, bicyclo[3.1.0]hexanyl, bicyclo[2.2.1]heptanyl, bicyclo[2.2.2]octanyl, bicyclo[3.1.1]heptanyl, bicyclo [3.2.1]octanyl, or bicyclo[3.3.1]nonanyl, each of which is optionally substituted with 1-3 of halo, hydroxy, nitro, cyano, aliphatic, alkoxycarbonyl, cycloaliphatic, heterocycloaliphatic, aryl, heteroaryl, or combinations thereof. In alternative examples, $R_1$ is optionally substituted 6-10 membered fused bicyclic cycloaliphatic. However, in several examples, $R_1$ is octahydropentalenyl, octahydro-1H-indenyl, or decahydronaphthalenyl, each of which is optionally substituted with 1-3 of halo, hydroxy, nitro, cyano, aliphatic, alkoxycarbonyl, cycloaliphatic, heterocycloaliphatic, aryl, heteroaryl, or combinations thereof.

In other examples, $R_1$ is optionally substituted 9-12 membered spiro bicyclic cycloaliphatic. For example, $R_1$ is spiro [5.5]undecanyl, spiro[4.5]decanyl, or spiro[5.6]dodecanyl, each of which is optionally substituted.

In some embodiments, $R_1$ is optionally substituted adamantyl.

In alternative embodiments, $R_1$ is optionally substituted heterocycloaliphatic. In several embodiments, $R_1$ is optionally substituted monocyclic or bicyclic heterocycloaliphatic having 1-3 heteroatoms independently selected from N, O, and S.

In several examples, $R_1$ is optionally substituted 4-8 membered monocyclic heterocycloaliphatic having 1-3 heteroatoms independently selected from N, O, and S. In other examples, $R_1$ is tetrahydrofuranyl, pyrrolinyl, pyrrolidinyl, 1,3-dioxolanyl, imidazolidinyl, 2-imidazolinyl, pyrazolinyl, pyrazolidinyl, tetrahydropyranyl, piperidinyl, 1,4-dioxanyl, morpholinyl, 1,4-dithiane, thiomorpholine, or piperazinyl, each of which is optionally substituted with 1-3 of halo, hydroxy, nitro, cyano, aliphatic, carboxy, cycloaliphatic, heterocycloaliphatic, aryl, oxime, heteroaryl, (aliphatic)heteroaryl, (aliphatic)heterocycloaliphatic, (aliphatic)carbonyl, or combinations thereof.

In several examples, $R_1$ is bridged bicyclic heterocycloaliphatic, fused bicyclic heterocycloaliphatic, or spiro bicyclic heterocycloaliphatic, each of which is optionally substituted.

In several additional examples, $R_1$ is optionally substituted 6-9 membered bridged bicyclic heterocycloaliphatic. For example, $R_1$ is 5-azabicyclo[2.1.1]hexanyl, 7-azabicyclo [2.2.1]heptanyl, or 8-azabicyclo[3.2.1]octanyl, each of which is optionally substituted with 1-3 of halo, hydroxy, nitro, cyano, aliphatic, alkoxycarbonyl, cycloaliphatic, heterocycloaliphatic, aryl, heteroaryl, or combinations thereof.

In several alternative examples, $R_1$ is optionally substituted 9-12 membered spiro bicyclic heterocycloaliphatic. For example, $R_1$ is 1,4-dioxaspiro[4.5]decanyl; 1,4-dioxaspiro [4.4]nonanyl; 1,5-dioxaspiro[5.5]undecanyl; or 6,10-dioxaspiro[4.5]decanyl; each of which is optionally substituted.

In some embodiments, $R_1$ is optionally substituted aliphatic. For example, $R_1$ is optionally substituted straight or branched $C_{1-8}$ aliphatic. In several other examples, $R_1$ is methyl, ethyl, propyl, isopropyl, butyl, sec-butyl, tert-butyl, pentyl, isopentyl, or neohexyl, each of which is optionally substituted with 1-3 of halo, oxo, oxime, or optionally substituted alkoxy, optionally substituted amino, optionally substituted aliphaticsulfonyl, optionally substituted cycloaliphatic, optionally substituted heterocycloaliphatic, or combinations thereof. In still more examples, $R_1$ is methyl optionally substituted with 1-2 of cyclopropyl, cyclopentyl, cyclohexyl, cycloheptyl, cyclooctyl, or combinations thereof.

In several embodiments, $R_1$ is one selected from hydrogen; tetrahydrofuran-3-yl-methyl; 4-(hydroxy)cyclohexyl; 4-(ethoxy(imino)cyclohexyl; cyclohexyl; cycloheptanyl; N-(methyl(carbonyl))piperidyl; (bicyclo[2.2.1]hept-2-yl) methyl; 3-(methyl)cyclohexyl; bicyclo[2.2.1]heptyl; isopropyl; tetrahydro-2H-pyran-3-yl; N-(but-3-ynyl(oxy(carbonyl)))piperidine-4-yl; N-(ethoxy(carbonyl(piperidine-4-yl) methyl; 4-propylcyclohexyl; 2-methoxycyclohexyl; 4-(phenyl(methyl(oxy(imino))))cyclohexyl; cycloheptyl; N-(isopropyl(oxy(carbonyl)))piperidine-4-yl; 4-(cyclohexane-yl)cyclohexyl; (cyclopropane-yl)methyl; cyclooctyl; 4-(methoxy(imino))cyclohexyl; N-(propoxy(carbonyl))piperidine-4-yl; N-(pent-2-ynyl(oxy(carbonyl)))piperidine-4-yl; 4-(tertbutyl(oxy(imino)))cyclohexyl; (cyclohexyl)methyl; 4-(ethyl)cyclohexyl; 2,6,6-(trimethyl(cyclohexa-1,3-diene-yl))methyl; N-(methoxy(ethoxy(carbonyl))) piperidine-4-yl; decahydronaphthalene-2-yl; 1,1-dimethylpropyl; propyl; 4-(ethoxy(carbonyl))cyclohexyl; tetrahydro-2H-pyran-4-yl; 3-(methyl)cyclopentyl; 4-(methyl)cyclohexyl; 2-(ethyl)butyl; 4,4-(dimethyl)cyclohex-2- ene-yl; ethyl; bicyclo[2.2.1]hept-2-yl; 2-(methyl)cyclohexyl; 1,4-dioxaspiro[4.5]dec-8-yl; N-(prop-2-yn-yl(oxy(carbonyl)))piperidine-4-yl; piperidine-4-yl; bicyclo[2.2.2]octane-2-yl; methyl; (tetrahydro-2H-pyran-4-yl)methyl; 4-(isopropoxy(imino))cyclohexyl; N-(phenyl(carbonyl))piperidine-4-yl; phenylmethyl; N-(methoxy(carbonyl))piperidine-4-yl; cyclopentyl; 4-(tertbutyl)cyclohexyl; 3,3-dimethylbutyl; 2,4-(dimethyl(cyclohex-3-ene-yl))methyl; 4-oxocyclohexyl; 3,3-dimethyl-1,5-dioxaspiro[5.5]undecane-9-yl; 4-(ethoxy(imino))cyclohexyl; bicyclo[3.2.1]octane-3-yl; bicyclo[3.2.1]octane-2-yl; 6,6-dimethylbicyclo[3.1.1]hept-2-ene-2-yl; ethylpropyl; N-(pyrazine-2-yl)piperidine-4-yl; 4-(trifluoromethyl)cyclohexyl; 3-methylbutyl; 4-(phenyl(oxy(imino)))cyclohexyl; (cyclohex-1-ene-yl)methyl; 4-(cyano-4-(phenyl))cyclohexyl; 4-(prop-2-ene-yl(oxy(imino)))cyclohexyl; tetrahydro-2H-thiopyran-4-yl; cyclopentylmethyl; cyclononyl; cyclobuty; adamantyl; 8-ethoxycarbonyl-8-azabicyclo[3.2.1]octane-3-yl; 3-(trifluoromethyl)cyclohexyl; bicyclo[3.3.1]nonane-9-yl; N-(cyclopropyl(carbonyl))piperidine-4-yl; 4-isopropyl; spiro[5.5]undecane-2-yl; 4-(phenyl)cyclohexyl; (tetrahydro-2H-pyran-4-yl)methyl; (bicyclo[2.2.1]hept-2-yl)methyl; 4-(3-ethyl-1,2,4-thiadiazole-5-yl)cyclohexyl; N-(3-ethyl-1,2,4-thiadiazole-5-yl)piperidine-4-yl; cyclohexylmethyl; and 4-(3-methyl-1,2,4-thiadiazole-5-yl)cyclohexyl.

2. Substituent $R_2$ $R_2$ is $-Z^BR_5$, wherein each $Z^B$ is independently a bond or an optionally substituted branched or straight $C_{1-6}$ aliphatic chain wherein up to two carbon units of $Z^B$ are optionally and independently replaced by $-CO-$, $-CS-$, $-CONR^B-$, $-CONR^BNR^B-$, $-CO_2-$, $-OCO-$, $-NR^BCO_2-$, $-O-$, $-NR^BCONR^B-$, $-OCONR^B-$, $-NR^BNR^B-$, $-NR^BCO-$, $-S-$, $-SO-$, $-SO_2-$, $-NR^B-$, $-SO_2NR^B-$, $-NR^BSO_2-$, or $-NR^ASO_2NR^A-$; each $R_5$ is independently $R^B$, halo, $-OH$, $-NH_2$, $-NO_2$, $-CN$, or $-OCF_3$; and each $R^B$ is independently hydrogen, optionally substituted $C_{1-4}$ aliphatic, optionally substituted cycloaliphatic, optionally substituted heterocycloaliphatic, optionally substituted aryl, or optionally substituted heteroaryl.

In several embodiments, $R_2$ is hydrogen or optionally substituted straight or branched $C_{1-6}$ aliphatic. For example, $R_2$ is optionally substituted straight or branched $C_{1-6}$ alkyl. In other examples, $R_2$ is methyl, ethyl, propyl, isopropyl, butyl, sec-butyl, tert-butyl, pentyl, isopentyl, or neohexyl, each of which is optionally substituted. In some examples, $R_2$ is methyl, ethyl, or propyl, each of which is optionally substituted with 1-3 of halo, hydroxy, oxo, cyano, or optionally substituted cycloaliphatic, optionally substituted heterocycloaliphatic, optionally substituted aryl, optionally substituted heteroaryl, or optionally substituted alkoxy. In other examples, $R_2$ is optionally substituted $C_{2-6}$ alkenyl or optionally substituted $C_{2-6}$ alkynyl. For example, $R_2$ is prop-2-ene-yl, but-2-ene-yl, but-3-ene-yl, but-2-yn-yl, or but-3-yn-yl, each of which is optionally substituted with 1-3 of halo, hydroxy, oxo, cyano, or optionally substituted cycloaliphatic, optionally substituted heterocycloaliphatic, optionally substituted aryl, optionally substituted heteroaryl, or optionally substituted alkoxy.

In several embodiments, $R_2$ is one selected from hydrogen, but-2-yn-yl; isopropyl, propyl, 2-(oxo)propyl, ethyl, (methoxy)ethyl, 2-(methyl)propyl, methyl, (phenyl)methyl, prop-2-ene-yl, and 2-(phenyl-2-(oxo))ethyl.

3. Substituent $R_3$

Each $R_3$ is independently hydrogen, halo, nitro, cyano, hydroxy, optionally substituted aliphatic, optionally substituted (aliphatic)oxy, optionally substituted cycloaliphatic, optionally substituted heterocycloaliphatic, optionally substituted aryl, or optionally substituted heteroaryl.

In several embodiments, $R_3$ is independently hydrogen, halo, nitro, cyano, hydroxy, optionally substituted aliphatic, optionally substituted (aliphatic)oxy, optionally substituted cycloaliphatic, or optionally substituted heterocycloaliphatic.

In several embodiments, $R_3$ is independently $-Z^CR_6$, wherein each $Z^C$ is independently a bond or an optionally substituted branched or straight $C_{1-6}$ aliphatic chain wherein up to two carbon units of $Z^C$ are optionally and independently replaced by $-CO-$, $-CS-$, $-CONR^C-$, $-CONR^C-NR^C-$, $-CO_2-$, $-OCO-$, $-NR^CCO_2-$, $-O-$, $-NR^CCONR^C-$, $-OCONR^C-$, $-NR^CNR^C-$, $-NR^CCO-$, $-S-$, $-SO-$, $-SO_2-$, $-NR^C-$, $-SO_2NR^C-$, $-NR^CSO_2-$, or $-NR^CSO_2NR^C-$; each $R_6$ is independently $R^C$, halo, $-OH$, $-NH_2$, $-NO_2$, $-CN$, or $-OCF_3$; and each $R^C$ is independently hydrogen, optionally substituted $C_{1-8}$ aliphatic group, optionally substituted cycloaliphatic, optionally substituted heterocycloaliphatic, optionally substituted aryl, or optionally substituted heteroaryl.

In several embodiments, $R_3$ is optionally substituted aliphatic, such as optionally substituted alkyl, optionally substituted alkenyl, or optionally substituted alkynyl. In one group of examples, $R_3$ is straight or branched optionally substituted $C_{1-6}$ alkyl (e.g., $C_{1-3}$ alkyl). For example, $R_3$ is methyl, ethyl, propyl, isopropyl, butyl, sec-butyl, tert-butyl, pentyl, hexyl, or neohexyl, each of which is optionally substituted with 1-3 of halo, hydroxy, oxo, cyano, nitro, or alkoxy, acyl, amino, cycloaliphatic, heterocycloaliphatic, aryl, heteroaryl, or combinations thereof. In several embodiments, $R_3$ is cyano.

In another group of examples, $R_3$ is straight or branched optionally substituted $C_{2-6}$ alkenyl; and in another group of examples, $R_3$ is straight or branched optionally substituted $C_{2-6}$ alkynyl. For example, $R_3$ is straight or branched $C_{2-6}$ alkenyl that is optionally substituted with 1-3 of halo, hydroxy, oxo, cyano, nitro, or alkoxy, acyl, amino, cycloaliphatic, heterocycloaliphatic, aryl, heteroaryl, or combinations thereof. In other examples, $R_3$ is straight or branched $C_{2-6}$ alkynyl that is optionally substituted with 1-3 of halo, hydroxy, oxo, cyano, nitro, or alkoxy, acyl, amino, cycloaliphatic, heterocycloaliphatic, aryl, heteroaryl, or combinations thereof.

In several embodiments, $R_3$ is optionally substituted (aliphatic)oxy. For example, $R_3$ is optionally substituted $C_{1-3}$ alkoxy. In still other examples, $R_3$ is methoxy, ethoxy, or propoxy, each of which is optionally substituted.

In several embodiments, $R_3$ is $-Z^CR_6$, $Z^C$ is a bond, and $R_6$ is hydrogen.

4. Group n n is 0-4. For example, n is 0, 1, 2, 3, or 4.

5. Group X

X is $-NR_{50}-$ or $-O-$, wherein $R_{50}$ is independently hydrogen or an optionally substituted $C_{1-6}$ aliphatic.

In several embodiments, X is $-O-$.

C. Subgeneric Compounds

Another aspect of the present invention provides compounds of formula Ia that are useful for modulating the activity and/or activities of muscarinic receptor(s) in accordance to formula Ia:

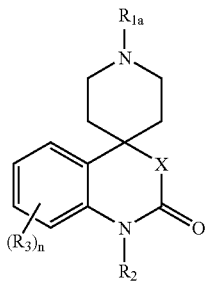

Ia or a pharmaceutically acceptable salt thereof, wherein X, $R_2$, $R_3$, and n are defined in formula I above.

$R_{1a}$ is optionally substituted aliphatic, optionally substituted cycloaliphatic, or optionally substituted heterocycloaliphatic. However, when $R_{1a}$ is substituted aliphatic, $R_{1a}$ is substituted with 1-3 of halo, cyano, nitro, hydroxy, —$NH_2$, optionally substituted alkoxy, optionally substituted cycloaliphatic, or optionally substituted heterocycloaliphatic. However, when $R_{1a}$ is an aliphatic substituted with a monocyclic heterocycloaliphatic, the monocyclic heterocycloaliphatic is not substituted with aryl; and when $R_{1a}$ is an optionally substituted cycloaliphatic, $R_{1a}$ is not substituted with a substituted monocyclic heterocycloaliphatic.

Another aspect of the present invention provides compounds of formula Ib that are useful for modulating the activity and/or activities of muscarinic receptor(s) in accordance to formula Ib:

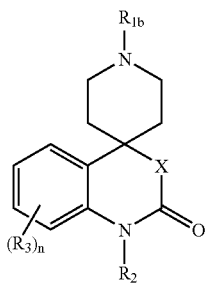

Ib or a pharmaceutically acceptable salt thereof, wherein X, $R_2$, $R_3$, and n are defined above in formula I.

$R_{1b}$ is optionally substituted cycloaliphatic, or optionally substituted heterocycloaliphatic. However, when $R_{1b}$ is optionally substituted cycloaliphatic, $R_{1b}$ is not substituted with a substituted monocyclic heterocycloaliphic.

In several embodiments, $R_{1b}$ is independently —$Z^D R_7$, wherein each $Z^D$ is independently a bond or an optionally substituted branched or straight $C_{1-8}$ aliphatic chain wherein up to two carbon units of $Z^D$ are optionally and independently replaced by —CO—, —CS—, —$CONR^D$—, —$CONR^D$-$NR^D$—, —$CO_2$—, —OCO—, —$NR^D CO_2$—, —O—, —$NR^D CONR^D$—, —$OCONR^D$—, —$NR^D NR^D$—, —$NR^D CO$—, —S—, —SO—, —$SO_2$—, —$NR^D$—, —$SO_2 NR^D$—, —$NR^D SO_2$—, or —$NR^D SO_2 NR^D$—. Each $R_7$ is independently $R^D$, halo, —OH, —$NH_2$, —$NO_2$, —CN, or —$OCF_3$. Each $R^D$ is independently hydrogen, optionally substituted $C_{1-8}$ aliphatic group, optionally substituted cycloaliphatic, or optionally substituted heterocycloaliphatic. However, when $R_{1b}$ is optionally substituted aliphatic, $R_{1b}$ is not substituted with a substituted monocyclic heterocycloaliphic.

Another aspect of the present invention provides compounds of formula Ic that are useful for modulating the activity and/or activities of muscarinic receptor(s) in accordance to formula Ic:

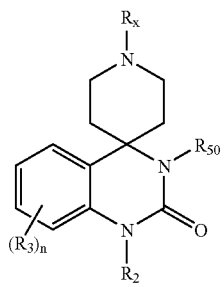

Ic or a pharmaceutically acceptable salt thereof, wherein $R_2$, $R_3$, $R_{50}$, and n are defined in formula I above.

$R_X$ is either of $R_{1a}$ or $R_{1b}$, wherein each of $R_{1a}$ or $R_{1b}$ are described above in formulae Ia and Ib.

In several embodiments, where $R_X$ is $R_{1a}$, and when $R_{1a}$ is an optionally substituted aliphatic, $R_{1a}$ is not substituted with an aryl, heteroaryl, or aryl(oxy); when $R_{1a}$ is an aliphatic substituted with a monocyclic heterocycloaliphatic, the monocyclic heterocycloaliphatic is not substituted with aryl; and when $R_{1a}$ is an optionally substituted cycloaliphatic, $R_{1a}$ is not substituted with a substituted monocyclic heterocycloaliphic.

In several embodiments, where $R_X$ is $R_{1b}$, and when $R_{1b}$ is an optionally substituted cycloaliphatic, $R_{1b}$ is not substituted with a substituted monocyclic heterocycloaliphic.

Another aspect of the present invention provides compounds of formula Ic that are useful for modulating the activity and/or activities of muscarinic receptor(s) in accordance to formula Id:

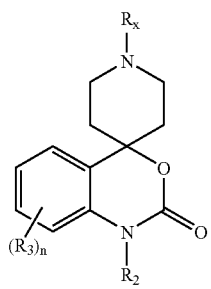

Id

Wherein $R_X$ is described above in formula $I_c$, and $R_2$, $R_3$, and n are described in formula I, above.

D. Combinations of Embodiments

Other embodiments of the present invention include any combination of $R_1$, $R_{1a}$, $R^{1b}$, $R_2$, $R_3$, X, and n.

E. Exemplary Compounds

Specific exemplary compounds of formulae (I, Ia, Ib, Ic, and Id) are shown below in Table 1.

TABLE 1
Exemplary compounds of the present invention.
1
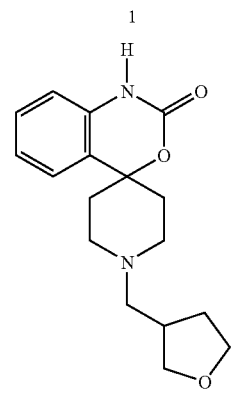
2
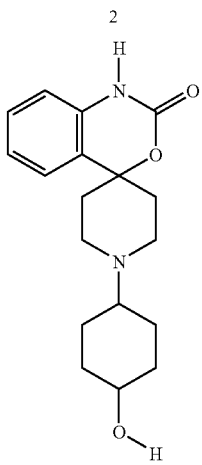
3
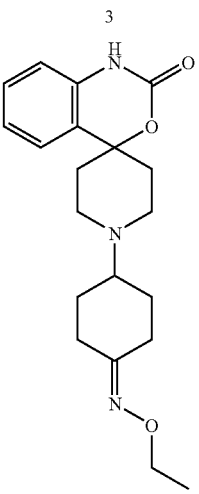
4
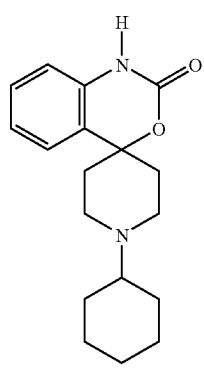
5
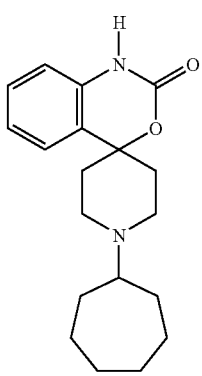
6
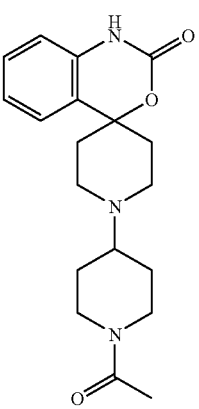
7
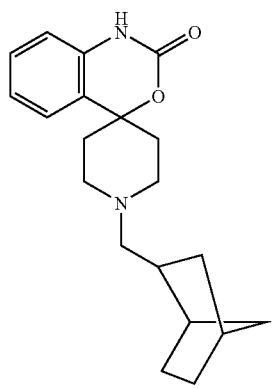
8
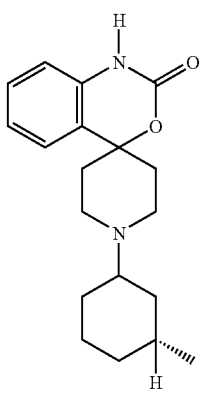
9
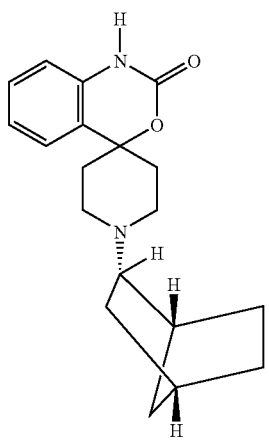

TABLE 1-continued
Exemplary compounds of the present invention.
| 10 | 11 | 12 |
|---|---|---|
| 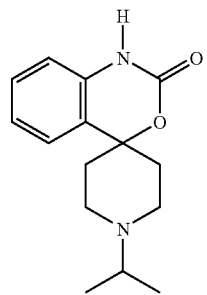 | 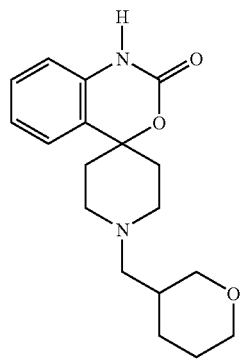 | 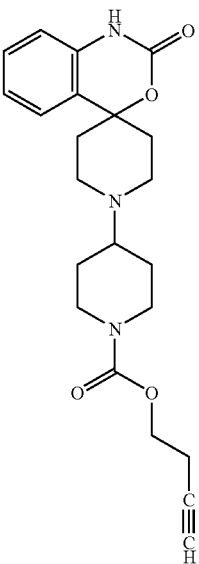 |
| 13 | 14 | 15 |
|---|---|---|
| 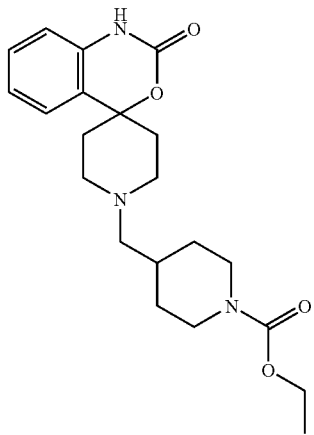 | 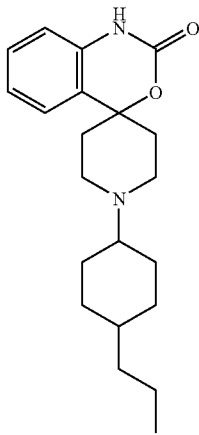 | 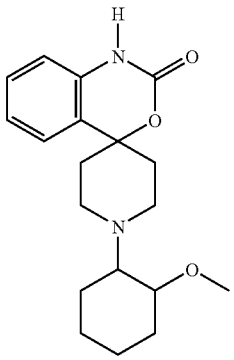 |

TABLE 1-continued
Exemplary compounds of the present invention.
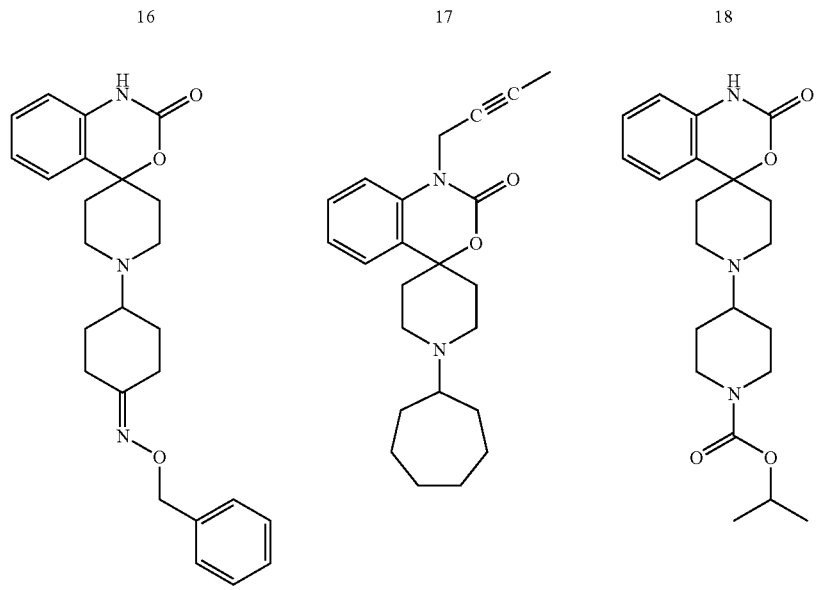
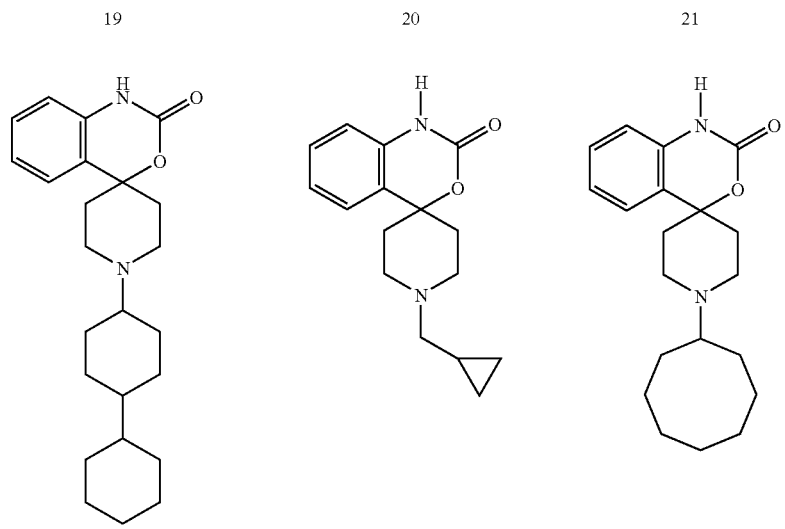

TABLE 1-continued
Exemplary compounds of the present invention.
| 22 | 23 | 24 |
|---|---|---|
| 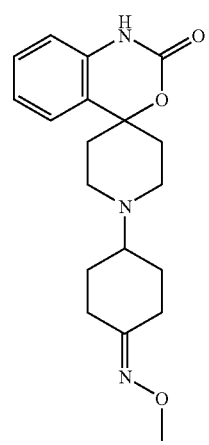 | 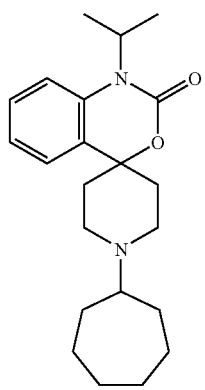 | 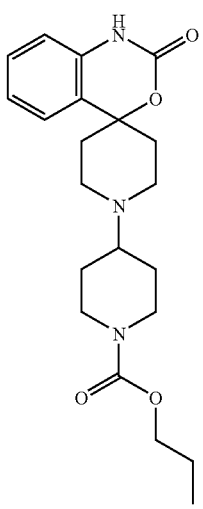 |
| 25 | 26 | 27 |
|---|---|---|
| 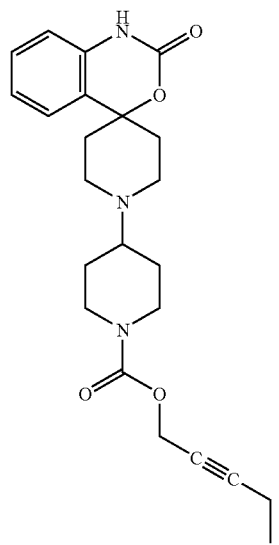 | 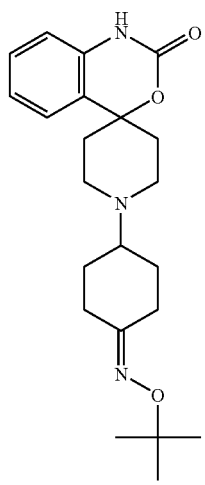 | 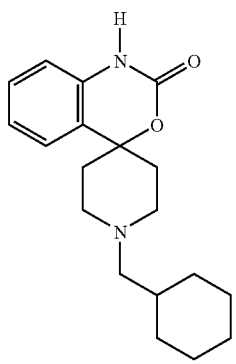 |

TABLE 1-continued
Exemplary compounds of the present invention.
| 28 | 29 | 30 |
|---|---|---|
| 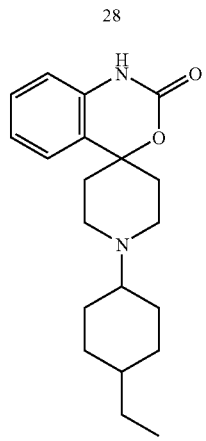 | 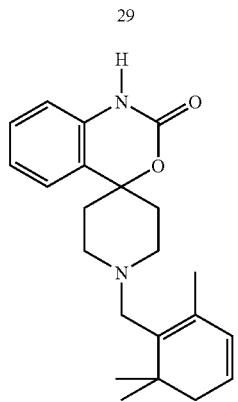 | 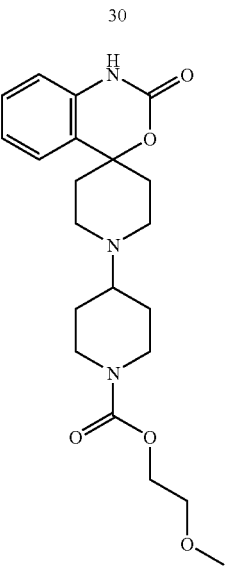 |
| 31 | 32 | 33 |
|---|---|---|
| 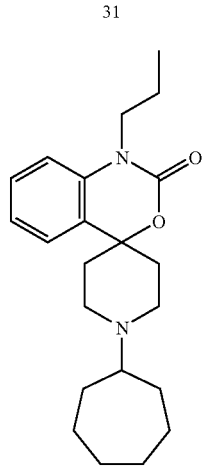 | 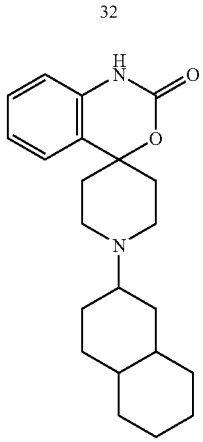 | 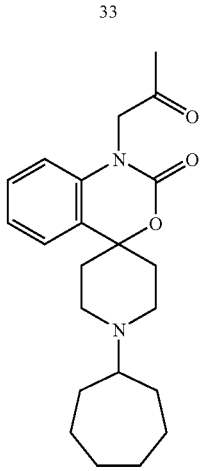 |
| 34 | 35 | 36 |
|---|---|---|
| 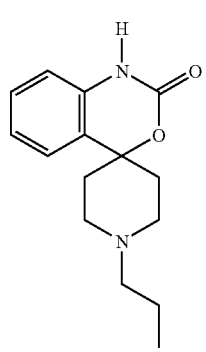 | 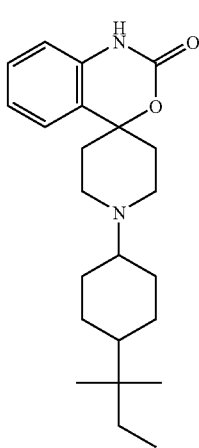 | 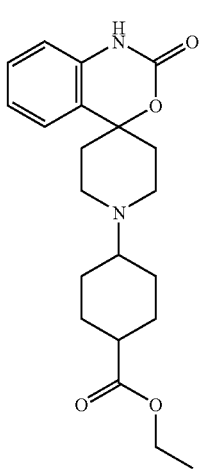 |

TABLE 1-continued
Exemplary compounds of the present invention.
| 37 | 38 | 39 |
|---|---|---|
| 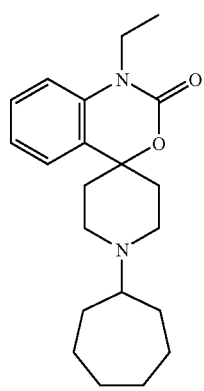 | 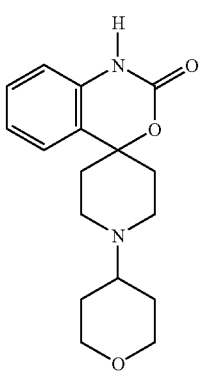 | 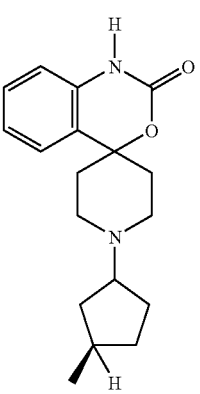 |
| 40 | 41 | 42 |
|---|---|---|
| 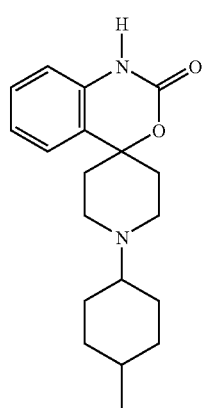 | 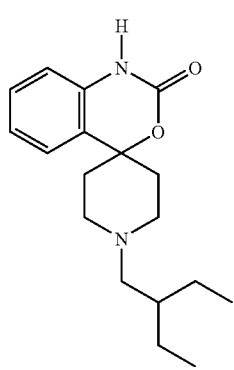 | 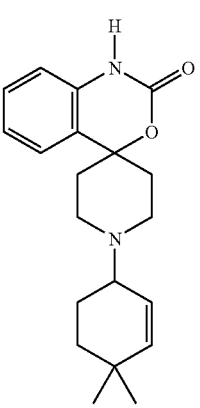 |
| 43 | 44 | 45 |
|---|---|---|
| 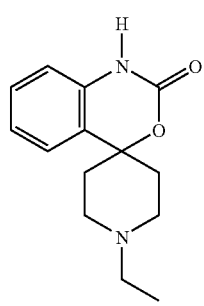 | 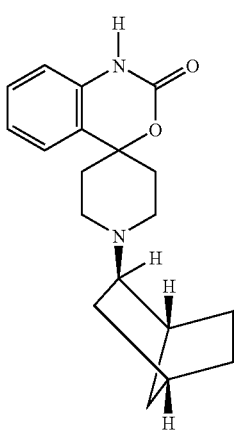 | 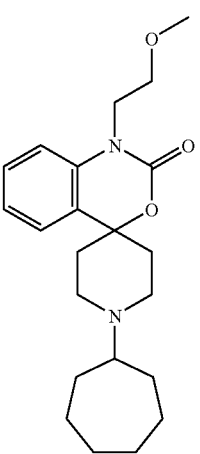 |

TABLE 1-continued
Exemplary compounds of the present invention.
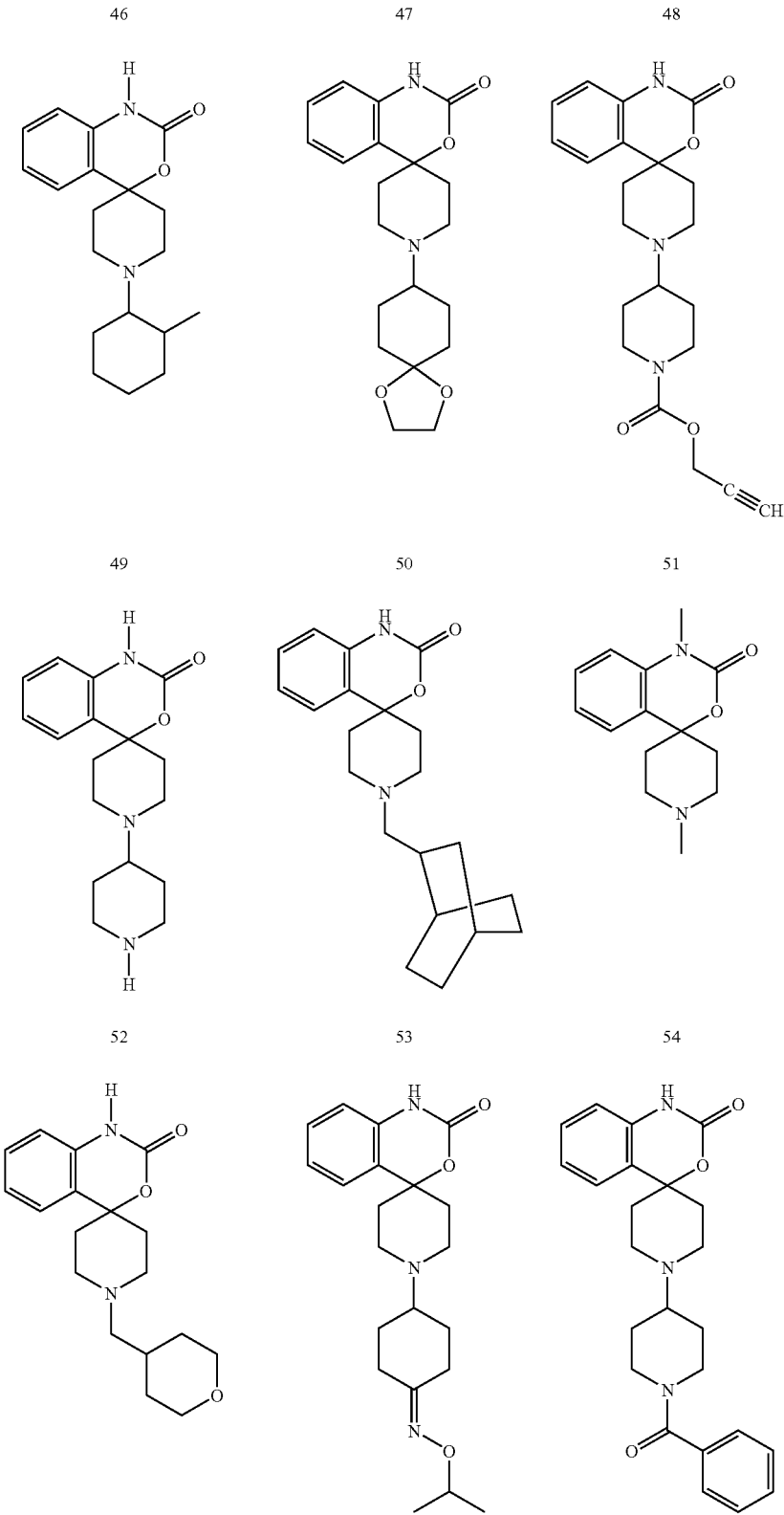

TABLE 1-continued
Exemplary compounds of the present invention.
| 55 | 56 | 57 |
|---|---|---|
| 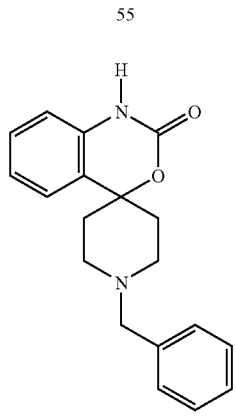 | 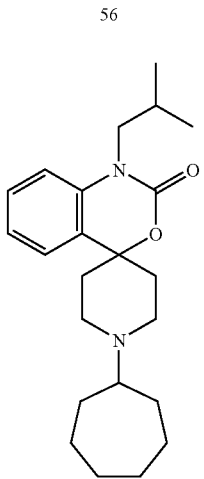 | 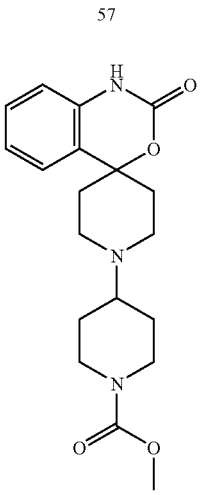 |
| 58 | 59 | 60 |
| 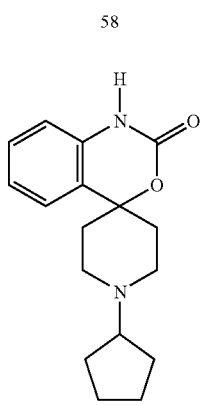 | 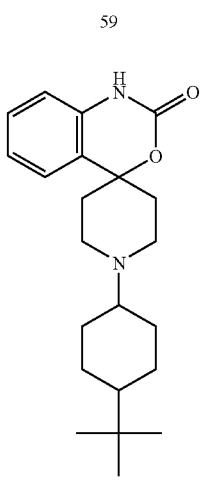 | 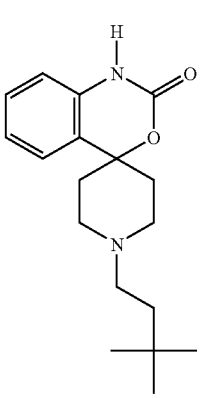 |
| 61 | 62 | 63 |
| 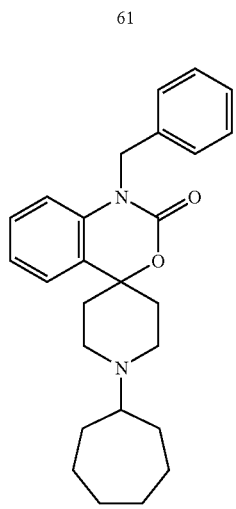 | 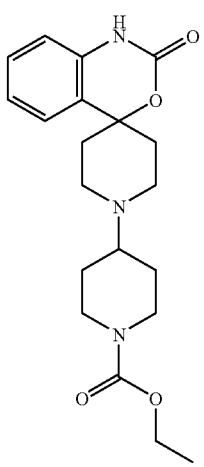 | 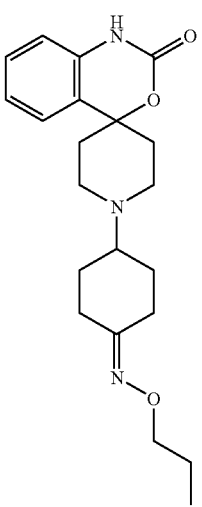 |

TABLE 1-continued
Exemplary compounds of the present invention.
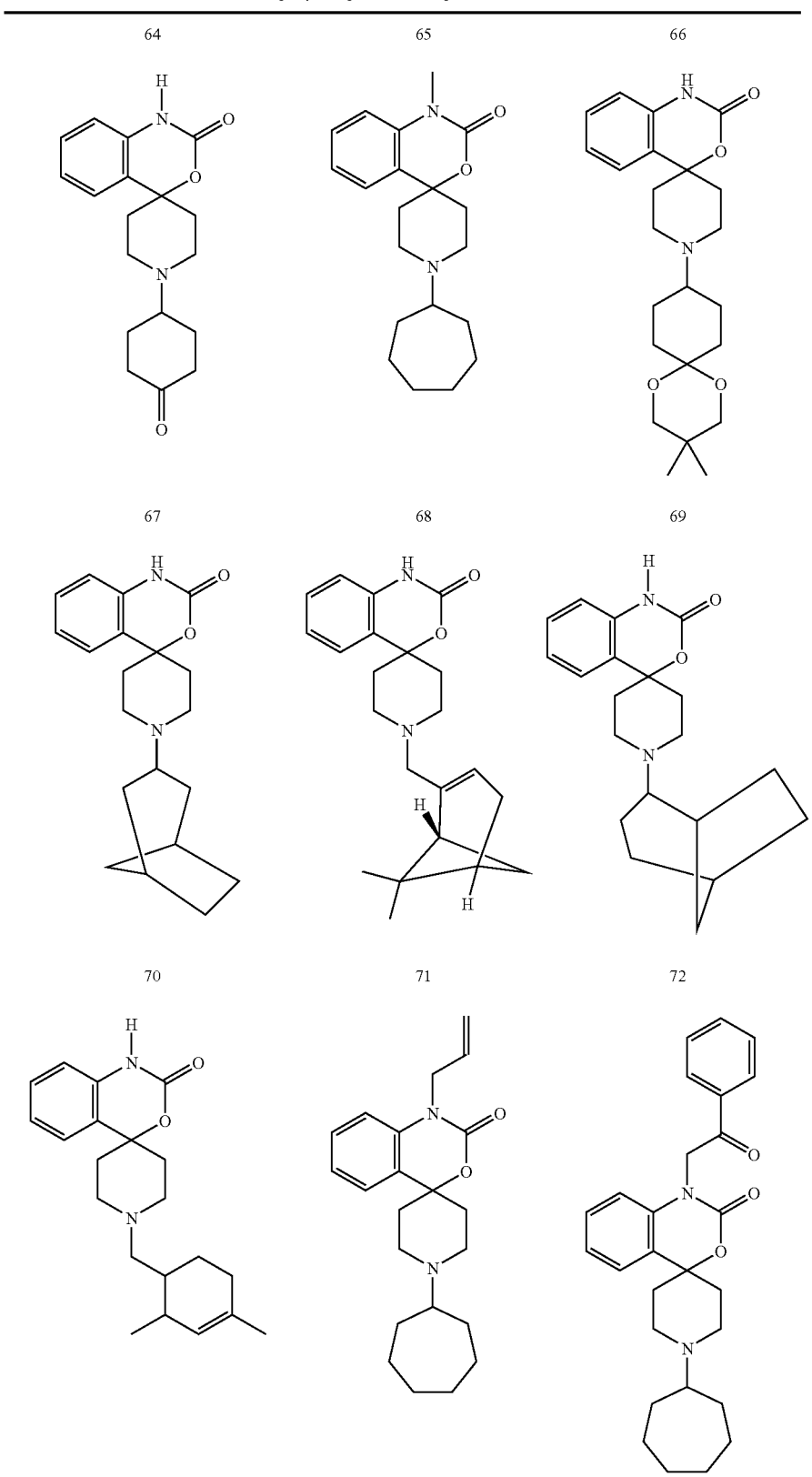

TABLE 1-continued
Exemplary compounds of the present invention.
| 73 | 74 | 75 |
|---|---|---|
| 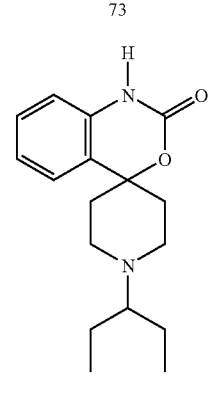 | 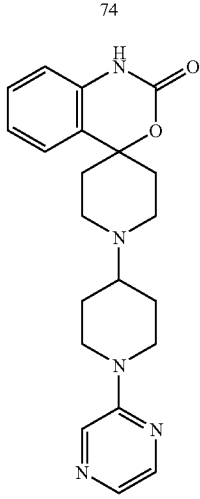 | 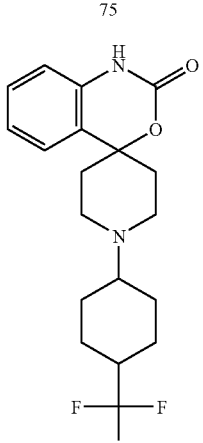 |
| 76 | 77 | 78 |
| 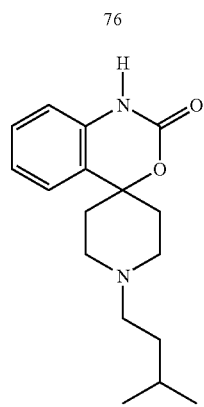 | 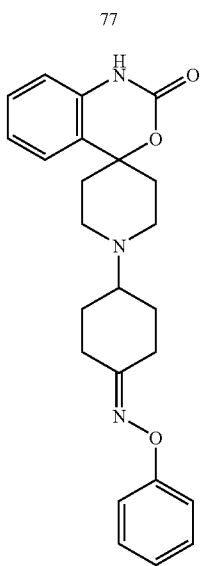 | 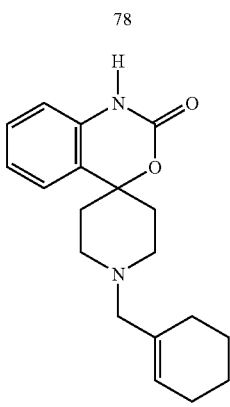 |
| 79 | 80 | 81 |
| 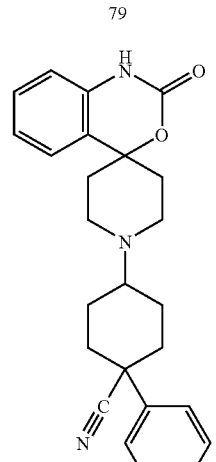 | 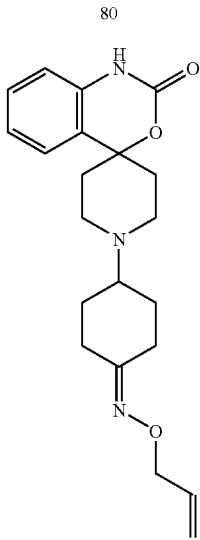 | 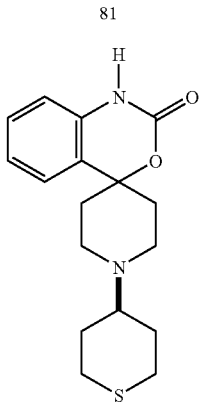 |

TABLE 1-continued
Exemplary compounds of the present invention.
| 82 | 83 | 84 |
|---|---|---|
| 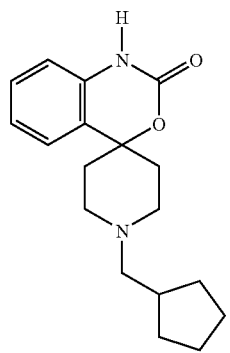 | 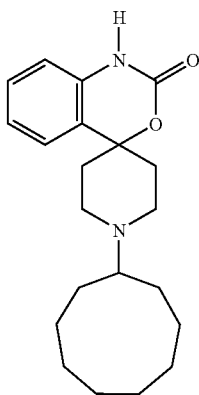 | 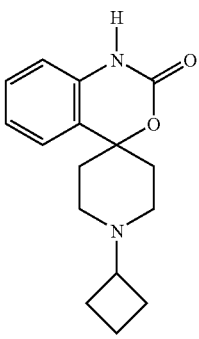 |
| 85 | 86 | 87 |
| 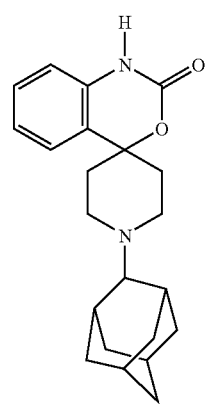 | 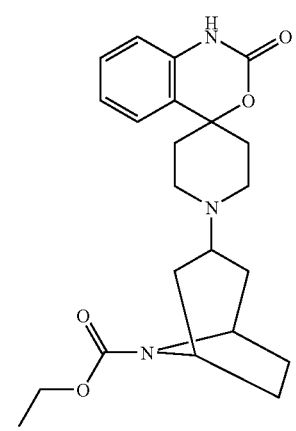 | 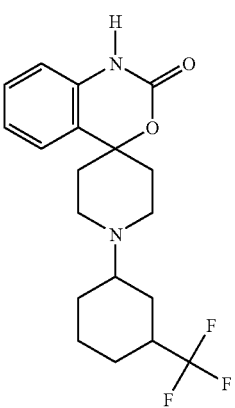 |
| 88 | 89 | 90 |
| 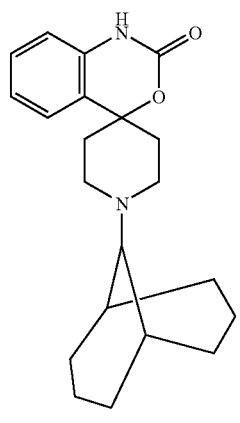 | 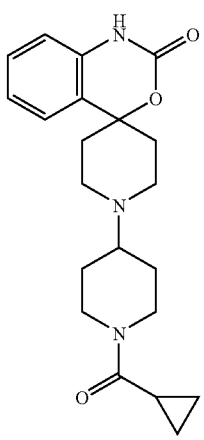 | 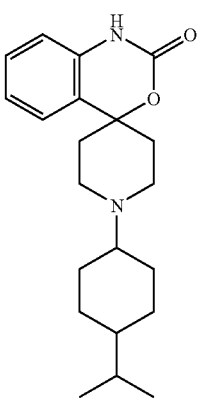 |

TABLE 1-continued
Exemplary compounds of the present invention.
| 91 | 92 | 93 |
|---|---|---|
| 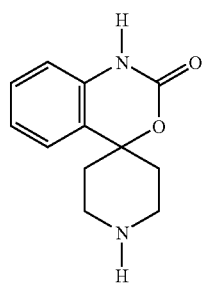 | 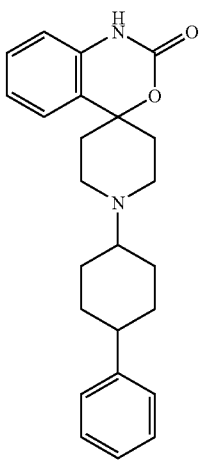 | 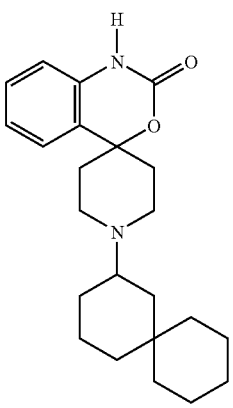 |
| 94 | 95 | 96 |
|---|---|---|
| 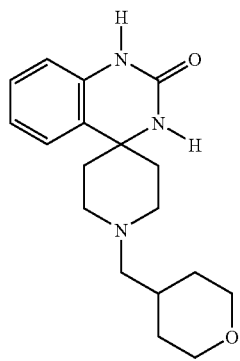 | 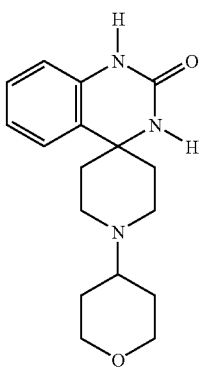 | 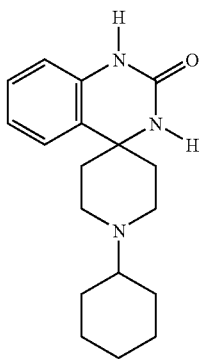 |
| 97 | 98 | 99 |
|---|---|---|
| 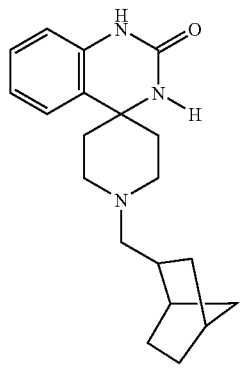 | 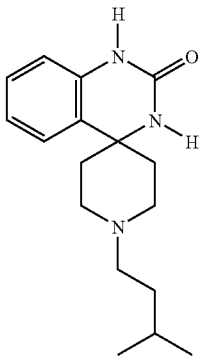 | 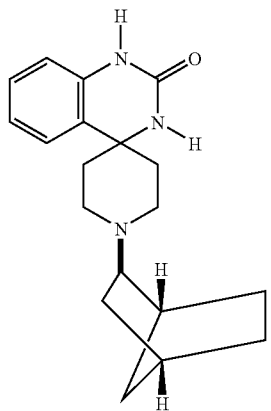 |

TABLE 1-continued
Exemplary compounds of the present invention.
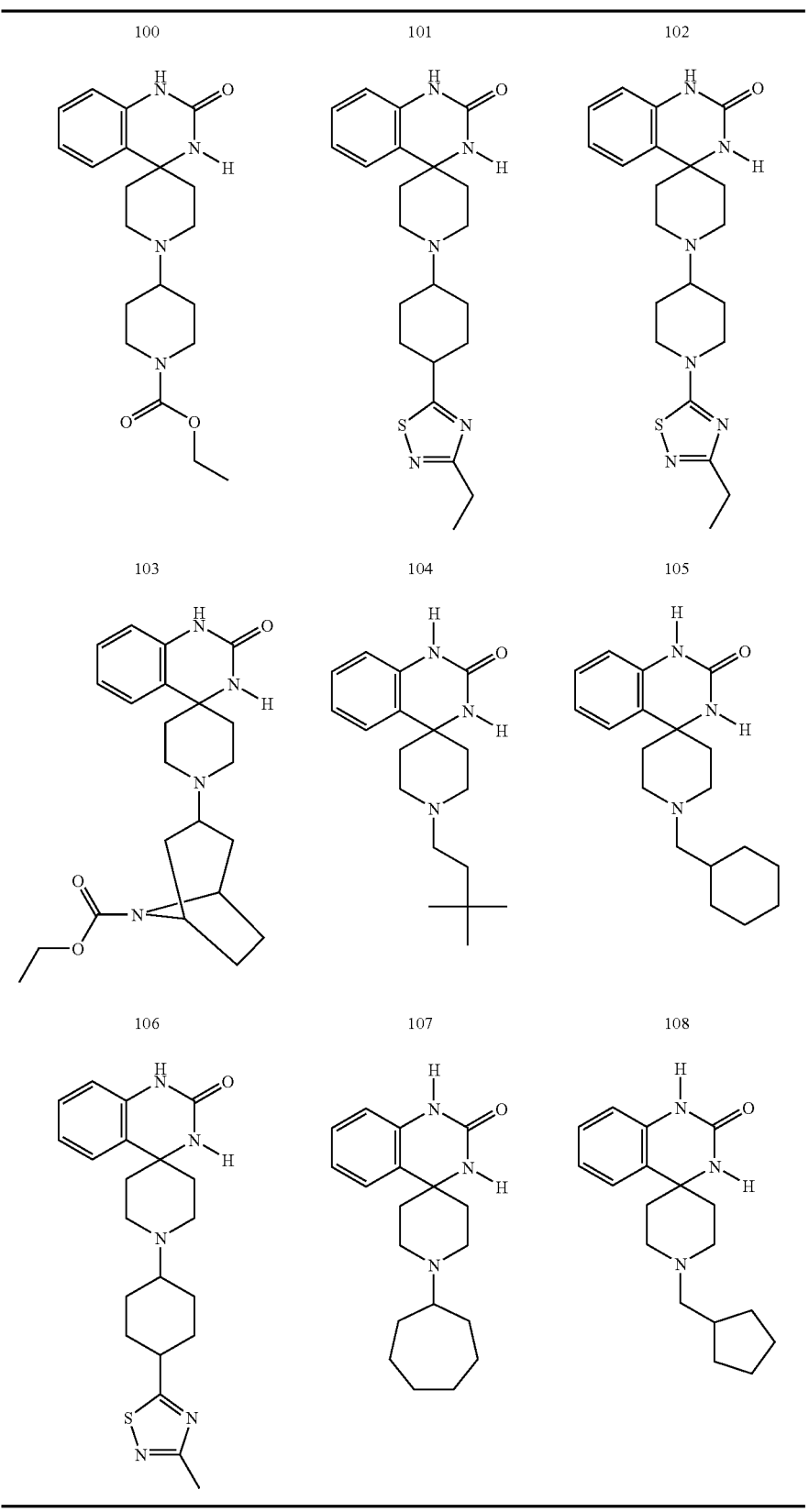

III. Synthetic Schemes

Compounds of formulae (I, Ia, Ib, Ic, and Id) can be prepared from commercially available starting materials using any methods known in the art. In one method, compounds of formulae (I, Ia, Ib, Ic, and Id) wherein $R_1$ is a an optionally substituted saturated, partially unsaturated, or fully unsaturated 5-10 membered ring system including 0-3 heteroatoms selected from N, O, or S, are prepared according to schemes 1-2 below.

Scheme 1:

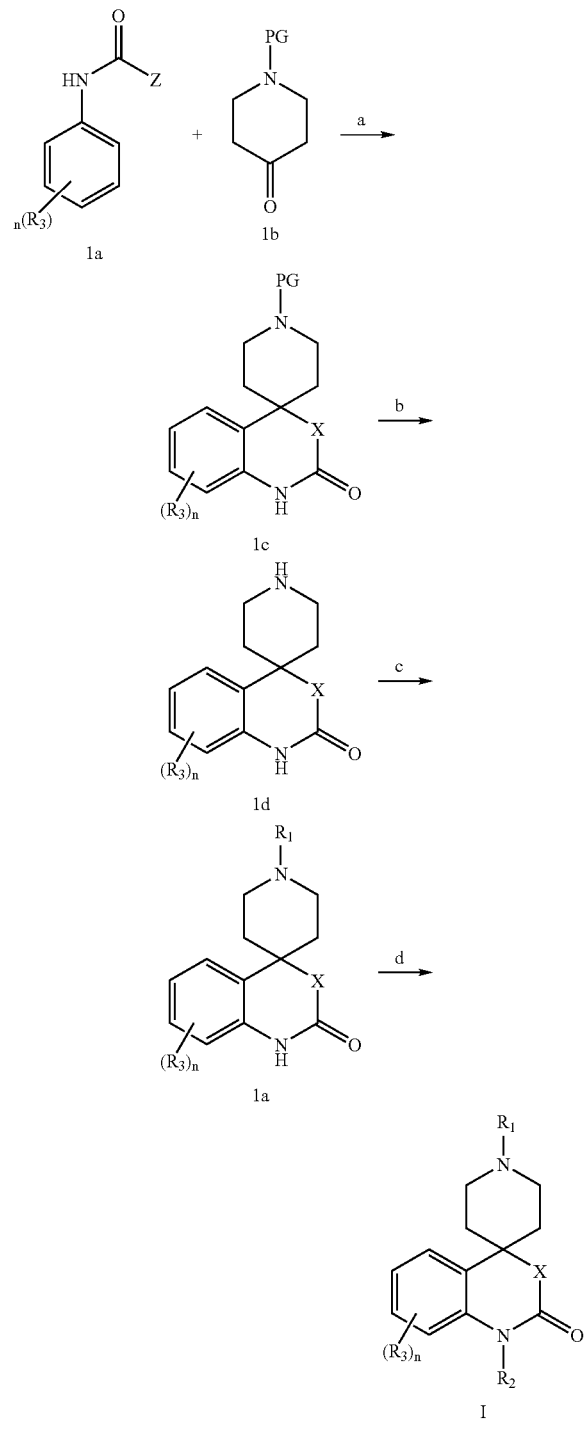

PG is a protecting group, and X is defined above in formula I.

Referring to scheme 1, the starting material (1a), wherein Z is —$NH_2$, is reacted with N-piperidin-4-one 1b) in the presence of an acid, such as polyphosphoric acid, and heat to the 1'H-spiro[piperidine-4,4'-quinazolin]-2'(3'H)-one (1c), as described in Berkhout, Theo A. et al., "CCR2: Characterization of the Antagonist Binding Site from a Combined Receptor Modeling/Mutagenesis Approach," J. Med. Chem., 46(19), pp. 4070-4086 (2003); Clark, Robin D. et al., "Synthesis and antihypertensive activity of 4'-substituted spiro [4H-3,1-benzoxazine-4,4'-piperidin]-2(1H)-ones," J. Med. Chem., 26(5), pp. 657-61 (1983); and WO 2005/065779 A1 "Calcitonin Gene Related Peptide Receptor Antagonists". Alternatively, when Z is —$OC(CH_3)_3$, starting material (1a) is reacted with N-protected piperidin-4-one (1b) in the presence of a strong base, such as tert-butyllithium, to produce the spiro[benzo[d][1,3]oxazine-4,4'-piperidin]-2(1H)-one (1c).

Removal of the protecting group (e.g., by treating intermediate (1c) with ammonium formate, MeOH, Pd/C, at room temp or heat; by treating intermediate (1c) with Pd/C, MeOH, and $H_2$; or by treating the intermediate (1c) with TFA, $CH_2Cl_2$ at 0° C. to room temperature) produces the free amine (1d). Reductive amination of the amine (1d) provides the compounds of the invention (I). The reaction of amine (1d) with an appropriate aldehyde or ketone under reductive amination conditions (step c), typically using $NaBH(OAc)_3$ in DCE/AcOH/TEA at room temperature, may be used to provide the desired compounds of formula I. For less reactive ketones, more forcing conditions may be used. For example, the treatment of the amine (1d) and the ketone in a neat solution of $Ti(OiPr)_4$, followed by treatment with $NaBH_4$ in MeOH, may be used to provide the desired compounds of formula I. See Abdel-Magid, A. F. et al., "Reductive Amination of Aldehydes and Ketones with Sodium Triacetoxyborohydride. Studies on Direct and Indirect Reductive Amination Procedures," J. Org. Chem., 61, pp. 3849-3862 (1996) and the references sited therein.

Compounds of formula Ia may be further elaborated by reaction with an alkyl halide in the presence of an appropriate base (step d) to provide additional compounds of formula I. Typically, the secondary amine is reacted with an alkyl iodide, bromide, or chloride in the presence of an appropriate base, either at room temperature, with heat, or under microwave conditions. Bases may be organic such as triethylamine, or inorganic such as $Na_2CO_3$ or $Cs_2CO_3$. Typical reaction solvents include but are not limited to DMF, acetone, and acetonitrile.

Scheme 2 illustrates alternative conditions as example for the synthesis of compounds of formula I in which $R_1$ is a monocyclic or bicyclic ring system that contains or is substituted with a protected functionality which may be either be retained, deprotected and retained, or deprotected and further elaborated to produce additional compounds of formulae (I, Ia, Ib, Ic, and Id).

Scheme 2:

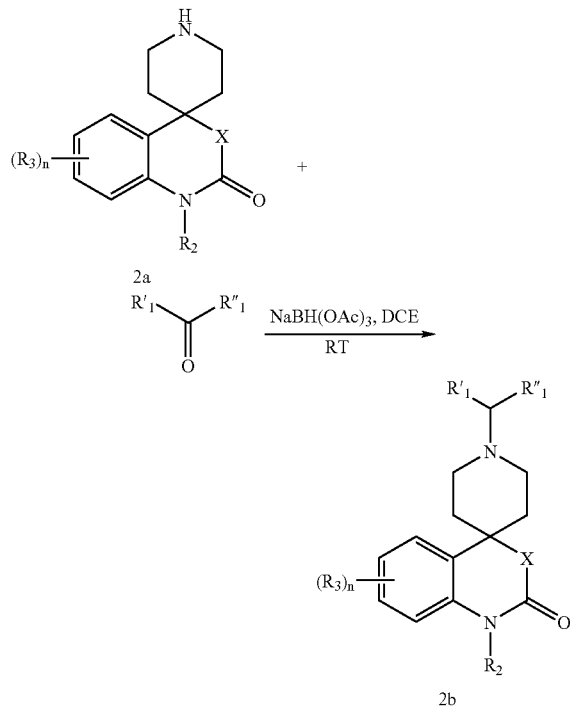

Referring to scheme 2, an alternative method of producing compounds of formulae (I, Ia, Ib, Ic, and Id) can include reacting the $R_2$-, $R_3$-substituted benzoxazinone intermediate (2a) with a ketone or aldehyde in the presence of a suitable reducing agent (sodium triacetoxyborohydride, sodium borohydride, or the like) and in the presence of a suitable solvent (e.g., dichloroethane, or the like) at room temperature to produce compounds of formulae (I, Ia, Ib, Ic, and Id). See Example 2, where either $R_1'$ or $R_1''$ is hydrogen and the non-hydrogen $R_1'$ or $R_1''$ includes an alkyl substituted with heterocycloaliphatic or cycloaliphatic.

IV. Formulations, Administrations, and Uses

The present invention includes within its scope pharmaceutically acceptable prodrugs of the compounds of the present invention. A "pharmaceutically acceptable prodrug" means any pharmaceutically acceptable salt, ester, salt of an ester, or other derivative of a compound of the present invention which, upon administration to a recipient, is capable of providing (directly or indirectly) a compound of this invention or an active metabolite or residue thereof. Preferred prodrugs are those that increase the bioavailability of the compounds of this invention when such compounds are administered to a mammal or which enhance delivery of the parent compound to a biological compartment relative to the parent species.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and $N^+(C_{1-4}\,alkyl)_4$ salts. This invention also envisions the quaternization of any basic nitrogen-containing groups of the compounds disclosed herein. Water or oil-soluble or dispersible products may be obtained by such quaternization.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

The amount of the compounds of the present invention that may be combined with the carrier materials to produce a composition in a single dosage form will vary depending upon the host treated, the particular mode of administration. Preferably, the compositions should be formulated so that a dosage of between 0.01-100 mg/kg body weight/day of the modulator can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Depending upon the particular condition, or disease, to be treated or prevented, additional therapeutic agents, which are normally administered to treat or prevent that condition, may also be present in the compositions of this invention. As used herein, additional therapeutic agents that are normally administered to treat or prevent a particular disease, or condition, are known as "appropriate for the disease, or condition, being treated."

According to a preferred embodiment, the compounds of formulae (I, Ia, Ib, Ic, and Id) are selective modulators of $M_1$, $M_2$ and $M_4$. More preferably, the compounds of formulae (I, Ia, Ib, Ic, and Id) are selective modulators of $M_1$ and/or $M_4$. Yet more preferably, certain compounds of formulae (I, Ia, Ib, Ic, and Id) are selective modulators of $M_1$. Or, preferably, certain compounds of formulae (I, Ia, Ib, Ic, and Id) are selective modulators of $M_4$.

Applicants believe that the ability of the compounds of the present invention to modulate the activity of muscarinic receptors is derived from the affinity of these compounds to the muscarinic receptors. Such affinity, applicants believe, activates a muscarinic receptor (i.e., an agonist) or inhibits the activity of a muscarinic receptor.

The term "selective" as used herein means a measurably greater ability to modulate one muscarinic receptor subtype when compared to the other muscarinic receptor subtypes. E.g., the term "selective $M_4$ agonist" means a compound that has a measurably greater ability to act as an $M_4$ agonist when compared to that compound's agonist activity with the other muscarinic receptor subtype(s).

According to an alternative embodiment, the present invention provides a method of treating a muscarinic receptor mediated disease in a mammal, such as a human, including the step of administering to said mammal a composition comprising a compound of formulae (I, Ia, Ib, Ic, and Id) or an embodiment thereof as set forth herein.

According to another embodiment, the present invention provides a method of treating a disease mediated by a muscarinic receptor including the step of administering to said mammal a composition comprising a compound of formulae (I, Ia, Ib, Ic, and Id), or other embodiments thereof as set forth above. Preferably, said disease is mediated by $M_1$, or said disease is mediated by $M_4$.

According to yet another embodiment, the present invention provides a method of treating or reducing the severity of a disease in a patient, wherein said disease is selected from CNS derived pathologies including cognitive disorders, Attention Deficit Hyperactivity Disorder (ADHD), obesity, Alzheimer's disease, various dementias such as vascular dementia, psychosis including schizophrenia, mania, bipolar disorders, pain conditions including acute and chronic syndromes, Huntington's Chorea, Friederich's ataxia, Gilles de la Tourette's Syndrome, Downs Syndrome, Pick disease, clinical depression, sudden infant death syndrome, Parkinson's disease, peripheral disorders such as reduction of intra ocular pressure in Glaucoma and treatment of dry eyes and dry mouth including Sjögren's Syndrome, wherein said method comprises the step of contacting said patient with a compound according to the present invention.

According to an alternative embodiment, the present invention provides a method of treating or reducing the severity of a disease in a patient, wherein said disease is selected from pain, psychosis (including schizophrenia, hallucinations, and delusions), Alzheimer's disease, Parkinson's disease, glaucoma, bradycardia, gastric acid secretion, asthma, or GI disturbances.

According to a preferred embodiment, the present invention is useful for treating or reducing the severity of psychosis, Alzheimer's disease, pain, or Parkinson's disease.

All references cited within this document are incorporated herein by reference.

V. Preparations and Examples

In order that the invention described herein may be more fully understood, the following examples are set forth. It should be understood that these examples are for illustrative purposes only and are not to be construed as limiting this invention in any manner.

Preparation A: Synthesis of spiro[4H-3,1-benzoxazine-4,4'-piperidin]-2(1H)-one

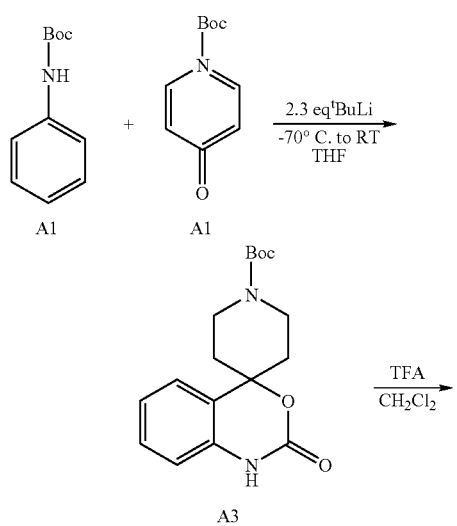

N-Boc-aniline (16.12 g, 83.4 mmol) (A1) was dissolved in anhydrous tetrahydrofuran (120 mL) and cooled to −70° C. To this solution was added dropwise, under nitrogen, a 1.7 M solution of tert-butyllithium in pentane (110 mL, 187 mmol) at −70° C. After 30 min at −70° C., the solution was warmed to −20° C. and maintained at that temperature for 2 hours. The solution was again cooled to −70° C. and treated dropwise with a solution of N-Boc-4-piperidone (15.98 g, 80.2 mmol) (A2) in anhydrous tetrahydrofuran (50 mL). The solution was slowly warmed to room temperature, treated with potassium tert-butoxide (25 mg) and stirred at room temperature overnight under nitrogen. The solution was diluted with diethyl ether (300 mL), cooled in an ice water bath and adjusted to pH 7 with 1.0 N HCl (aq). The layers were separated and the aqueous layer extracted once with diethyl ether (100 mL). The pooled organic layers were washed with water and saturated brine, then dried over $Na_2SO_4$ and filtered. The filtrate was concentrated under reduced pressure to afford a crude product as a viscous pale yellow oil. The crude product was purified via silica gel flash chromatography (25-50% ethyl acetate in hexanes) to afford tert-butyl 2-oxo-1,2-dihydrospiro[benzo[d][1,3]oxazine-4,4'-piperidine]-1'-carboxylate (A3) as a pale yellow solid. LC/MS m/z 319.0 [M+H]+, retention time 2.72 min (RP-C18, 10-99% CH3CN/0.05% TFA); 1H-NMR (400 MHz, CDCl3) δ 9.06 (br s, 1H), 7.28 (m, 1H), 7.12 (m, 2H), 6.91 (d, J=8.5 Hz, 1H), 4.12 (br d, J=9.9 Hz, 2H), 3.36 (br t, J=12.4 Hz, 2H), 2.13 (br d, J=13.1 Hz, 2H), 1.98 (m, 2H), 1.51 (s, 9H).

tert-Butyl 2-oxo-1,2-dihydrospiro[benzo[d][1,3]oxazine-4,4'-piperidine]-1'-carboxylate (6.71 g, 21.1 mmol) (A3) was dissolved in dichloromethane (50 mL), treated with trifluoroacetic acid (20 mL) and stirred at room temperature for 45 min. The reaction was concentrated under reduced pressure, re-dissolved in acetonitrile and re-concentrated under reduced pressure. The crude TFA salt was cooled in an ice water bath, dissolved in ice-cold saturated brine (20 mL) and $H_2O$ (50 mL) and basified with ice-cold 35% NaOH (aq). A small amount of product (obtained from extraction with 50 mL ethyl acetate) was added to the aqueous layer to initiate crystallization. The suspension obtained was cooled in an ice-$H_2O$ bath, filtered, rinsed with ice-cold $H_2O$ and dried to afford spiro[benzo[d][1,3]oxazine-4,4'-piperidin]-2(1H)-one (A4) free base as a white crystalline solid. Additional free base was obtained via extraction of the mother liquor with ethyl acetate (10×50 mL) and subsequent trituration of the crude free base with acetonitrile (overall yield=84%). LC/MS m/z 219.2 [M+H]+, retention time 0.58 min (RP-$C_{18}$, 10-99% $CH_3CN$/0.05% TFA); $^1$H-NMR (400 MHz, DMSO-$d_6$) δ 10.17 (br s, 1H), 7.23 (m, 2H), 7.02 (m, 1H), 6.87 (dd, J=8.2, 1.2 Hz, 1H), 2.89 (m, 2H), 2.82 (m, 2H), 1.84 (m, 4H).

Preparation B: Synthesis of ethyl 4-formylpiperidine-1-carboxylate

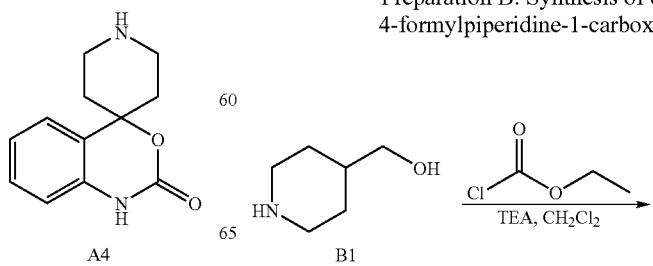

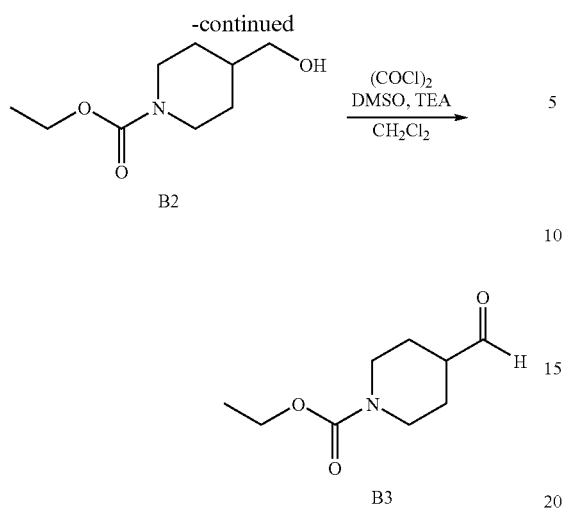

Preparation C: Synthesis of 5-chloro-3-methyl-1,2,4-thiadiazole

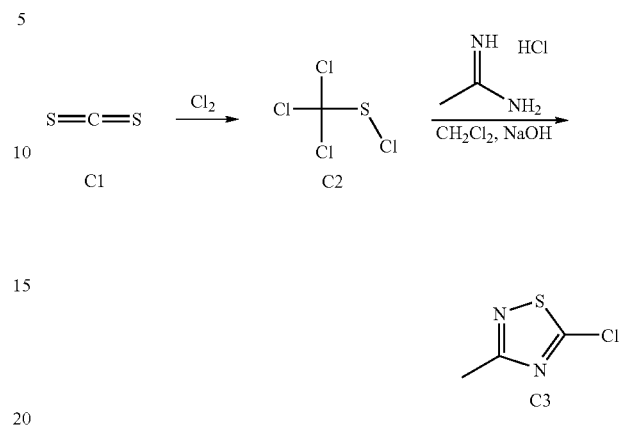

4-piperidinemethanol (10.00 g, 86.8 mmol) (B1) was dissolved in dichloromethane (350 mL), cooled in an ice water bath and treated dropwise with a solution of ethyl chloroformate (9.89 g, 91.1 mmol) in dichloromethane (50 mL), followed by the dropwise addition of a solution of triethylamine (8.78 g) in dichloromethane (50 mL). The reaction was stirred at 0° C. for 15 min, then at room temperature for 10 min. The reaction was diluted with dichloromethane (250 mL) and washed successively with water (2×150 mL), 0.1 N HCl (2×150 mL), saturated brine (2×150 mL), then dried over Na2SO4 and filtered. The filtrate was concentrated in vacuo to afford ethyl 4-(hydroxymethyl)-piperidine-1-carboxylate (B2) as a viscous, pale bluish-green oil (15.60 g, 96% yield). 1H-NMR (400 MHz, CDCl$_3$) δ 4.15 (br m, 2H), 4.09 (q, J=7.1 Hz, 2H), 3.46 (d, J=6.4 Hz, 2H), 2.72 (br t, J=12.4 Hz, 2H), 2.07 (s, 1H), 1.70 (m, 2H), 1.63 (m, 1H), 1.23 (t, J=7.2 Hz, 3H), 1.12 (m, 2H); LC/MS m/z 188.0 [M+H]+, retention time 1.56 min (RP-C18, 10-99% CH$_3$CN/0.05% TFA).

A solution of oxalyl chloride (12.69 g, 0.10 mol) in dichloromethane (150 mL) was cooled to approximately −78° C. and treated dropwise under nitrogen with a solution of anhydrous dimethylsulfoxide (15.63 g, 0.20 mol) in dichloromethane (50 mL). 15 min after the addition was complete, a solution of ethyl 4-(hydroxymethyl)-piperidine-1-carboxylate (15.60 g, 83.3 mmol) (B2) in dichloromethane (50 mL) was added dropwise. 30 minutes after the addition was complete, a solution of triethylamine (25.30 g, 0.25 mol) in dichloromethane (50 mL) was added dropwise and the reaction warmed to room temperature. The reaction was stirred at room temperature for 1 hour, then quenched with saturated sodium bicarbonate (500 mL). The layers were separated and the aqueous layer extracted once with dichloromethane (200 mL). The pooled organic layers were washed with water (3×100 mL), saturated sodium bicarbonate (1×100 mL) and saturated brine (1×100 mL), then dried over Na$_2$SO$_4$ and filtered. The filtrate was concentrated in vacuo to afford ethyl 4-formylpiperidine-1-carboxylate (B3) as a viscous amber oil. 1H-NMR (400 MHz, CDCl$_3$) δ 9.64 (s, 1H), 4.10 (q, J=7.2 Hz, 2H), 4.00 (br m, 2H), 2.97 (m, 2H), 2.40 (m, 1H), 1.87 (br m, 2H), 1.54 (m, 2H), 1.23 (t, J=7.0 Hz, 3H).

Dry chlorine gas was bubbled into the stirring CS$_2$ (C1) (1000 mL, added about 1.0 g of iodine) at 5° C. for 48 hours. The excess CS$_2$ (C1) was evaporated off and the residue was distilled fractionally to give trichloromethyl hypochlorothioite (C2) (bp 144-145° C./1 atm, 300 g, 10%). $^{13}$C-NMR (300 MHz, CDCl3) δ 96.69 (1 C).

To a suspension of trichloromethyl hypochlorothioite (C2) (60 g, 323 mmol) and acetamidine hydrochloride (30.6 g, 323 mmol) in dichloromethane (200 mL) was added dropwise a solution of NaOH (64.8 g in water (200 mL) at −5° C. The resulting mixture was stirred at −5° C. for 30 min and then allowed to warm to room temperature. The organic layer was separated and the aqueous phase was extracted with dichloromethane (30 mL×3). The combined organic layers were washed with water (50 mL×2) and brine (100 mL), dried over Na$_2$SO$_4$ and the solvent was removed. The residue was distilled under reduced pressure to give 5-chloro-3-methyl-1,2,4-thiadiazole (C3) (bp 70° C./0.85 Mpa, 18 g). 1H-NMR (300 MHz, CDCl3) δ 2.59 (s, 3H).

Preparation D: Synthesis of 1-(3-methyl-1,2,4-thiadiazol-5-yl)piperidin-4-one

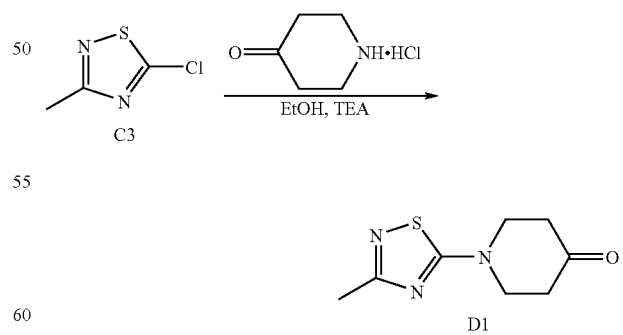

To a mixture of piperidin-4-one HCl salt (C3) (4.08 g, 30 mmol) and Et$_3$N (20 mL, 78.6 mmol) in EtOH (50 mL) was added 5-chloro-3-methyl-1,2,4-thiadiazole (4.05 g, 30 mmol). The mixture was heated to reflux for 1.5 h and then concentrated to dryness. The residue was dissolved in EtOAc.

The solution was washed with water (30 mL×3) and brine (30 mL), dried over Na₂SO₄, and concentrated to dryness. The residue was recrystallized from ether to give 1-(3-methyl-1,2,4-thiadiazol-5-yl)piperidin-4-one (D1) (510 mg). ¹H-NMR (300 MHz, CDCl₃) δ 3.86 (t, J=6.3 Hz, 4H), 2.62 (t, J=6.3, Hz, 4H), 2.44 (s, 3H).

Example 1

Synthesis of ethyl-4-((2-oxo-1,2-dihydrospiro[benzo[d][1,3]oxazine-4,4'-piperidine]-1'-yl)methyl)piperidine-1-carboxylate (Compound No. 13)

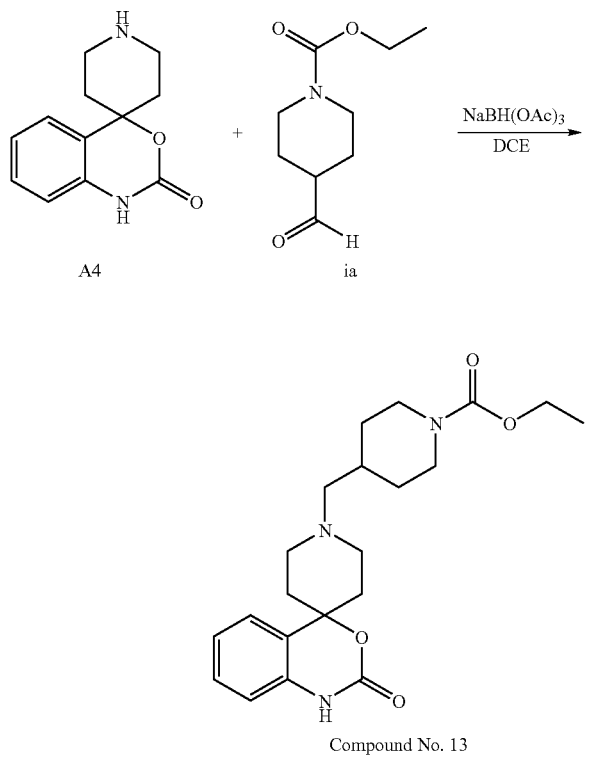

A scintillation vial was charged with spiro[benzo[d][1,3]oxazine-4,4'-piperidin]-2(1H)-one (A4) (22 mg, 0.10 mmol), ethyl-4-formylpiperidine-1-carboxylate 1b (ia) (19 mg) and anhydrous 1,2-dichloroethane (1.0 mL) and treated with sodium triacetoxyborohydride (30 mg). The reaction was stirred at room temperature for 2 hours, then quenched with methanol (1.0 mL) and stirred for 30 minutes. The reaction mixture was concentrated under reduced pressure and the residue obtained dissolved in DMSO:methanol (1.5 mL, 1:1 v/v), filtered (Whatman 0.2 µm PTFE) and subjected to reverse-phase HPLC purification [2-99% CH₃CN gradient over 13 min with 0.1% TFA (aq), 35 mL/min, 1.0 mL injected] to provide ethyl-4-((2-oxo-1,2-dihydrospiro[benzo[d][1,3]oxazine-4,4'-piperidine]-1'-yl)methyl)piperidine-1-carboxylate (compound no. 13) as a TFA salt. LC/MS m/z 388.2 [M+H]⁺, retention time 1.73 min (RP-C18, 10-99% CH₃CN/0.05% TFA).

Example 2

Synthesis of 1'-(bicyclo[3.2.1]octan-3-yl)spiro[benzo[d][1,3]oxazine-4,4'-piperidin]-2(1H)-one (Compound No. 67)

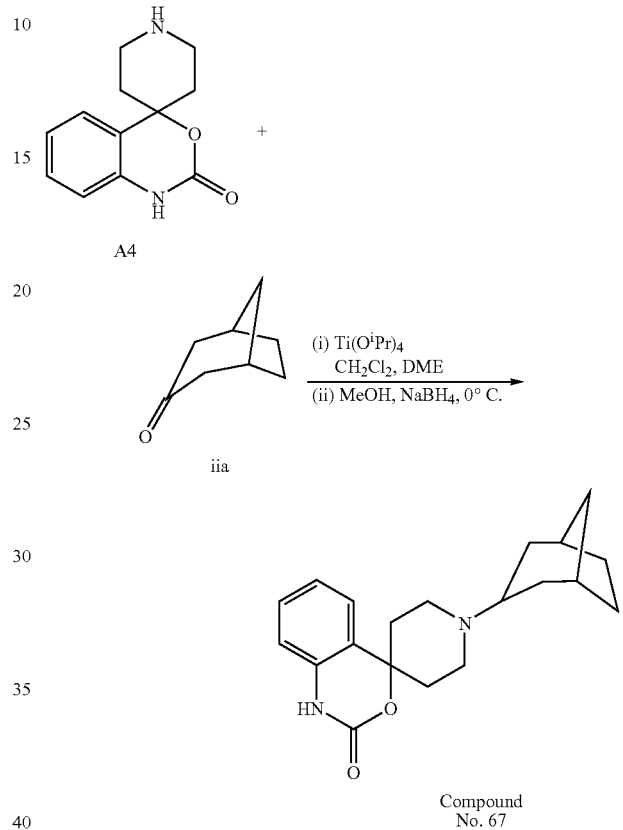

A scintillation vial was charged with bicyclo-[3.2.1]octan-3-one (iia) (31 mg, 0.25 mmol), spiro[4H-3,1-benzoxazine-4,4'-piperidin]-2(1H)-one (A4) (44 mg, 0.20 mmol), and anhydrous dimethoxyethane:dichloromethane (1.0 mL, 1:1 v/v). The mixture was treated with titanium tetraisopropoxide (171 mg, 0.60 mmol). The vial was flushed with nitrogen and stirred at room temperature for 60 hours. The reaction was then cooled in an ice water bath, quenched with methanol (1.0 mL) and treated with sodium borohydride (15 mg, 0.40 mmol). The reaction mixture was slowly warmed to room temperature, stirred for 1 hour, treated with 1.0 N NaOH (1.0 mL), diluted with methanol (2.0 mL), and stirred at room temperature for 15 min. The suspension obtained was centrifuged (3K rpm, 10 min), and the supernatant was filtered (Whatman 0.2 µm PTFE). The filtrate was concentrated under reduced pressure and the residue obtained dissolved in DMSO:methanol (1.5 mL, 1:1 v/v), filtered and subjected to reverse-phase HPLC purification [2-99% CH₃CN gradient over 13 min with 0.1% TFA (aq), 35 mL/min, 1.0 mL injected] to provide 1'-(bicyclo[3.2.1]octan-3-yl)spiro[benzo[d][1,3]oxazine-4,4'-piperidin]-2(1H)-one (compound no. 67) as a TFA salt. LC/MS m/z 327.2 [M+H]+, retention time 1.80 min (RP-C18, 10-99% CH3CN/0.05% TFA).

Example 3

Synthesis of 1'-cycloheptylspiro[benzo[d][1,3]oxazine-4,4'-piperidin]-2(1H)-one (Compound No. 5)

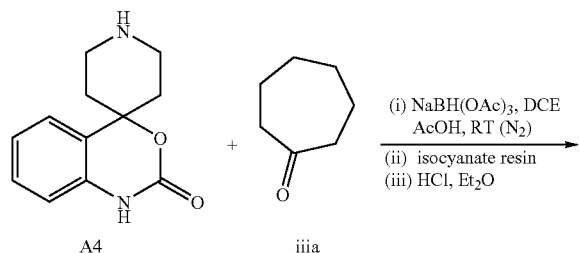

Spiro[4H-3,1-benzoxazine-4,4'-piperidin]-2(1H)-one (A4) (353 mg, 1.62 mmol) was dissolved in anhydrous 1,2-dichloroethane (10 mL) and treated with cycloheptanone (iiia) (273 mg, 2.43 mmol), followed by glacial acetic acid (195 mg, 3.24 mmol) and sodium triacetoxyborohydride (687 mg, 3.24 mmol). The reaction was stirred at room temperature under nitrogen for 90 hours. The reaction was diluted with dichloromethane (50 mL), quenched with 1.0 N NaOH (20 mL), and stirred vigorously at room temperature for 30 minutes. The layers were separated and the aqueous layer was extracted with dichloromethane (2×20 mL). The pooled organic layers were washed with (20 mL each) water and saturated brine; and dried over $Na_2SO_4$ and filtered. The filtrate was concentrated under reduced pressure to afford crude 1'-cycloheptylspiro[benzo[d][1,3]oxazine-4,4'-piperidin]-2(1H)-one as an off-white solid.

The crude product from above was dissolved in anhydrous dichloromethane (5 mL), cooled in an ice water bath and treated with isocyanate resin (345 mg, loading=1.1 mmol/g, 0.38 mmol). The suspension was then treated with triethylamine (38 mg, 0.38 mmol), warmed to room temperature and stirred overnight. The reaction mixture was diluted with dichloromethane (25 mL), then it was filtered and rinsed with dichloromethane (3×10 mL). The filtrate was washed successively with (10 mL each) water, saturated $NaHCO_3$ and saturated brine, then dried over $Na_2SO_4$ and filtered. The filtrate was concentrated under reduced pressure to afford the crude free base as a white solid. The crude free base was dissolved in anhydrous diethyl ether (20 mL) and absolute ethanol (4 mL) and treated dropwise with 1.0 N HCl in diethyl ether (1.7 mL, 1.7 mmol). The suspension obtained was diluted with ether (10 mL) and stirred vigorously at room temperature for 10 minutes. The suspension was further diluted with hexanes (10 mL), cooled in an ice water bath for 10 minutes, then filtered and rinsed with ether (2×10 mL) and hexanes (2×10 mL). The solids were dried under reduced pressure to afford 1'-cycloheptylspiro[benzo[d][1,3]oxazine-4,4'-piperidin]-2(1H)-one (compound no. 5) hydrochloride as a white powder. LC/MS m/z 315.0 [M+H]+, retention time 1.68 min (RP-C18, 10-99% $CH_3CN$/0.05% TFA); 1H-NMR (400 MHz, DMSO-d6) δ 10.95 (br s, 1H), 10.41 (br s, 1H), 7.30 (m, 1H), 7.19 (d, J=7.0 Hz, 1H), 7.09 (m, 1H), 6.93 (d, J=8.0 Hz, 1H), 3.42 (m, 2H), 3.23 (m, 2H), 2.72 (m, 2H), 2.18 (m, 4H), 1.70 (m, 4H), 1.50 (m, 6H).

Example 4

Synthesis of 1'-cycloheptyl-1-methylspiro[benzo[d][1,3]oxazine-4,4'-piperidin]-2(1H)-one (Compound No. 65)

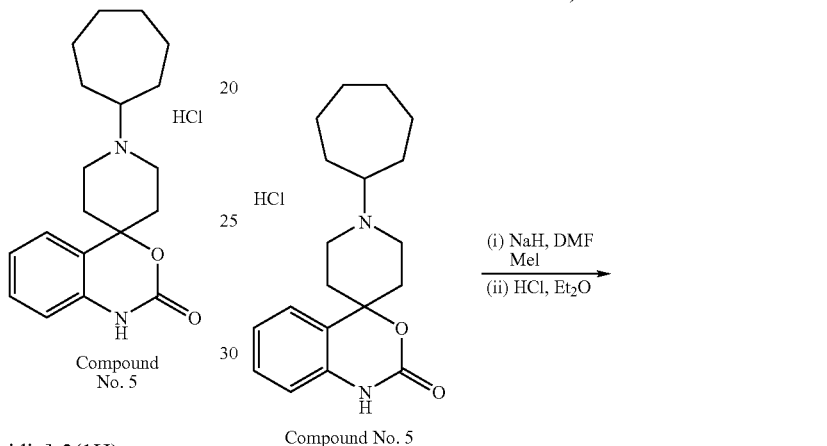

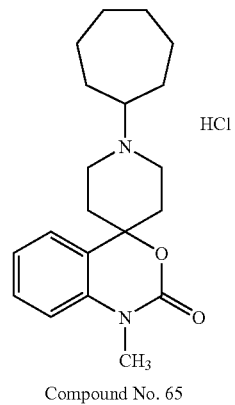

1'-cycloheptylspiro[benzo[d][1,3]oxazine-4,4'-piperidin]-2(1H)-one hydrochloride (compound No. 5) (188 mg, 0.54 mmol) was suspended in anhydrous dimethylformamide (4.0 mL), treated with sodium hydride (48 mg, 60% dispersion in mineral oil, 1.2 mmol) and stirred at room temperature for 10 minutes under nitrogen. The reaction mixture was then treated with a solution of methyl iodide (92 mg, 0.65 mmol) in anhydrous dimethylformamide (1.0 mL) and stirred at room temperature for 1 hour. The reaction mixture was diluted with water (50 mL), and the product was extracted in dichloromethane (2×50 mL). The pooled extracts were washed with water (2×10 mL), saturated $NaHCO_3$, (2×10 mL) and saturated brine (2×10 mL); then dried over $Na_2SO_4$ and filtered. The filtrate was concentrated under reduced pressure to afford crude 1'-cycloheptyl-1-methylspiro[benzo[d][1,3]oxazine-4,4'-piperidin]-2(1H)-one (compound no. 65) free base as a colorless oil.

The crude free base (801 mg) was dissolved in anhydrous diethyl ether (5 mL) and absolute ethanol (0.5 mL) and treated dropwise with 1.0 N HCl in diethyl ether (600 µL, 0.60 mmol). The suspension obtained was diluted with ether (5 mL) and stirred vigorously at room temperature for 10 minutes. The suspension was further diluted with hexanes (5 mL), cooled in an ice water bath for 10 minutes, and filtered and rinsed with ether (5 mL) and hexanes (5 mL). The solids were dried under reduced pressure to afford 1'-cycloheptyl-1-methylspiro[benzo[d][1,3]oxazine-4,4'-piperidin]-2(1H)-one (compound no. 65) hydrochloride as a white solid. LC/MS m/z 329.4 [M+H]+, retention time 1.88 min (RP-C18, 10-99% CH$_3$CN/0.05% TFA); 1H-NMR (400 MHz, DMSO-d6) δ 10.86 (br s, 1H), 7.43 (m, 1H), 7.20 (m, 3H), 3.39 (m, 3H), 3.31 (s, 3H), 3.23 (m, 2H), 2.71 (m, 2H), 2.23 (br d, J=14.4 Hz, 2H), 2.13 (m, 2H), 1.69 (m, 4H), 1.51 (m, 6H).

Example 5

Synthesis of 1'-isopentylspiro[benzo[d][1,3]oxazine-4,4'-piperidin]-2(1H)-one (Compound No. 76)

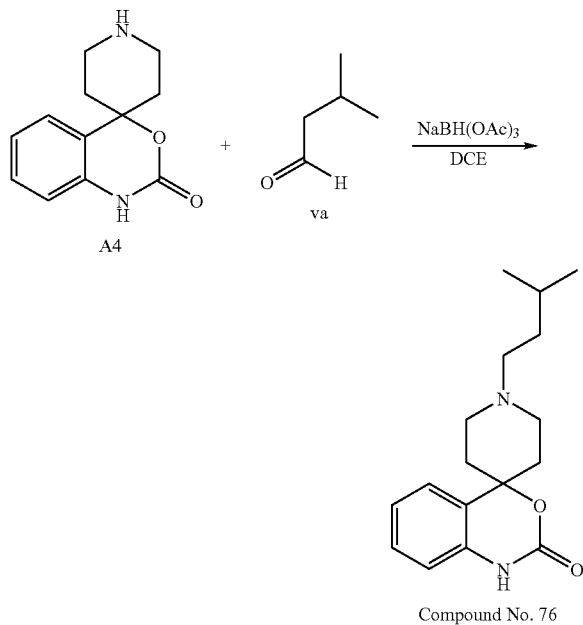

Example 6

Synthesis of 1'-(piperidin-4-yl)spiro[benzo[d][1,3]oxazine-4,4'-piperidin]-2(1H)-one (Compound No. 49)

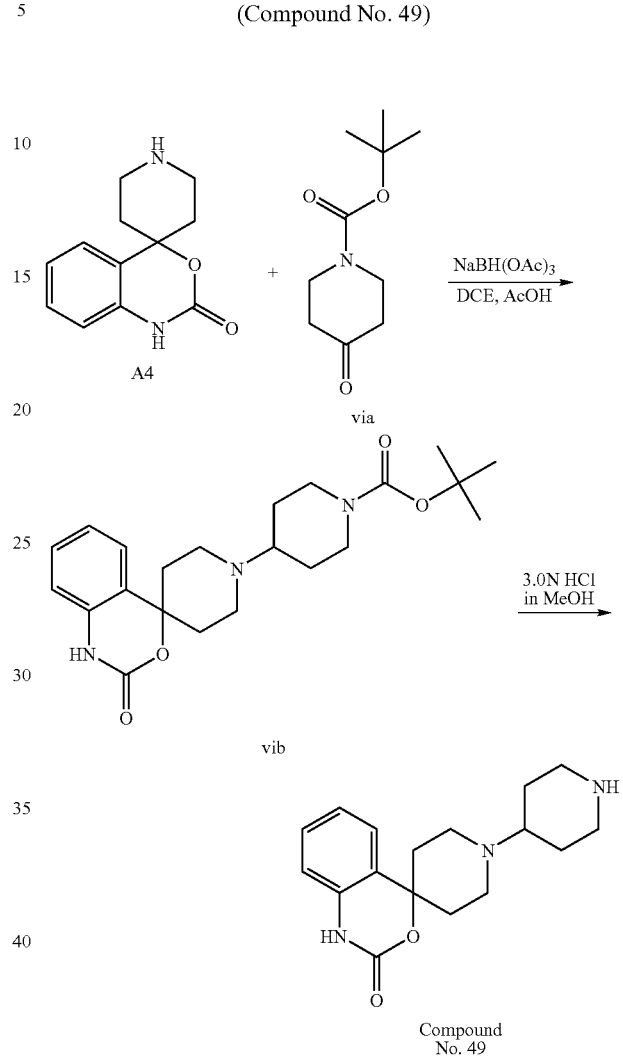

Spiro[4H-3,1-benzoxazine-4,4'-piperidin]-2(1H)-one (A4) (22 mg, 0.10 mmol) was dissolved in anhydrous 1,2-dichloroethane (750 µL) in a scintillation vial and treated with 3-methylbutanal (va) (9 mg, 0.10 mmol), followed by sodium triacetoxyborohydride (30 mg, 0.14 mmol). The reaction was stirred at room temperature for 1 hour, then quenched with methanol (500 µL) and stirred at room temperature for an additional 30 minutes. The reaction was filtered (Whatman 0.45 µm PTFE) and subjected to reverse-phase HPLC purification [2-99% CH3CN gradient over 13 min with 0.1% TFA (aq), 35 mL/min, 1.0 mL injected] to provide 1'-isopentylspiro[benzo[d][1,3]oxazine-4,4'-piperidin]-2(1H)-one (compound no. 76). LC/MS m/z 289.0 [M+H]+, retention time 1.55 min (RP-C18, 10-99% CH$_3$CN/0.05% TFA).

Spiro[4H-3,1-benzoxazine-4,4'-piperidin]-2(1H)-one (A4) (410 mg, 1.88 mmol) was dissolved in anhydrous 1,2-dichloroethane (10 mL) and treated with tert-butyl 4-oxopiperidine-1-carboxylate (via) (562 mg, 2.82 mmol), glacial acetic acid (226 mg, 3.76 mmol) and sodium triacetoxyborohydride (797 mg, 3.76 mmol). The reaction was stirred under nitrogen at room temperature for 72 hours. The reaction was concentrated under reduced pressure and the residue partitioned between 1.0 N HCl (50 mL) and diethyl ether (25 mL). The aqueous layer was separated and washed with diethyl ether (2×25 mL), basified with 1.0 N NaOH (aq) and extracted with dichloromethane (3×50 mL). The pooled extracts were washed with saturated brine, dried over Na2SO4 and filtered. The filtrate was concentrated in vacuo to afford tert-butyl 4-(2-oxo-1,2-dihydrospiro[benzo[d][1,3]oxazine-4,4'-piperidine]-1'-yl)piperidine-1-carboxylate (vib) as a crystalline white solid. LC/MS m/z 402.2 [M+H]+, retention time 1.84 min (RP-C18, 10-99% CH3CN/0.05% TFA).

tert-Butyl 4-(2-oxo-1,2-dihydrospiro[benzo[d][1,3]oxazine-4,4'-piperidine]-1'-yl)piperidine-1-carboxylate (vib)

(432 mg, 1.08 mmol) was dissolved in 3.0 N methanolic HCl (10 mL) and stirred at room temperature for 18 hours. Additional 3.0 N methanolic HCl was added (10 mL) and the reaction heated at 60° C. for 2 hours. The reaction mixture was concentrated under reduced pressure, treated with acetonitrile (approx. 25 mL) and re-concentrated to afford 1'-(piperidin-4-yl)spiro[benzo[d][1,3]oxazine-4,4'-piperidin]-2 (1H)-one (compound no. 49) bis-hydrochloride as a crystalline white solid. LC/MS m/z 302.0 [M+H]+, retention time 0.34 min (RP-C18, 10-99% CH₃CN/0.05% TFA).

Example 7

Synthesis of 1'-(1-(pyrazin-2-yl)piperidin-4-yl)spiro[benzo[d][1,3]oxazine-4,4'piperidin]-2(1H)-one (Compound No. 74)

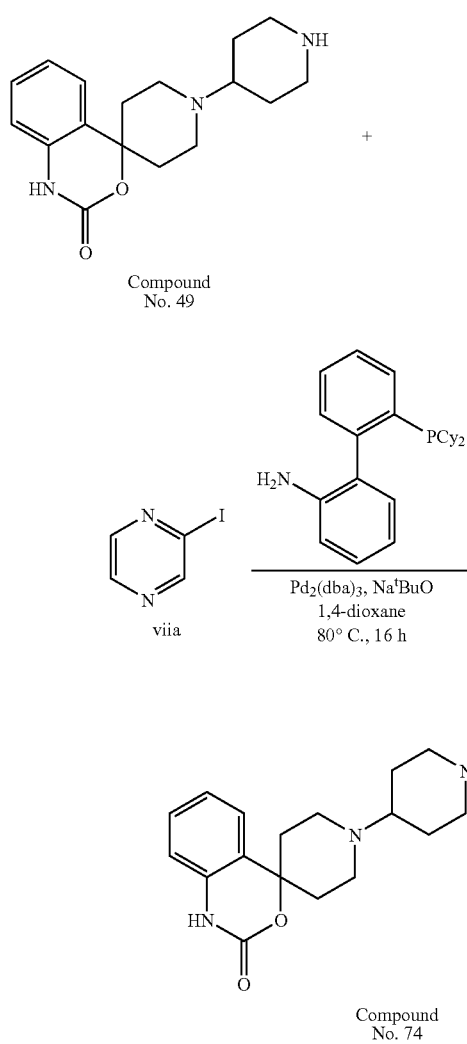

Pd₂(dba)3-CHCl₃ (5 mg, 0.5 mol %), 2'-(dicyclohexylphosphino)biphenyl-2-amine (8 mg, 2 mol %) and sodium tert-butoxide (13 mg, 0.14 mmol) were weighed in air and transferred into flask, followed by dioxane (750 µL), 1'-(piperidin-4-yl)spiro[benzo[d][1,3]oxazine-4,4'piperidin]-2 (1H)-one bis-hydrochloride (compound no. 49) (37 mg, 0.10 mmol) and iodopyrazine (viia) (20.6 mg, 0.10 mmol). The flask was flushed with nitrogen and stirred at 80° C. for 16 hours. The reaction mixture was diluted with methanol (500 µL), filtered (Whatman 0.45 µm PTFE) and subjected to reverse-phase HPLC purification (2-25% CH3CN gradient [w/0.1% TFA (aq)] over 10 minutes, 1.0 mL injected, 35 mL/min) to provide 1'-(1-(pyrazin-2-yl)piperidin-4-yl)spiro [benzo[d][1,3]oxazine-4,4'-piperidin]-2(1H)-one (compound no. 74). LC/MS m/z 380.2 [M+H]+, retention time 1.35 min (RP-C18, 10-99% CH₃CN/0.05% TFA).

Example 8

Synthesis of 1'-(4-oxocyclohexyl)spiro[benzo[d][1,3]oxazine-4,4'-piperidin]-2(1H)-one (Compound No. 64), and 1'-(4-(ethoxyimino)cyclohexyl)spiro[benzo[d][1,3]oxazine-4,4'-piperidin]-2(1H)-one (Compound No. 3)

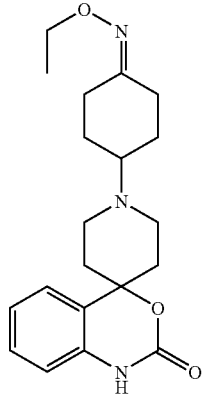

Compound No. 3

Spiro[4H-3,1-benzoxazine-4,4'-piperidin]-2(1H)-one (A4) (400 mg, 1.83 mmol) was suspended in anhydrous 1,2-dichloroethane (8.0 mL) and treated with 1,4-cyclohexanedione mono-ethylene ketal (viia) (429 mg, 2.75 mmol), glacial acetic acid (220 mg, 3.66 mmol), and sodium triacetoxyborohydride (776 mg, 3.66 mmol). The reaction flask was flushed with nitrogen and stirred for 60 hours at room temperature. The reaction was diluted with dichloromethane (25 mL), quenched with 1.0 N NaOH (10 mL), and stirred at room temperature vigorously for 30 minutes. The layers were separated and the aqueous layer was extracted once with dichloromethane (10 mL). The pooled organic layers were washed with water (1×25 mL) and saturated brine (1×25 mL), dried over $Na_2SO_4$ and filtered. The filtrate was concentrated under reduced pressure to afford crude 1'-(1,4-dioxaspiro[4.5]decan-8-yl)spiro[benzo[d][1,3]oxazine-4,4'-piperidin]-2(1H)-one (viiib) as a white solid. LC/MS m/z 359.2 [M+H]+, retention time 1.61 min (RP-C18, 10-99% CH3CN/0.05% TFA).

The crude 1'-(1,4-dioxaspiro[4.5]decan-8-yl)spiro[benzo[d][1,3]oxazine-4,4'-piperidin]-2(1H)-one (viiib) (712 mg) was dissolved in 80% glacial acetic acid (aq) (25 mL) and heated at ~110° C. for 5 hours. After cooling to room temperature, the reaction was diluted with water (25 mL), cooled in an ice water bath, and slowly neutralized with ice-cold 6.0 N NaOH (aq) (adjusted to ~pH 10-11) to give a white precipitate. The product was extracted in dichloromethane (2×50 mL). The pooled extracts were washed with water (1×25 mL) and saturated brine (1×25 mL), dried over $Na_2SO_4$ and filtered. The filtrate was concentrated under reduced pressure to afford 1'-(4-oxocyclohexyl)spiro[benzo[d][1,3]oxazine-4,4'-piperidin]-2(1H)-one (compound No. 64) as shiny white needles. LC/MS m/z 315.0 [M+H]+, retention time 0.76 min (RP-C18, 10-99% $CH_3CN$/0.05% TFA). 1H-NMR (400 MHz, DMSO-d6) δ 10.19 (s, 1H), 7.30 (d, J=7.6 Hz, 1H), 7.24 (dt, J=10.6, 3.9 Hz, 1H), 7.02 (dt, J=10.4, 3.8 Hz, 1H), 6.89 (dd, J=7.9, 0.9 Hz, 1H), 2.82-2.79 (m, 3H), 2.60 (dt, J=16.3, 5.5 Hz, 2H), 2.42-2.26 (m, 4H), 2.06-1.93 (m, 6H), 1.85-1.75 (m, 2H).

1'-(4-oxocyclohexyl)spiro[benzo[d][1,3]oxazine-4,4'-piperidin]-2(1H)-one (Compound No. 64) (31 mg, 0.10 mmol) was dissolved in anhydrous pyridine (500 μL), treated with of O-ethylhydroxylamine hydrochloride (7 mg, 0.12 mmol) and stirred at 60° C. for 30 minutes. The reaction was cooled to room temperature, diluted with methanol (500 μL) and subjected to reverse-phase HPLC purification (2-30% $CH_3CN$ gradient [w/0.1% TFA (aq)] over 10 minutes, 1.0 mL injected, 35 mL/min) to provide 1'-(4-(ethoxyimino)cyclohexyl)spiro[benzo[d][1,3]oxazine-4,4'-piperidin]-2(1H)-one (compound no. 3). LC/MS m/z 358.0 [M+H]+, retention time 1.64 min (RP-C18, 10-99% $CH_3CN$/0.05% TFA).

Known synthetic methodologies, the schemes, and examples can be used to synthesize compounds of the present invention, including the compounds in Table 2 below.

TABLE 2

Physical data for exemplary compounds of formulae (I, Ia, Ib, Ic, and Id)

| Compound No. | LCMS_Plus | LCMS_RT |
|---|---|---|
| 1 | 400 | 1.73 |
| 2 | 327.2 | 1.8 |
| 4 | 315.2 | 2.14 |
| 6 | 388.4 | 2.05 |
| 7 | 303.4 | 0.84 |
| 8 | 343.2 | 2.39 |
| 9 | 341.2 | 2.18 |
| 10 | 353.4 | 2.23 |
| 11 | 317.4 | 1.23 |
| 12 | 315.2 | 2.03 |
| 14 | 319 | 1.34 |
| 15 | 313 | 1.61 |
| 16 | 312.8 | 1.62 |
| 17 | 328.8 | 1.85 |
| 18 | 342.8 | 2.02 |
| 19 | 357.2 | 2.18 |
| 20 | 357.5 | 2.21 |
| 21 | 371.2 | 2.36 |
| 22 | 353.2 | 2.09 |
| 23 | 341 | 2.04 |
| 24 | 353.2 | 2.16 |
| 25 | 303.2 | 0.73 |
| 26 | 317 | 1.23 |
| 27 | 313 | 1.83 |
| 28 | 273.2 | 1.11 |
| 29 | 301 | 1.66 |
| 30 | 309.2 | 1.67 |
| 31 | 273.2 | 1.01 |
| 32 | 287.2 | 1.28 |
| 33 | 301 | 1.58 |
| 34 | 331 | 1.68 |
| 35 | 369 | 1.82 |
| 36 | 369.2 | 1.82 |
| 37 | 315 | 1.73 |
| 38 | 315 | 1.7 |
| 39 | 315 | 1.69 |
| 40 | 328.8 | 1.92 |
| 41 | 343.2 | 2.09 |
| 42 | 357.2 | 2.24 |
| 43 | 371.2 | 2.35 |
| 44 | 383.2 | 2.47 |
| 45 | 369.2 | 2.26 |
| 46 | 355 | 2.1 |
| 47 | 377.2 | 2.14 |
| 48 | 402.2 | 2.05 |
| 50 | 344.2 | 0.69 |
| 51 | 406.2 | 1.67 |
| 52 | 359.2 | 1.38 |
| 53 | 401 | 1.81 |
| 54 | 327.2 | 1.88 |
| 55 | 327 | 1.86 |
| 56 | 329.2 | 1.86 |
| 57 | 343 | 2.04 |
| 58 | 327.2 | 1.78 |
| 59 | 315 | 0.81 |
| 60 | 344.2 | 1.46 |
| 61 | 358 | 1.64 |
| 62 | 372.2 | 1.83 |
| 63 | 372.2 | 1.8 |
| 66 | 406.2 | 2.16 |
| 68 | 317 | 0.79 |
| 69 | 355 | 2.1 |
| 70 | 367.2 | 2.19 |
| 71 | 373.2 | 1.98 |

TABLE 2-continued

Physical data for exemplary compounds of formulae (I, Ia, Ib, Ic, and Id)

| Compound No. | LCMS_Plus | LCMS_RT |
|---|---|---|
| 72 | 371.2 | 1.91 |
| 73 | 405.4 | 2.39 |
| 75 | 302 | 0.34 |
| 77 | 360 | 1.25 |
| 78 | 388.2 | 1.7 |
| 79 | 404.4 | 1.41 |
| 80 | 384.2 | 1.52 |
| 81 | 398.2 | 1.64 |
| 82 | 412 | 1.86 |
| 83 | 388.2 | 1.7 |
| 84 | 370 | 1.23 |
| 85 | 219.2 | 0.58 |
| 86 | 247 | 0.52 |
| 87 | 247 | 0.72 |
| 88 | 261.2 | 0.97 |
| 89 | 261.2 | 0.88 |
| 90 | 289 | 1.47 |
| 91 | 303.2 | 1.76 |
| 92 | 289 | 1.54 |
| 93 | 303.2 | 1.7 |
| 94 | 302.4 | 0.82 |
| 95 | 288.2 | 0.7 |
| 96 | 300.2 | 0.64 |
| 97 | 314.2 | 0.75 |
| 98 | 314.2 | 0.82 |
| 99 | 312.2 | 0.72 |
| 100 | 302.2 | 0.35 |
| 101 | 316.2 | 0.42 |
| 102 | 413.2 | 0.77 |
| 103 | 300.2 | 0.74 |
| 104 | 326.4 | 0.89 |
| 105 | 373.2 | 0.69 |
| 106 | 398.2 | 0.72 |
| 107 | 412.3 | 0.84 |
| 108 | 399.4 | 0.79 |

VI. Assays

The muscarinic modulating activity of compounds of formulae (I, Ia, Ib, Ic, and Id) can be assessed by methods described in the following examples.

Functional Mobilization of Intracellular Calcium to Determine Muscarinic Receptor Activity:

CHO cells expressing muscarinic receptors ($M_1$ to $M_5$) are grown as monolayers in tissue culture flasks at 37° C. in a humidified atmosphere containing 5% $CO_2$ and passaged every 3-5 days. The growth media is Dulbecco's modified eagles medium (DMEM, Gibco Cat# 12430-054), containing 25 mM Hepes and supplemented with Fetal Bovine Serum (Hyclone, cat# SH30071.03), 0.1 mM of MEM non-essential amino acids (GIBCO, Cat# 11140-050), 1 mM MEM Sodium Pyruvate (GIBCO Cat# 11360-070) and 100 units/ml of Penicillin G and 100 μg/ml of Streptomycin (GIBCO Cat# 15140-122). The recombinant muscarinic receptor cell lines are grown under antibiotic pressure with media containing 25 μg/ml zeocin and 500 μg/ml G418 ($M_1$-CHO), 4 μg/ml puromycin, 50 μg/ml zeocin and 2.5 μg/ml blasticidin ($M_2$ and $M_4$-CHO) or 50 μg/ml zeocin and 4 μg/ml puromycin ($M_3$ and $M_5$-CHO).

Cells are harvested at 80-90% confluence using Versene (GIBCO Cat# 15040-066), collected by centrifugation and seeded 18-24 hours prior to running the calcium assay at a density of 5,000-10,000 cells/well in back-walled, clear-bottomed 384-well plates (BD Biocoat, poly-D-lysine, Cat#356663). The day of the experiment, the cells are washed with a plate washer (Bioteck Instruments, ELX 405) using Bath 1 buffer (140-mM NaCl, 4.5-mM KCl, 2-mM $CaCl_2$, 1-mM $MgCl_2$, 10-mM Hepes-Na, 10-mM Glucose, pH 7.4, with NaOH) containing 1 mM Probenecid. Next, the calcium dye Fluo-3 (25 μl/well of Fluo-3 AM at 4 μM, Molecular Probes F-1241, in Bath 1 buffer containing 1 mM Probenecid) is added to the 25 μl of Bath 1 remaining in each well after the plate wash and the dye is loaded at 37° C. in the tissue culture incubator for 60-90 min. The fluorescent dye is removed using the plate washer with Bath 1 containing 1 mM Probenecid, leaving 25 μl/well of this solution after the wash. Alternatively, cells can be loaded with the calcium indicator from Molecular Devices (Calcium 3 Assay Reagents, Cat # R7181) adding 5 μl of a 5× solution dye in Bath 1 containing 1 mM Probenecid (10 ml per dye flask cat# R7182 to generate a solution 20×) to 20 μl of the same buffer. After loading for 60 min, the experiment can be run without having to remove the dye.

Compounds are prepared at a 2× fold concentration in a 96-well plate (round bottom, Costar Corning cat# 3656), by reconstituting the pre-spotted compounds in bath 1 containing 1 mM probenecid. The final concentration DMSO is 0.5%, and the amount of DMSO is normalized across the assay plate. To determine an agonist action of the compounds on muscarinic receptors, the reconstituted compounds are added (25 μl compound/well) to the cell assay plate (containing 25 μl/well) using the multi-channel robotic system of the FLIPR 3 Instrument (Molecular Devices, Sunnyvale, Calif.). To determine a functional inhibitory action of the compounds on muscarinic receptors, the reconstituted compounds are added (25 μl compound/well) to the assay plate and pre-incubated for 15 min prior to adding 25 μl of Carbachol at 3× the $EC_{80}$ for each muscarinic subtype. Alternatively, the compounds can be co-applied simultaneously with the agonist. In both assay modes, the fluorescence is recorded for 60 sec (excitation wavelength is 488 nM and emission wavelength 540 nm) using the FLIPR 3 instrument.

The potency, efficacy and selectivity of the muscarinic compounds were evaluated by screening the compound activity across the whole family ($M_1$ to $M_5$ cells). Compounds were also screened for activity on other proteins such as other GPCRs and ion channels to determine selectivity on $M_4$ receptors.

The compounds of the present invention were found to modulate the $M_1$ and/or $M_4$ muscarinic receptors selectively over the other receptor types.

Examples of activities and efficacies of the muscarinic compounds of formulae (I, Ia, Ib, Ic, and Id) on modulating $M_1$ and $M_4$ receptors are shown below in Table 3. The compound activity for the $M_1$ and $M_4$ is illustrated with "+++" if activity was measured to be less than 2.0 μM, "++" if activity was measured to be from 2.0 μM to 5.0 μM, "+" if activity was measured to be greater than 5.0 μM, and "–" if no data was available. The efficacy for $M_1$ and $M_4$ modulation is illustrated with "+++" if efficacy was calculated to be greater than 100%, "++" if efficacy was calculated to be from 100% to 25%, "+" if efficacy was calculated to be less than 25%, and "–" if no data was available. It should be noted that 100% efficacy is the maximum response obtained with the Carbachol control.

TABLE 3

Activities and efficacies of compounds of formulae (I, Ia, Ib, Ic, and Id).

| Cmpd No | $M_1$ Activity | $M_1$ Efficacy | $M_2$ Activity | $M_2$ Efficacy | $M_3$ Activity | $M_3$ Efficacy | $M_4$ Activity | $M_4$ Efficacy |
|---|---|---|---|---|---|---|---|---|
| 1 | ++ | ++ | + | ++ | + | + | ++ | ++ |
| 2 | ++ | ++ | + | + | + | + | + | ++ |
| 3 | +++ | ++ | +++ | ++ | +++ | ++ | +++ | ++ |
| 4 | +++ | ++ | ++ | ++ | + | + | +++ | ++ |
| 5 | +++ | ++ | + | ++ | + | + | +++ | ++ |
| 6 | ++ | ++ | + | + | + | + | + | + |
| 7 | +++ | ++ | +++ | ++ | ++ | ++ | +++ | ++ |
| 8 | +++ | ++ | +++ | ++ | + | ++ | +++ | ++ |
| 9 | +++ | ++ | ++ | ++ | + | + | +++ | ++ |
| 10 | + | + | + | + | + | + | + | + |
| 11 | +++ | ++ | + | ++ | + | + | +++ | ++ |
| 12 | +++ | ++ | + | ++ | + | + | +++ | ++ |
| 13 | +++ | ++ | +++ | ++ | +++ | ++ | +++ | ++ |
| 14 | +++ | ++ | +++ | ++ | +++ | ++ | +++ | ++ |
| 15 | ++ | ++ | + | + | + | + | + | + |
| 16 | +++ | ++ | + | + | + | + | +++ | ++ |
| 17 | +++ | ++ | + | + | + | + | +++ | + |
| 18 | +++ | ++ | + | + | + | + | +++ | ++ |
| 19 | +++ | ++ | + | ++ | + | + | +++ | ++ |
| 20 | + | ++ | + | + | + | + | + | ++ |
| 21 | +++ | ++ | + | + | + | + | +++ | ++ |
| 22 | +++ | ++ | +++ | ++ | + | ++ | +++ | ++ |
| 23 | + | + | + | + | + | + | + | + |
| 24 | +++ | ++ | + | + | + | + | +++ | ++ |
| 25 | +++ | ++ | +++ | ++ | + | ++ | +++ | ++ |
| 26 | +++ | ++ | + | + | + | + | +++ | + |
| 27 | +++ | ++ | ++ | ++ | + | + | +++ | ++ |
| 28 | +++ | ++ | +++ | ++ | ++ | ++ | +++ | ++ |
| 29 | + | + | + | + | + | + | + | + |
| 30 | +++ | ++ | ++ | ++ | + | + | +++ | ++ |
| 31 | ++ | ++ | + | + | + | + | +++ | + |
| 32 | +++ | ++ | ++ | + | + | + | +++ | ++ |
| 33 | + | + | + | + | + | + | +++ | ++ |
| 34 | + | ++ | + | + | + | + | + | + |
| 35 | +++ | ++ | + | + | + | + | + | + |
| 36 | +++ | ++ | +++ | ++ | ++ | ++ | +++ | ++ |
| 37 | + | + | + | + | + | + | +++ | ++ |
| 38 | ++ | ++ | + | ++ | + | + | ++ | ++ |
| 39 | +++ | ++ | ++ | + | + | + | +++ | ++ |
| 40 | +++ | ++ | ++ | + | + | + | +++ | ++ |
| 41 | +++ | ++ | + | + | + | + | +++ | ++ |
| 42 | +++ | ++ | + | + | + | + | +++ | ++ |
| 43 | + | + | + | + | + | + | + | + |
| 44 | +++ | ++ | ++ | ++ | + | + | +++ | ++ |
| 45 | ++ | + | + | + | + | + | + | + |
| 46 | +++ | ++ | +++ | ++ | + | + | +++ | ++ |
| 47 | + | ++ | + | + | + | + | + | + |
| 48 | +++ | ++ | +++ | ++ | + | ++ | +++ | ++ |
| 49 | + | ++ | + | + | + | + | + | + |
| 50 | +++ | ++ | + | ++ | + | + | +++ | ++ |
| 51 | + | + | + | + | + | + | + | + |
| 52 | +++ | ++ | + | + | + | + | ++ | ++ |
| 53 | +++ | ++ | +++ | ++ | + | ++ | +++ | ++ |
| 54 | +++ | ++ | + | + | + | + | + | + |
| 55 | + | ++ | + | + | + | + | + | + |
| 56 | + | ++ | + | + | + | ++ | + | + |
| 57 | +++ | ++ | +++ | ++ | + | + | +++ | ++ |
| 58 | +++ | ++ | + | + | + | + | ++ | ++ |
| 59 | +++ | ++ | + | + | + | + | + | + |
| 60 | +++ | ++ | +++ | ++ | + | ++ | +++ | ++ |
| 61 | +++ | ++ | + | + | + | + | + | + |
| 62 | +++ | ++ | +++ | ++ | +++ | ++ | +++ | ++ |
| 63 | +++ | ++ | +++ | ++ | +++ | ++ | +++ | ++ |
| 64 | ++ | ++ | + | ++ | + | + | ++ | ++ |
| 65 | + | + | + | + | + | + | +++ | ++ |
| 66 | + | ++ | + | + | + | + | + | + |
| 67 | +++ | ++ | +++ | ++ | + | ++ | +++ | ++ |
| 68 | +++ | ++ | + | + | + | + | + | + |
| 69 | +++ | ++ | +++ | ++ | + | ++ | +++ | ++ |
| 70 | +++ | ++ | + | + | + | + | + | + |
| 71 | ++ | ++ | + | + | + | + | +++ | ++ |
| 72 | + | + | + | + | + | + | + | + |
| 73 | + | ++ | + | + | + | + | + | + |
| 74 | +++ | +++ | +++ | ++ | + | ++ | +++ | ++ |

TABLE 3-continued

Activities and efficacies of compounds of formulae (I, Ia, Ib, Ic, and Id).

| Cmpd No | $M_1$ Activity | $M_1$ Efficacy | $M_2$ Activity | $M_2$ Efficacy | $M_3$ Activity | $M_3$ Efficacy | $M_4$ Activity | $M_4$ Efficacy |
|---|---|---|---|---|---|---|---|---|
| 75 | +++ | ++ | + | + | + | + | +++ | ++ |
| 76 | +++ | ++ | + | ++ | + | + | +++ | ++ |
| 77 | +++ | ++ | + | + | + | + | +++ | ++ |
| 78 | ++ | ++ | + | + | + | + | +++ | ++ |
| 79 | +++ | ++ | + | + | + | + | + | + |
| 80 | +++ | ++ | +++ | ++ | + | ++ | +++ | ++ |
| 81 | +++ | ++ | + | ++ | + | + | ++ | ++ |
| 82 | +++ | ++ | ++ | ++ | + | + | +++ | ++ |
| 83 | +++ | ++ | + | + | + | + | +++ | ++ |
| 84 | + | ++ | + | + | + | + | + | + |
| 85 | +++ | ++ | +++ | ++ | + | + | +++ | ++ |
| 86 | +++ | +++ | +++ | ++ | +++ | ++ | +++ | ++ |
| 87 | +++ | ++ | + | + | + | + | ++ | ++ |
| 88 | +++ | ++ | + | + | + | + | +++ | ++ |
| 89 | +++ | ++ | + | ++ | + | + | ++ | ++ |
| 90 | +++ | ++ | ++ | ++ | + | + | + | + |
| 91 | + | + | + | + | + | + | + | + |
| 92 | +++ | ++ | + | + | + | + | ++ | + |
| 93 | +++ | ++ | ++ | ++ | ++ | ++ | + | + |
| 94 | − | − | − | − | − | − | − | − |
| 95 | − | − | − | − | − | − | − | − |
| 96 | − | − | − | − | − | − | − | − |
| 97 | − | − | − | − | − | − | − | − |
| 98 | − | − | − | − | − | − | − | − |
| 99 | − | − | − | − | − | − | − | − |
| 100 | − | − | − | − | − | − | − | − |
| 101 | − | − | − | − | − | − | − | − |
| 102 | − | − | − | − | − | − | − | − |
| 103 | − | − | − | − | − | − | − | − |
| 104 | − | − | − | − | − | − | − | − |
| 105 | − | − | − | − | − | − | − | − |
| 106 | − | − | − | − | − | − | − | − |
| 107 | − | − | − | − | − | − | − | − |
| 108 | − | − | − | − | − | − | − | − |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A compound of formula Ia

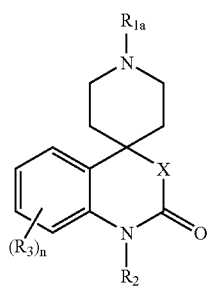

or a pharmaceutically acceptable salt thereof, wherein

X is —$NR_{50}$— or —O—, $R_{50}$ is independently hydrogen or optionally substituted $C_{1-6}$ aliphatic;

Each $R_{1a}$ is a group containing at least four carbon atoms and is independently, aliphatic, cycloaliphatic, heteroaliphatic or heterocycloaliphatic, optionally substituted with aliphatic, cycloaliphatic, heteroaliphatic or heterocycloaliphatic, acyl, alkoxycarbonyl, cycloalkoxycarbonyl, heterocycloalkoxycarbonyl or amido, wherein the alkoxycarbonyl can be further substituted with aliphatic;

$R_2$ is —$Z^B R_5$, wherein each $Z^B$ is independently a bond or an optionally substituted branched or straight $C_{1-6}$ aliphatic chain wherein up to two carbon units of $Z^B$ are optionally and independently replaced by —CO—, —CS—, —$CONR^B$—, —$CONR^B NR^B$—, —$CO_2$—, —OCO—, —$NR^B CO_2$—, —O—, —$NR^B CONR^B$—, —$OCONR^B$—, —$NR^B NR^B$—, —$NR^B CO$—, —S—, —SO—, —$SO_2$—, —$NR^B$—, —$SO_2 NR^B$—, —$NR^B SO_2$—, or —$NR^B SO_2 NR^B$—;

Each $R_5$ is independently $R^B$, halo, —OH, —$NH_2$, —$NO_2$, —CN, or —$OCF_3$; and Each $R^B$ is independently hydrogen, optionally substituted $C_{1-4}$ aliphatic, optionally substituted cycloaliphatic, optionally substituted heterocycloaliphatic, optionally substituted aryl, or an optionally substituted heteroaryl;

Each $R_3$ is independently hydrogen, halo, optionally substituted aliphatic, optionally substituted (aliphatic)oxy, optionally substituted cycloaliphatic, optionally substituted heterocycloaliphatic, optionally substituted aryl, or optionally substituted heteroaryl; and n is 0-4, Provided that when $R_{1a}$ is substituted aliphatic, $R_{1a}$ is substituted with 1-3 of halo, cyano, nitro, hydroxy, —NH$_2$, optionally substituted alkoxy, optionally substituted cycloaliphatic, or optionally substituted heterocyloaliphatic;

when $R_{1a}$ is aliphatic substituted with a monocyclic heterocycloaliphatic, the monocyclic heterocycloaliphatic is not substituted with aryl; and when $R_{1a}$ is optionally substituted cycloaliphatic, $R_{1a}$ is not substituted with a substituted monocyclic heterocycloaliphic.

2. The compound of claim 1, wherein $R_{1a}$ is optionally substituted cycloaliphatic.

3. The compound of claim 2, wherein $R_{1a}$ is monocyclic, bicyclic, or tricyclic cycloaliphatic, each of which is optionally substituted.

4. The compound of claim 3, wherein $R_{1a}$ is optionally substituted 3-8 membered monocyclic cycloaliphatic that is optionally substituted with 1-3 of halo, oxo, oxime, hydroxy, nitro, cyano, or optionally substituted aliphatic, optionally substituted (aliphatic)oxy, optionally substituted (aliphatic(oxy))carbonyl, optionally substituted cycloaliphatic, unsubstituted monocyclic heterocycloaliphatic, optionally substituted bicyclic heterocycloaliphatic, optionally substituted aryl, optionally substituted heteroaryl, or combinations thereof.

5. The compound of claim 4, wherein $R_{1a}$ is cyclopropane-yl, cyclobutane-yl, cyclopentane-yl, cyclohexane-yl, cycloheptane-yl, or cyclooctane-yl, each of which is optionally subsititued with 1-3 of halo, hydroxy, nitro, cyano, aliphatic, oxime, (aliphatic)carbonyl, (aliphatic)oxy, carboxy, cycloaliphatic, unsubstituted monocyclic heterocycloaliphatic, aryl, heteroaryl, or combinations thereof.

6. The compound of claim 3, wherein $R_{1a}$ is bridged bicyclic cycloaliphatic, fused bicyclic cycloaliphatic, or spiro bicyclic cycloaliphatic, each of which is optionally substituted.

7. The compound of claim 6, wherein $R_{1a}$ is optionally substituted 6-9 membered bridged bicyclic cycloaliphatic.

8. The compound of claim 7, wherein $R_{1a}$ is bicyclo[2.1.1]hexane-yl, bicyclo[3.1.0]hexane-yl, bicyclo[2.2.1]heptane-yl, bicyclo[2.2.2]octane-yl, bicyclo[3.1.1]heptane-yl, bicyclo[3.2.1]octane-yl, or bicyclo[3.3.1]nonane-yl, each of which is optionally substituted with 1-3 of halo, hydroxy, nitro, cyano, aliphatic, alkoxycarbonyl, cycloaliphatic, heterocycloaliphatic, aryl, heteroaryl, or combinations thereof.

9. The compound of claim 3, wherein $R_{1a}$ is optionally substituted 6-10 membered fused bicyclic cycloaliphatic.

10. The compound of claim 9, wherein $R_{1a}$ is octahydropentalene-yl, octahydro-1H-indene-yl, or decahydronaphthalene-yl, each of which is optionally substituted with 1-3 of halo, hydroxy, nitro, cyano, aliphatic, alkoxycarbonyl, cycloaliphatic, heterocycloaliphatic, aryl, heteroaryl, or combinations thereof.

11. The compound of claim 3, wherein $R_{1a}$ is optionally substituted 9-12 membered spiro bicyclic cycloaliphatic.

12. The compound of claim 11, wherein $R_{1a}$ is spiro[5.5]undecane-yl, spiro[4.5]decane-yl, or spiro[5.6]dodecane-yl, each of which is optionally substituted.

13. The compound of claim 3, wherein $R_{1a}$ is optionally substituted adamantyl.

14. The compound of claim 1, wherein $R_{1a}$ is optionally substituted heterocycloaliphatic.

15. The compound of claim 14, wherein $R_{1a}$ is optionally substituted monocyclic or bicyclic heterocycloaliphatic having 1-3 heteroatoms independently selected from N, O, and S.

16. The compound of claim 15, wherein $R_{1a}$ is optionally substituted 4-8 membered monocyclic heterocycloaliphatic having 1-3 heteroatoms independently selected from N, O, and S.

17. The compound of claim 16, wherein $R_{1a}$ is tetrahydrofuran-yl, pyrroline-yl, pyrrolidine-yl, 1,3-dioxolane-yl, imidazolidine-yl, 2-imidazoline-yl, pyrazoline-yl, pyrazolidine-yl, tetrahydropyranyl, piperidine-yl, 1,4-dioxane-yl, morpholine-yl, 1,4-dithiane, thiomorpholine, or piperazine-yl, each of which is optionally subsititued with 1-3 of halo, hydroxy, nitro, cyano, aliphatic, (aliphatic(oxy))carbonyl, cycloaliphatic, heterocycloaliphatic, heteroaryl, (aliphatic)heteroaryl, (aliphatic)heterocycloaliphatic, (aliphatic)carbonyl, or combinations thereof.

18. The compound of claim 14, wherein $R_{1a}$ is optionally substituted 6-9 membered bridged bicyclic heterocycloaliphatic.

19. The compound of claim 18, wherein $R_{1a}$ is 5-azabicyclo[2.1.1]hexane-yl, 7-azabicyclo[2.2.]heptane-yl, or 8-azabicyclol[3.2.1]octane-yl, each of which is optionally substituted with 1-3 of halo, hydroxy, nitro, cyano, aliphatic, alkoxycarbonyl, cycloaliphatic, heterocycloaliphatic, aryl, heteroaryl, or combinations thereof.

20. The compound of claim 14, wherein $R_{1a}$ is optionally substituted 9-12 membered spiro bicyclic heterocycloaliphatic.

21. The compound of claim 20, wherein $R_{1a}$ is 1,4-dioxaspiro[4.5]decane-yl; 1,4-dioxaspiro[4.4]nonane-yl; 1,5-dioxaspiro[5.5]undecane-yl; or 6,10-dioxaspiro[4.5]decane-yl; each of which is optionally substituted.

22. The compound of claim 1, wherein $R_{1a}$ is optionally substituted aliphatic.

23. The compound of claim 22, wherein $R_{1a}$ is optionally substituted straight or branched $C_{1-8}$ aliphatic.

24. The compound of claim 23, wherein $R_{1a}$ is butyl, sec-butyl, tert-butyl, pentyl, isopentyl, or neohexyl, each of which is optionally substituted with 1-3 of halo, oxo, or optionally substituted alkoxy, optionally substituted amino, optionally substituted aliphaticsulfonyl, optionally substituted cycloaliphatic, optionally substituted heterocycloaliphatic, or combinations thereof.

25. The compound of claim 1, wherein $R_{1a}$ is one selected from hydrogen; tetrahydrofuran-3-yl-methyl; 4-(hydroxy)cyclohexyl; 4-(ethoxy(imino)cyclohexyl; cyclohexyl; cycloheptanyl; N-(methyl(carbonyl))piperidyl; (bicyclo[2.2.1]hept-2-yl)methyl; 3-(methyl)cyclohexyl; bicyclo[2.2.1]heptyl; isopropyl; tetrahydro-2H-pyran-3-yl; N-(but-3-ynyl(oxy(carbonyl)))piperidine-4-yl; N-(ethoxy(carbonyl(piperidine-4-yl)methyl; 4-propylcyclohexyl; 2-methoxycyclohexyl; 4-(phenyl(methyl(oxy(imino))))cyclohexyl; cycloheptyl; N-(isopropyl(oxy(carbonyl)))piperidine-4-yl; 4-(cyclohexane-yl)cyclohexyl; (cyclopropane-yl)methyl; cyclooctyl; 4-(methoxy(imino))cyclohexyl; N-(propoxy(carbonyl))piperidine-4-yl; N-(pent-2-ynyl(oxy(carbonyl)))piperidine-4-yl; 4-(tertbutyl(oxy(imino)))cyclohexyl; (cyclohexyl)methyl; 4-(ethyl)cyclohexyl; 2,6,6-(trimethyl(cyclohexa-1,3-diene-yl))methyl; N-(methoxy(ethoxy(carbonyl)))piperidine-4-yl; decahydronaphthalene-2-yl; 1,1-dimethylpropyl; propyl; 4-(ethoxy(carbonyl))cyclohexyl; tetrahydro-2H-pyran-4-yl; 3-(methyl)cyclopentyl; 4-(methyl)cyclohexyl; 2-(ethyl)butyl; 4,4-(dimethyl)cyclohex-2-ene-yl; ethyl; bicyclo[2.2.1]hept-2-yl; 2-(methyl)cyclohexyl; 1,4-dioxaspiro[4.5]dec-8-yl; N-(prop-2-yn-yl(oxy (carbonyl)))piperidine-4-yl; piperidine-4-yl; bicyclo[2.2.2] octane-2-yl; methyl; (tetrahydro-2H-pyran-4-yl)methyl; 4-(isopropoxy(imino))cyclohexyl; N-(phenyl(carbonyl))piperidine-4-yl; phenylmethyl; N -(methoxy(carbonyl))piperidine-4-yl; cyclopentyl; 4-(tertbutyl)cyclohexyl; 3,3-dimethylbutyl; 2,4-(dimethyl(cyclohex-3-ene-yl))methyl; 4-oxocyclohexyl; 3,3-dimethyl-1,5-dioxaspiro[5.5]undecane-9-yl; 4-(ethoxy(imino))cyclohexyl; bicyclo[3 .2.1]octane-3-yl; bicyclo[3.2.1]octane-2-yl; 6,6-dimethylbicyclo[3.1.1]hept-2--ene-2-yl; ethyipropyl; N-(pyrazine 2-yl) piperidine-4-yl; 4-(trifluoromethyl)cyclohexyl; 3-methylbutyl; 4-(phenyl(oxy(imino)))cyclohexyl; (cyclohex-1-ene-yl)methyl; 4-(cyano-4-(phenyl))cyclohexyl; 4-(prop-2-ene-yl(oxy(imino)))cyclohexyl; tetrahydro-2H-thiopyran-4-yl; cyclopentylmethyl; cyclononyl; cyclobuty; adamantyl; 8-ethoxycarbonyl-8-azabicyclo[3.2.1]octane-3-yl; 3-(trifluoromethyl)cyclohexyl; bicyclo[3.3.1 ]nonane-9-yl; N-(cyclopropyl(carbonyl))piperidine-4-yl; 4-isopropyl; spiro[5.5]undecane-2-yl; 4-(phenyl)cyclohexyl; (tetrahydro-2H-pyran-4yl)methyl; (bicyclo[2.2.1]hept-2-yl)methyl; 4-(3-ethyl-1,2,4-thiadiazole-5-yl)cyclohexyl; N-(3ethyl-1,2, 4-thiadiazole-5-yl)piperidine-4-yl; cyclohexylmethyl; and 4-(3-methyl-1,2,4-thiadiazole-5-yl)cyclohexyl.

26. The compound of claim 1, wherein $R_2$ is hydrogen or optionally substituted straight or branched $C_{1-6}$ aliphatic.

27. The compound of claim 26, wherein $R_2$ is optionally substituted straight or branched $C_{1-6}$ alkyl.

28. The compound of claim 27, wherein $R_2$ is optionally substituted methyl, ethyl, propyl, isopropyl, butyl, sec-butyl, tert-butyl, pentyl, isopentyl, or neohexyl.

29. The compound of claim 28, wherein $R_2$ is methyl, ethyl, or propyl, each of which is optionally substituted with 1-3 of halo, hydroxy, oxo, cyano, or optionally substituted cycloaliphatic, optionally substituted heterocycloaliphatic, optionally substituted aryl, optionally substituted heteroaryl, or optionally substituted alkoxy.

30. The compound of claim 26, wherein $R_2$ is optionally substituted $C_{2-6}$ alkenyl or optionally substituted $C_{2-6}$ alkynyl.

31. The compound of claim 30, wherein $R_2$ is prop-2-ene-yl, but-2-ene-yl, but-3-ene-yl, but-2-yn-yl, or but-3-yn-yl, each of which is optionally substituted with 1-3 of halo, hydroxy, oxo, cyano, or optionally substituted cycloaliphatic, optionally substituted heterocycloaliphatic, optionally substituted aryl, optionally substituted heteroaryl, or optionally substituted alkoxy.

32. The compound of claim 27, wherein $R_2$ is one selected from hydrogen, but-2-yn-yl; isopropyl, propyl, 2-(oxo)propyl, ethyl, (methoxy)ethyl, 2-(methyl)propyl, methyl, (phenyl)methyl, prop-2-ene-yl, and 2-(phenyl-2-(oxo))ethyl.

33. The compound of claim 1, wherein $R_3$ is independently $-Z^C R_6$, wherein each $Z^C$ is independently a bond or an optionally substituted branched or straight $C_{1-6}$ aliphatic chain wherein up to two carbon units of $Z^C$ are optionally and independently replaced by $-CO-$, $-CS-$, $-CONR^C-$, $-CONR^C NR^C-$, $-CO_2-$, $-OCO-$, $-NR^C CO_2-$, $-O-$, $-NR^C CONR^C-$, $-OCONR^C-$, $-NR^C NR^C-$, $-NR^C CO-$, $-SO-$, $-SO_2-$, $-NR^C-$, $-SO_2 NR^C-$, $-NR^C SO_2-$, or $-NR^C SO_2 NR^C-$; each $R_6$ is independently $R^C$, halo, $-OH$, $-NH_2$, $-NO_2$, $-CN$, or $-OCF_3$; and each $R^C$ is independently hydrogen, optionally substituted $C_{1-8}$ aliphatic group, optionally substituted cycloaliphatic, optionally substituted heterocycloaliphatic, optionally substituted aryl, or optionally substituted heteroaryl.

34. The compound of claim 33, wherein $R_3$ is $-Z^C R_6$, $Z^C$ is a bond, and $R_6$ is hydrogen.

35. The compound of claim 1, wherein X is $-O-$.

36. A compound selected from:

1

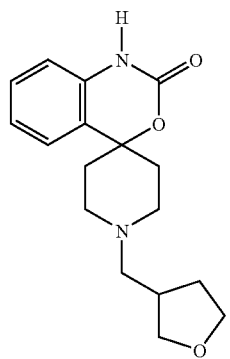

2

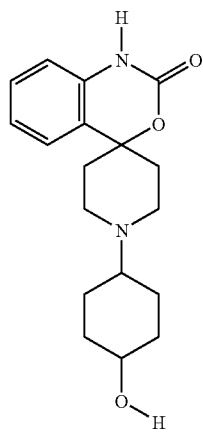

3

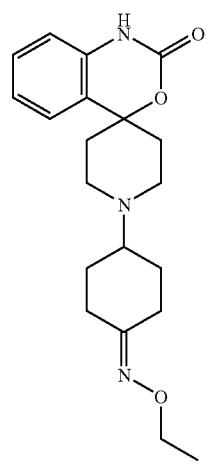

-continued
| 4 | 5 | 6 |
|---|---|---|
| 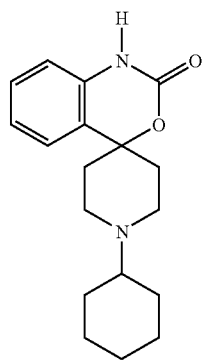 | 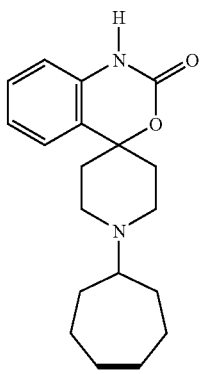 | 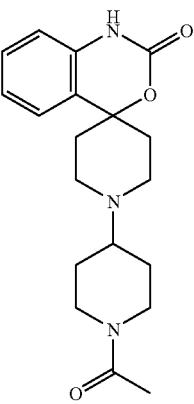 |
| 7 | 8 | 9 |
| 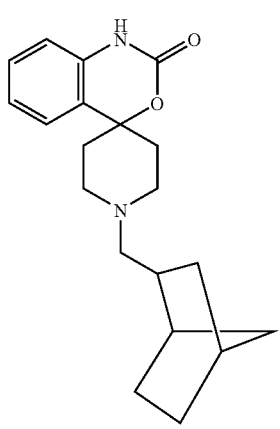 | 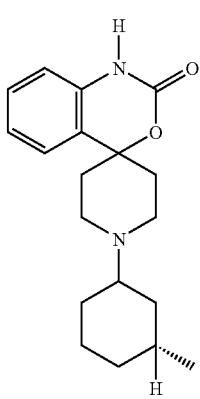 | 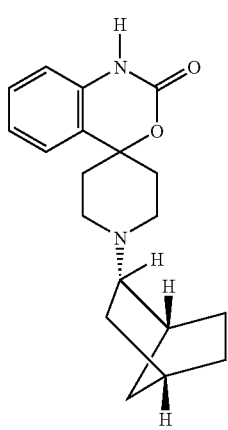 |
| 10 | 11 | 12 |
| 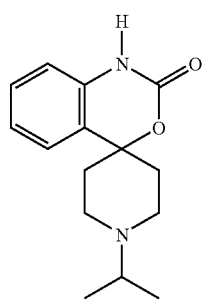 | 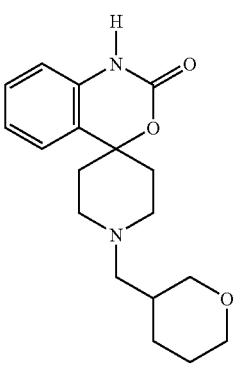 | 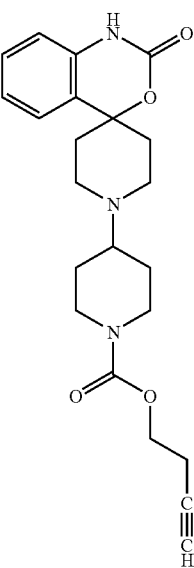 |

-continued
13
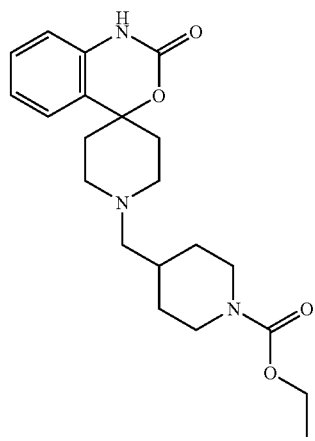
14
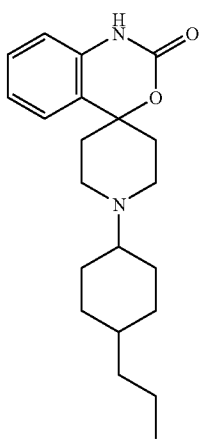
15
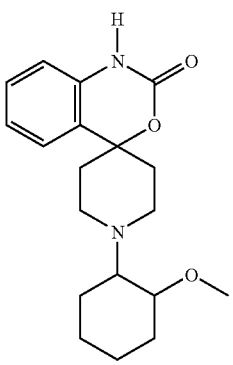
16
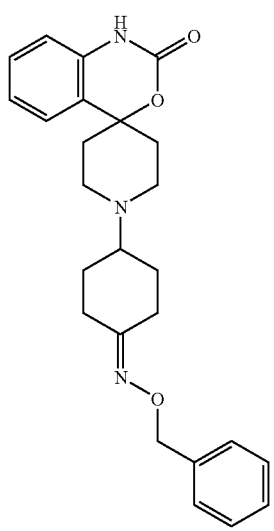
17
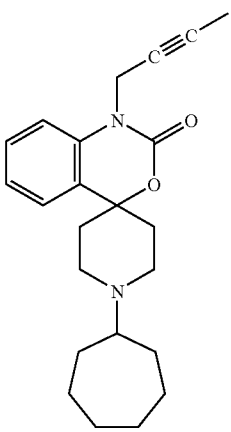
18
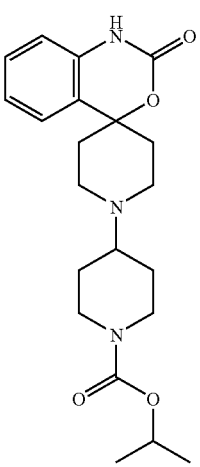
19
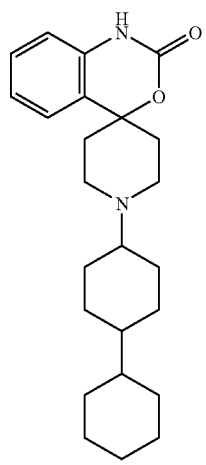
20
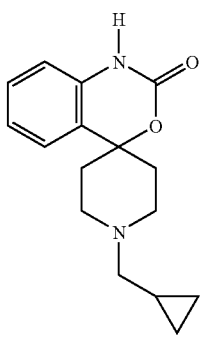
21
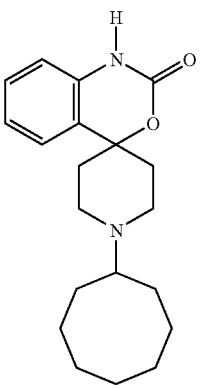

-continued
22
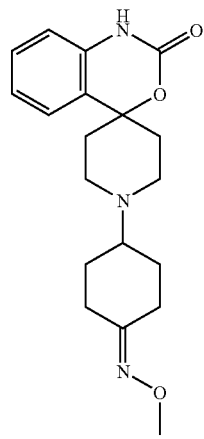
23
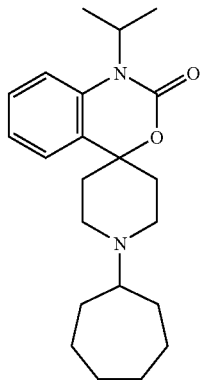
24
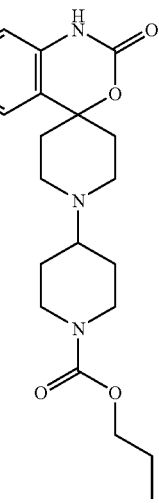
25
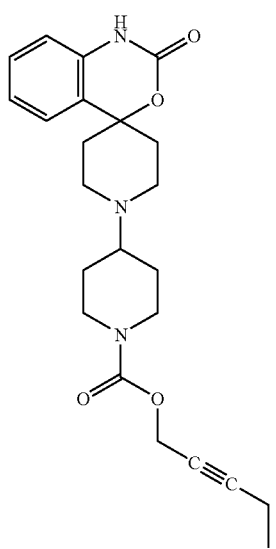
26
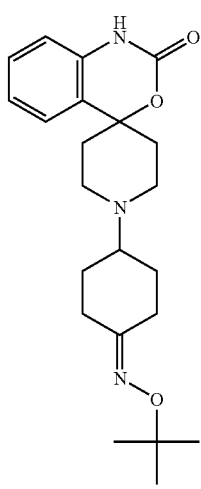
27
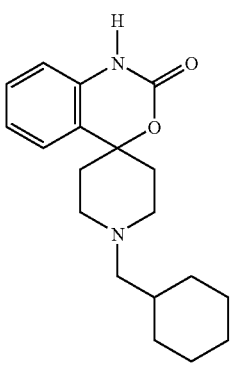

-continued
28
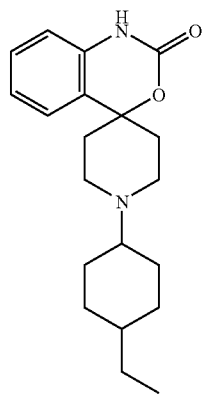
29
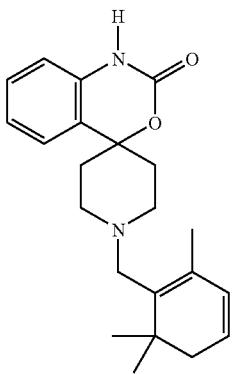
30
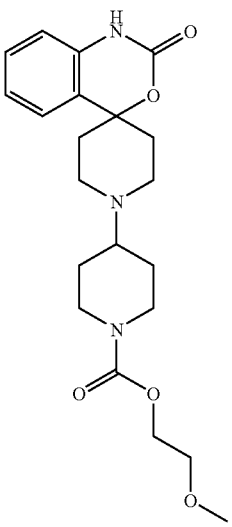
31
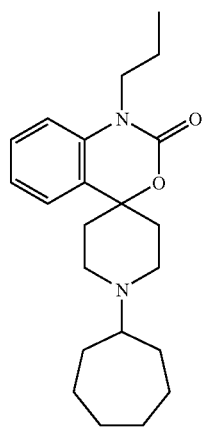
32
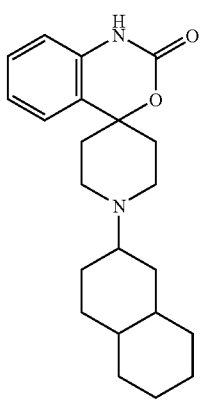
33
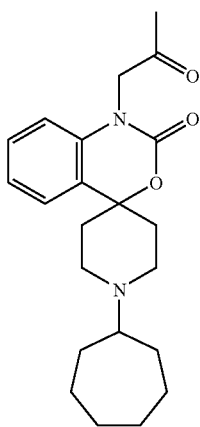
34
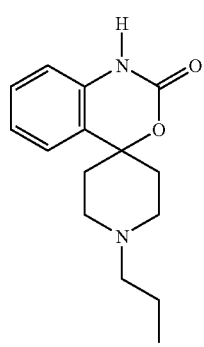
35
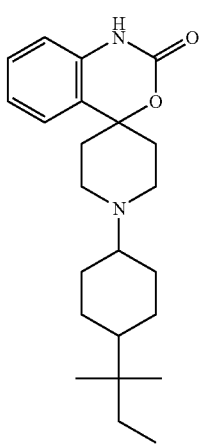
36
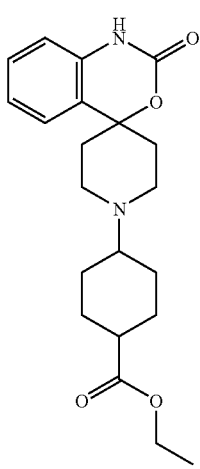

-continued
| 37 | 38 | 39 |
|---|---|---|
| 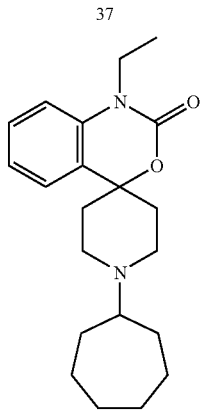 | 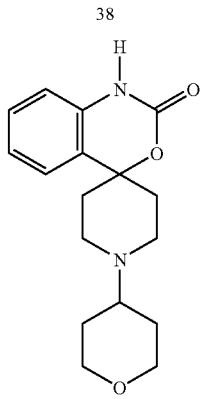 | 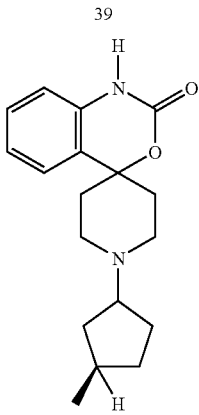 |
| 40 | 41 | 42 |
| 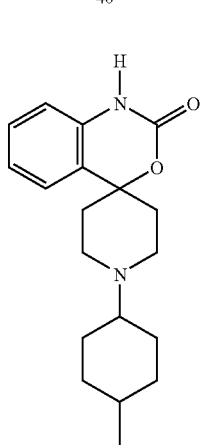 | 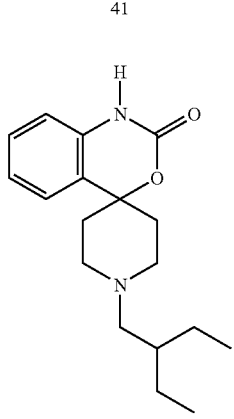 | 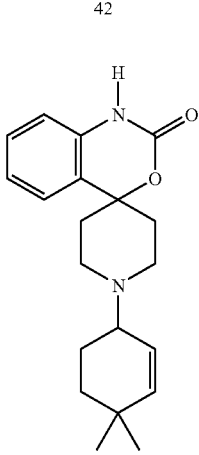 |
| 43 | 44 | 45 |
| 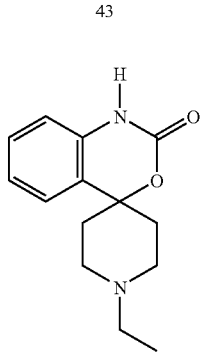 | 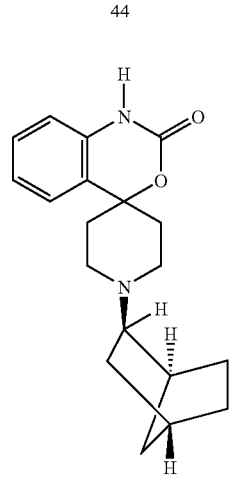 | 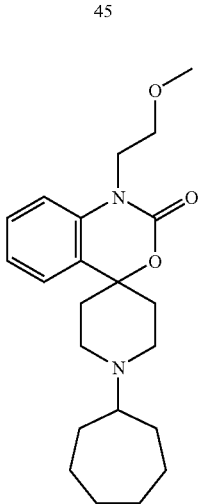 |

-continued
| 46 | 47 | 48 |
|---|---|---|
| 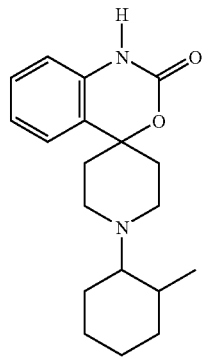 | 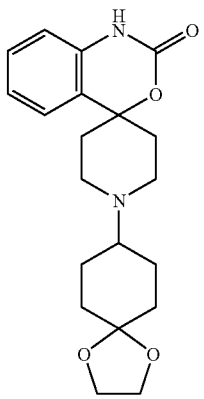 | 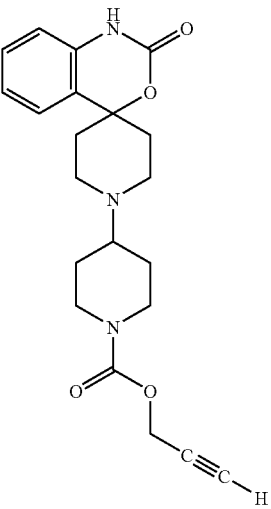 |
| 49 | 50 | |
|---|---|---|
| 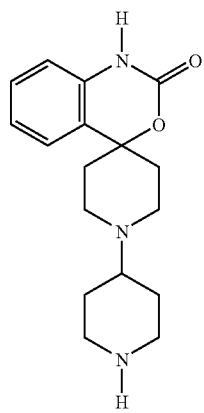 | 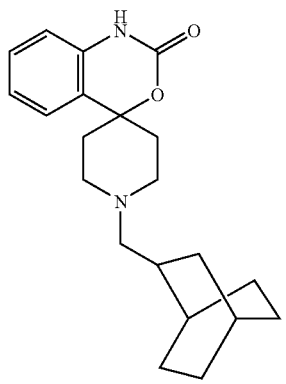 | |
| 52 | 53 | 54 |
|---|---|---|
| 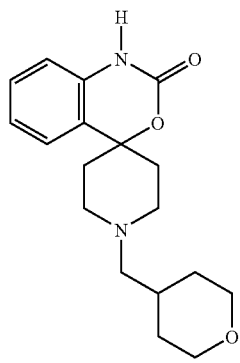 | 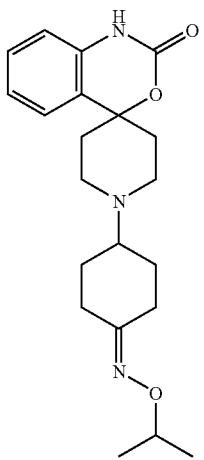 | 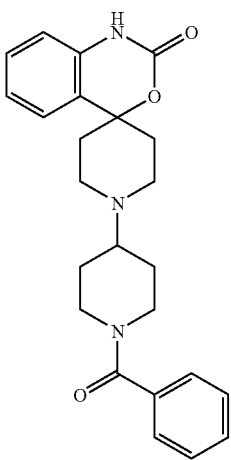 |

| 55 | 56 | 57 |
|---|---|---|
| 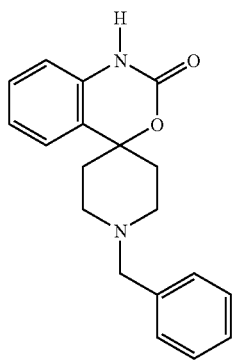 | 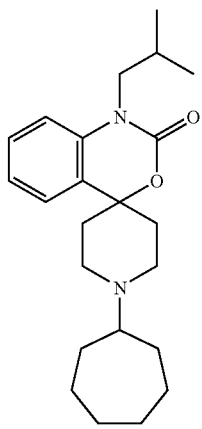 | 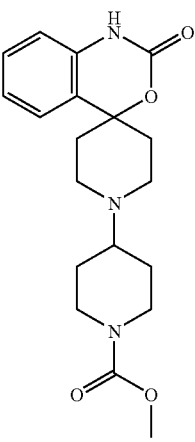 |
| 58 | 59 | 60 |
| 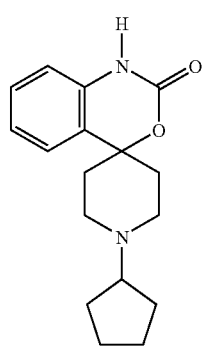 | 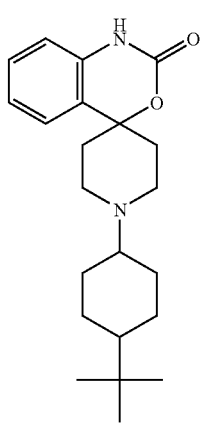 | 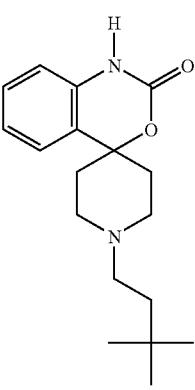 |
| 61 | 62 | 63 |
| 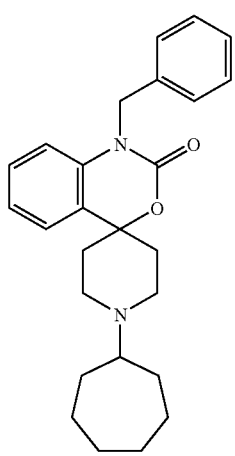 | 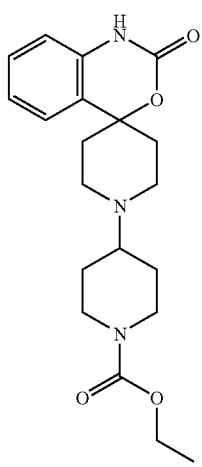 | 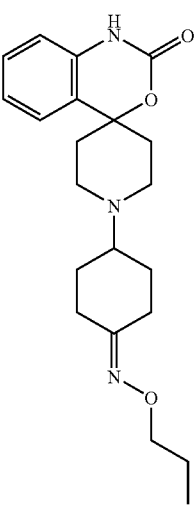 |

-continued
| 64 | 65 | 66 |
|---|---|---|
| 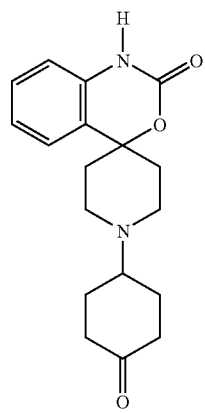 | 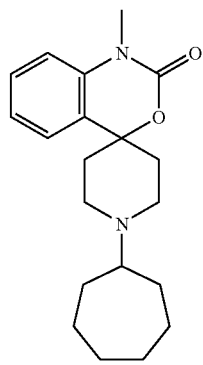 | 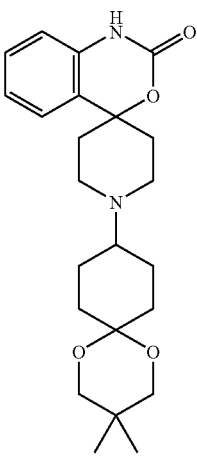 |
| 67 | 68 | 69 |
| 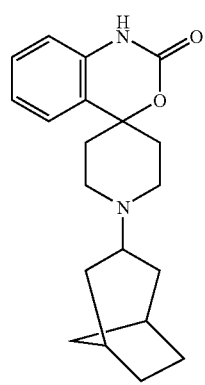 | 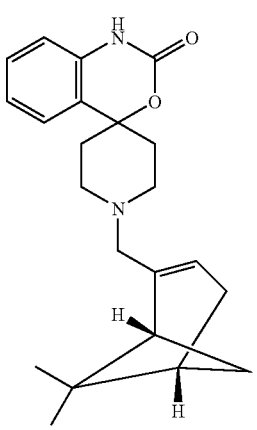 | 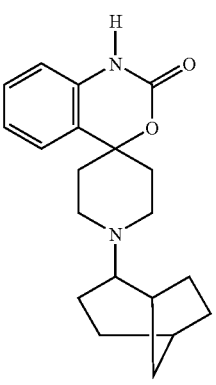 |
| 70 | 71 | 72 |
| 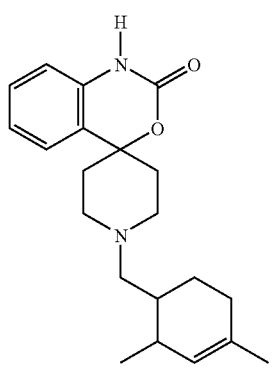 | 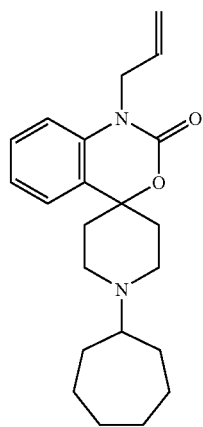 | 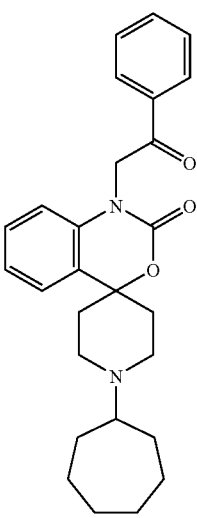 |

-continued
| 73 | 74 | 75 |
|---|---|---|
| 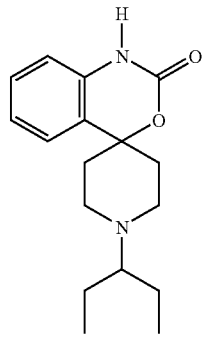 | 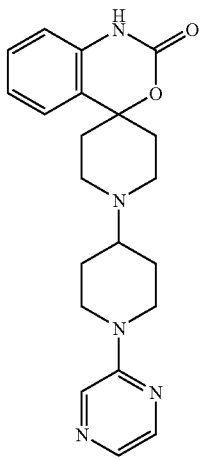 | 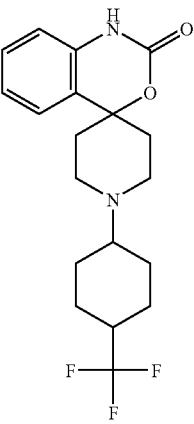 |
| 76 | 77 | 78 |
| 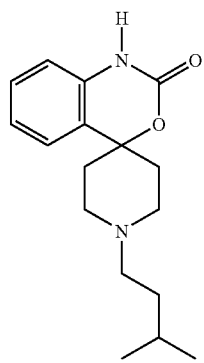 | 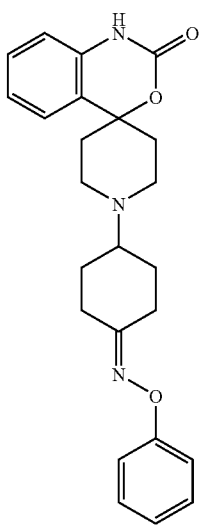 | 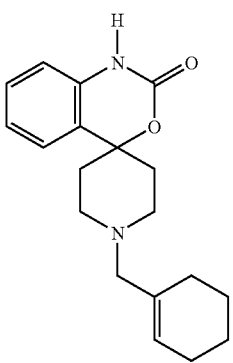 |
| 79 | 80 | 81 |
| 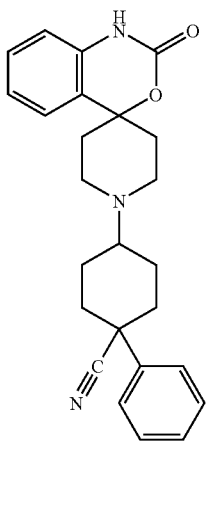 | 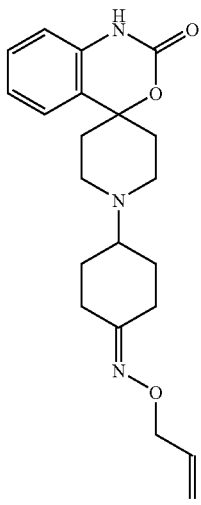 | 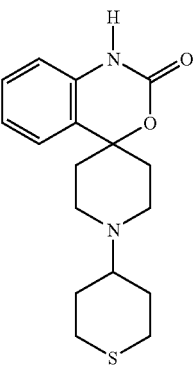 |

-continued
| 82 | 83 | 84 |
|---|---|---|
| 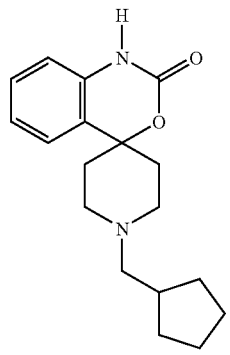 | 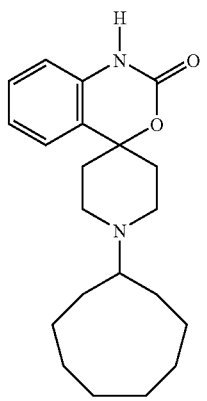 | 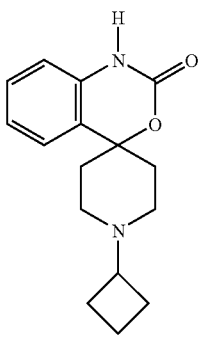 |
| 85 | 86 | 87 |
|---|---|---|
| 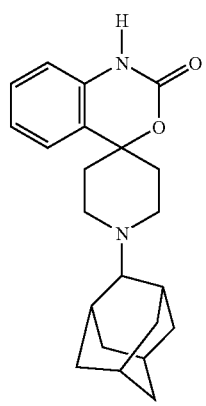 | 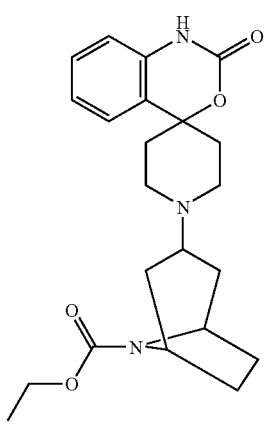 | 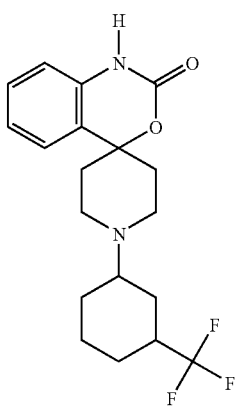 |
| 88 | 89 | 90 |
|---|---|---|
| 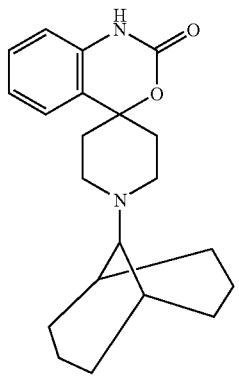 | 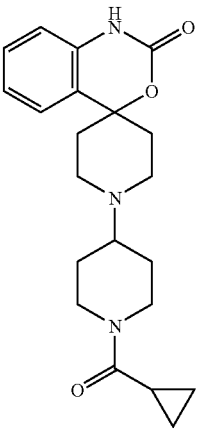 | 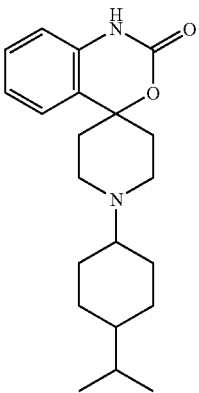 |

-continued
92 93
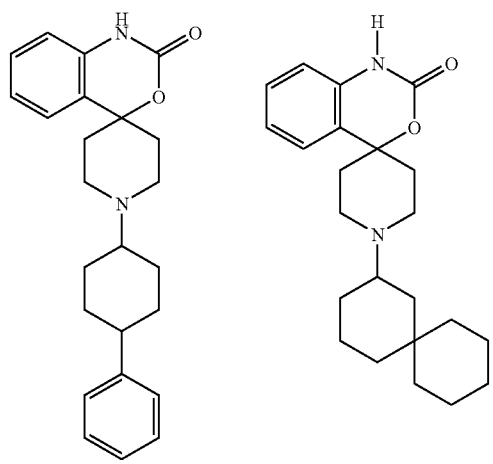
94 95 96
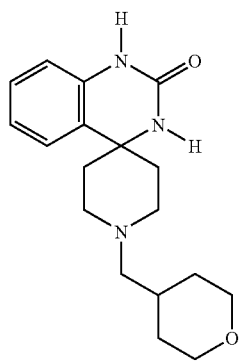 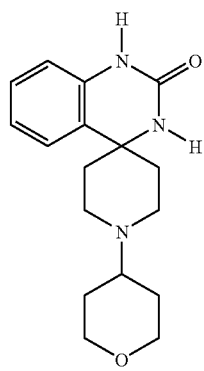 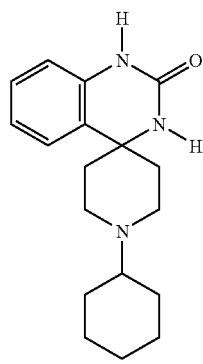
97 98 99
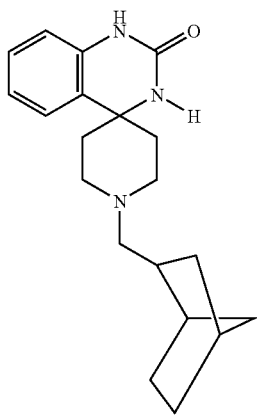 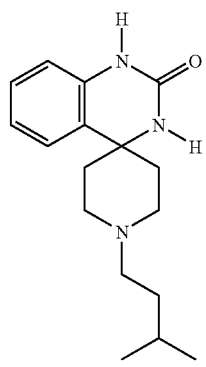 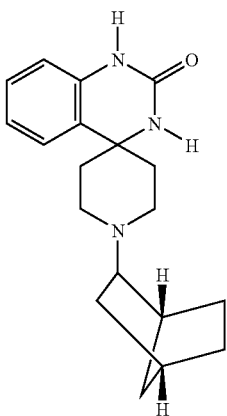

-continued
| 100 | 101 | 102 |
|---|---|---|
| 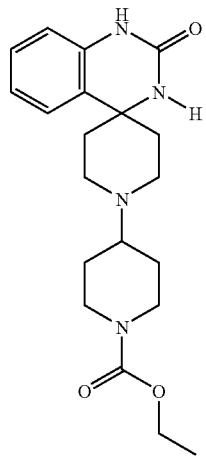 | 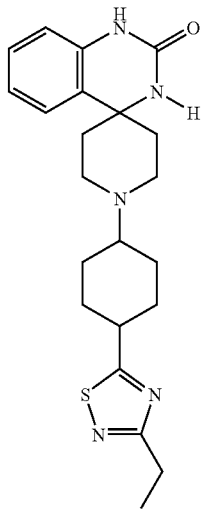 | 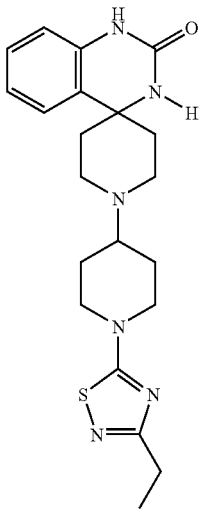 |
| 103 | 104 | 105 |
|---|---|---|
| 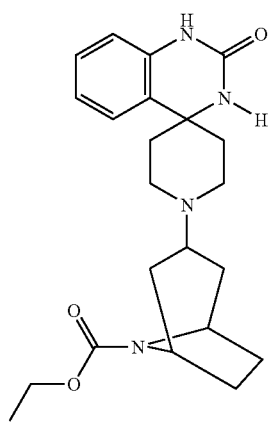 | 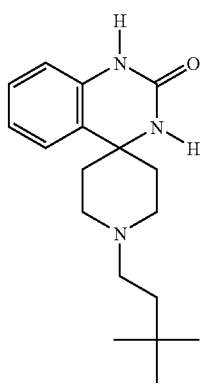 | 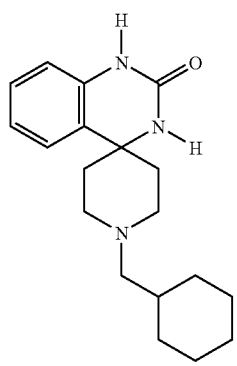 |

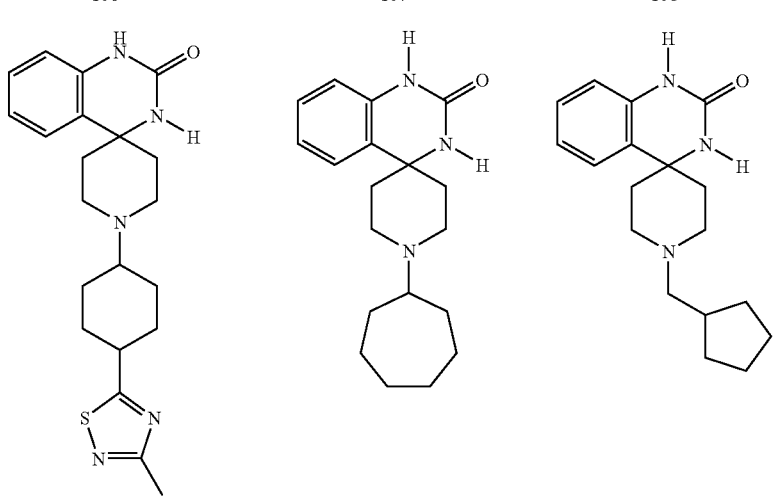
37. A pharmaceutical composition comprising a compound according to claim 36 and a pharmaceutical carrier.
* * * * *